United States Patent
Yamazaki et al.

(10) Patent No.: US 7,371,773 B2
(45) Date of Patent: May 13, 2008

(54) BREAST CANCER RESISTANCE PROTEIN (BCRP) INHIBITOR

(75) Inventors: Ryuta Yamazaki, Tokyo (JP); Yukiko Nishiyama, Tokyo (JP); Tomio Furuta, Tokyo (JP); Takeshi Matsuzaki, Tokyo (JP); Hiroshi Hatano, Tokyo (JP); Oh Yoshida, Tokyo (JP); Masato Nagaoka, Tokyo (JP); Ritsuo Aiyama, Tokyo (JP); Shusuke Hashimoto, Tokyo (JP); Yoshikazu Sugimoto, Chiba (JP)

(73) Assignee: Kabushiki Kaisha Yakult Honsha, Tokyo (JP)

( * ) Notice: Subject to any disclaimer, the term of this patent is extended or adjusted under 35 U.S.C. 154(b) by 168 days.

(21) Appl. No.: 10/544,064

(22) PCT Filed: Feb. 3, 2004

(86) PCT No.: PCT/JP2004/001067

§ 371 (c)(1),
(2), (4) Date: Aug. 2, 2005

(87) PCT Pub. No.: WO2004/069243

PCT Pub. Date: Aug. 19, 2004

(65) Prior Publication Data

US 2006/0128636 A1 Jun. 15, 2006

(30) Foreign Application Priority Data

Feb. 4, 2003 (JP) ............................ 2003-026856

(51) Int. Cl.
*A61K 31/415* (2006.01)
(52) U.S. Cl. .................................. 514/388; 514/402
(58) Field of Classification Search .................... None
See application file for complete search history.

(56) References Cited

U.S. PATENT DOCUMENTS

| 3,151,148 | A | | 9/1964 | Hughes et al. |
| 5,525,632 | A | * | 6/1996 | Obsumi et al. ............. 514/646 |
| 5,731,353 | A | * | 3/1998 | Ohsumi et al. ............. 514/646 |
| 6,992,106 | B2 | * | 1/2006 | Morinaga et al. .......... 514/548 |
| 2006/0128636 | A1 | | 6/2006 | Yamazaki et al. |

FOREIGN PATENT DOCUMENTS

| EP | 0 640 586 | | 3/1995 |
| EP | 0 641 767 | | 3/1995 |
| EP | 0 731 085 | A1 | 9/1996 |
| EP | 1 068 870 | A1 | 1/2001 |
| WO | 93/19746 | | 10/1993 |
| WO | 99/07668 | | 2/1999 |
| WO | 99/40056 | | 8/1999 |

OTHER PUBLICATIONS

Yoo et al., "Synthesis of an Estrogen Receptor β-Selective Radioligand: . . . ," Journal of Medicinal Chemistry, 48(20), 6366-6378 (2005); Web published on Sep. 13, 2005.*

Yoo et al., "Synthesis of an Estrogen Receptor β-Selective Radioligand: . . . ," □□Journal of Medicinal Chemistry, 48(20), 6366-6378 (2005); Web published on Sep. 13, 2005.*

(Continued)

*Primary Examiner*—L. E. Crane
(74) *Attorney, Agent, or Firm*—Oblon, Spivak, McClelland, Maier & Neustadt, P.C.

(57) ABSTRACT

The invention provides a drug which inhibits BCRP.

A breast cancer resistance protein inhibitor containing, as an active ingredient, a diphenylacrylonitrile derivative represented by the following formula (1):

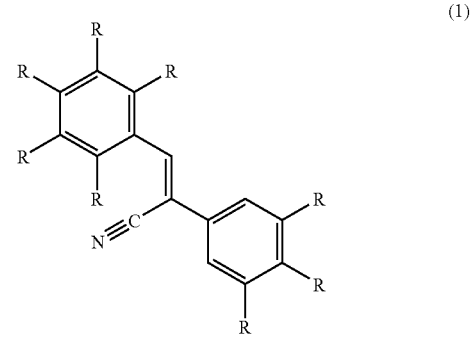

[wherein, each of 8 R's, which are the same or different from one another, represents a hydrogen atom, a hydroxyl group, a nitro group, an amino group, an acetylamino group (—NHCOCH$_3$ group); a cyano group (—CN group); a formyl group (—CHO group), —COOR$_1$ (R$_1$ is hydrogen or C1-C4 alkyl), —O(CH$_2$)$_n$COOR$_2$ (n=1–7: R$_2$ is hydrogen or C1-C4 alkyl), —OOCCH$_2$CH$_2$COOR$_3$ (R$_3$ is hydrogen, C1-C4 alkyl, (Z)-2-(3,4-dimethoxy-phenyl)-3-(4-hydroxy-phenyl)-acrylonitrile, or glycopyranosyl), a C1-C8 alkoxy group, a C1-C4 alkyl group, a halogen atom, a C1-C4 alkoxy C1-C4 alkoxy C1-C4 alkoxy group, a C2-C8 acyloxy group, a C2-C8 halogenoacyloxy group, a methylenedioxy group, a trifluoromethyl group, a phosphate group (i.e., —OP(O)(OH)$_2$) or a salt thereof, a sulfate group (i.e., —OSO$_3$H) or a salt thereof, a glycopyranosyl group or a salt thereof, a phosphate ester of a glycopyranosyl group or a salt of the ester, a sulfate ester of a glycopyranosyl group or a salt of the ester, or a piperidinopiperidinocarbonyloxy group], an ester thereof, or a salt thereof.

9 Claims, 9 Drawing Sheets

OTHER PUBLICATIONS

Dore et al., "Antitumor Chemotherapy and Synthesis of Natural Antitumor Agents. VI. Cycotoxic Antitumor Activity of Trans-[alpha]-stilbenes in vitro and Antitumor Activity in vivo Against Krebs II Ascites Carcinoma," J. de Pharmacia de Belgique, 28(1), 3-23 (1973); only Caplus abstract supplied, see structure at the top of p. No. 126.*

Gilbert et al. "Study of the Effects of Basic Di- and Tri-phenyl Derivatives on Malignant Cell Proliferation: An Example of the Application of Correspondence Factor Analysis to Structure-Activity Relationships (SAR)", Quant. Struct-Act. Relat., vol. 13, pp. 262-274 1994.

Ohsumi et al. "Novel Combretastatin Analogues Effective against Murine Solid Tumors: Design and Structure-Activity Relationships", J. Med. Chem., vol. 41, pp. 3022-3032 1998.

F. Michel, et al., "The Effect of Various Acrylonitriles and Related Compounds on Prostaglandin Biosynthesis", Prostaglandins, XP-002365729, vol. 27, No. 1, Jan. 1984, pp. 69-84.

Derwent Publications, AN 1993-340587, XP-002365731, JP 05-249517, Sep. 28, 1993.

J.T. Stewart, "Synthesis and Biological Evaluation of Substituted α-Phenylcinnamonitriles", Journal of Pharmaceutical Sciences, XP-008059392, vol. 60, No. 8, Aug. 1971, pp. 1244-1245.

U.S. Appl. No. 11/909,805, filed Sep. 27, 2007, Yamazaki et al.

Sato et al, Cancer Research, 1991, 51, pp. 2420-2424.

Miyamoto et al, Cancer Research, 1993, 53, pp. 1555-1559.

Newman et al, Cancer Research, 2000, 60, pp. 2964-2972.

* cited by examiner

- ● — A549
- ○ — A549/SN-38-4

*FIG. 3A*
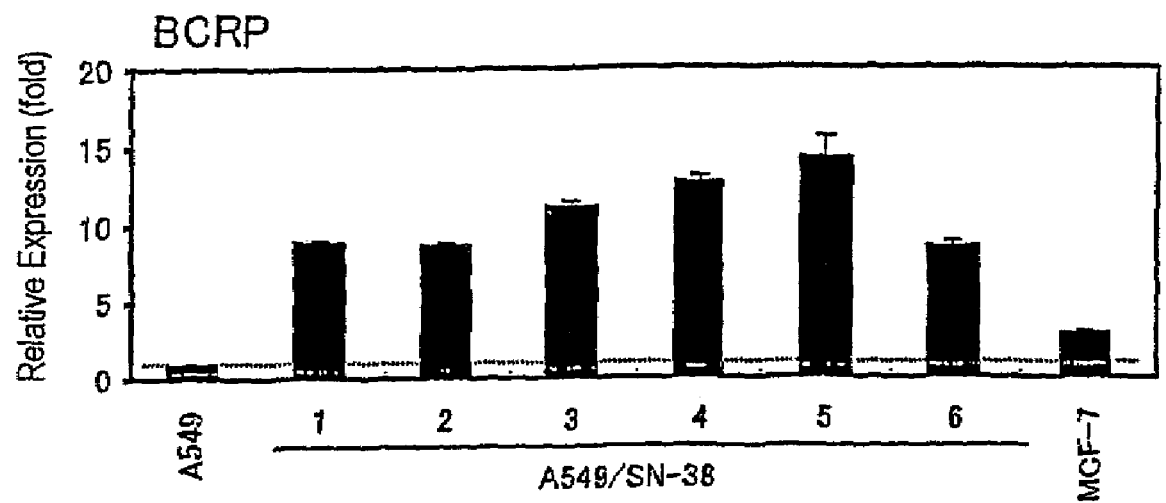
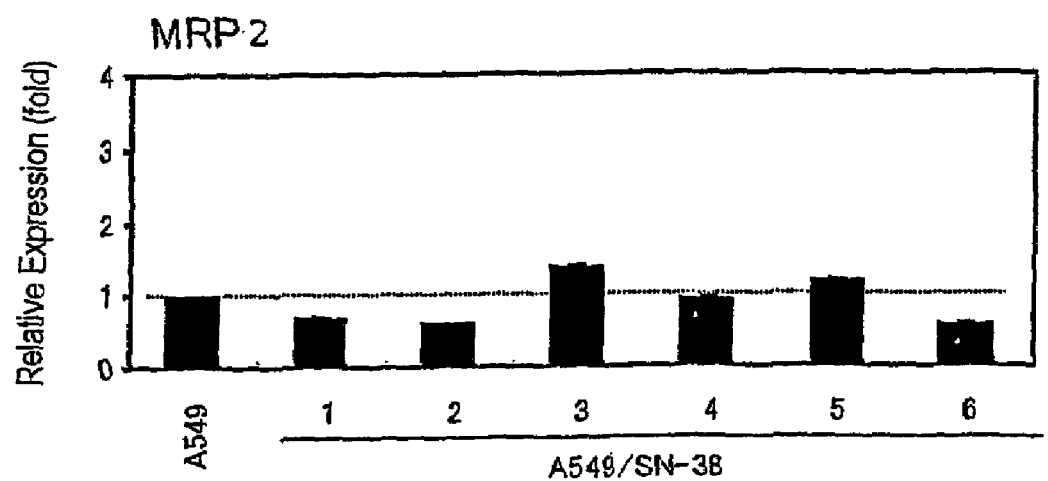
*FIG. 3B*

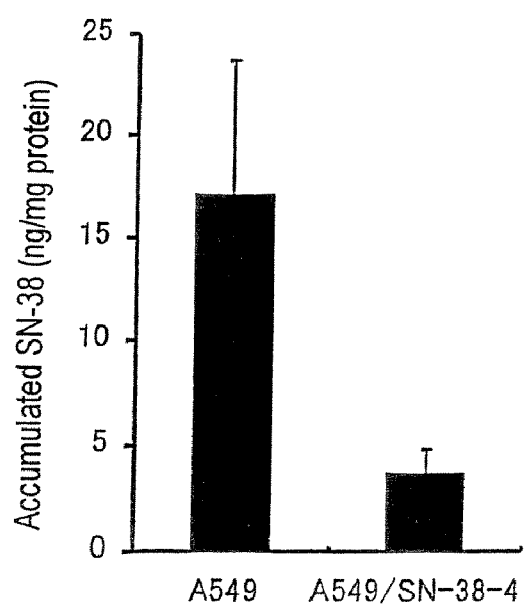 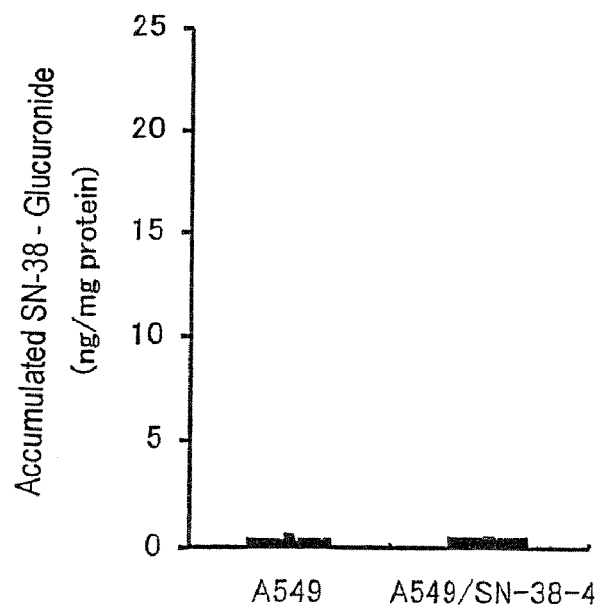
*FIG. 4A*  *FIG. 4B*

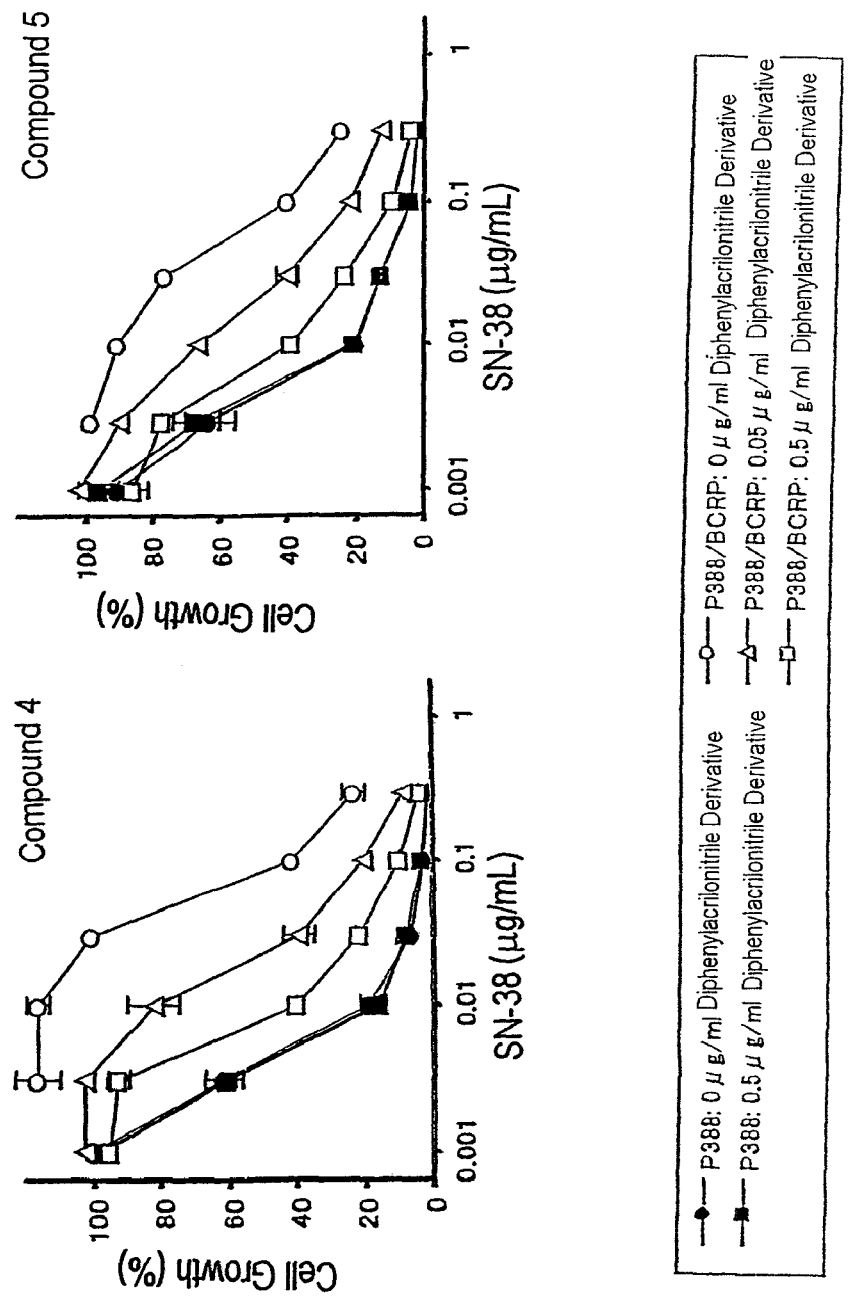

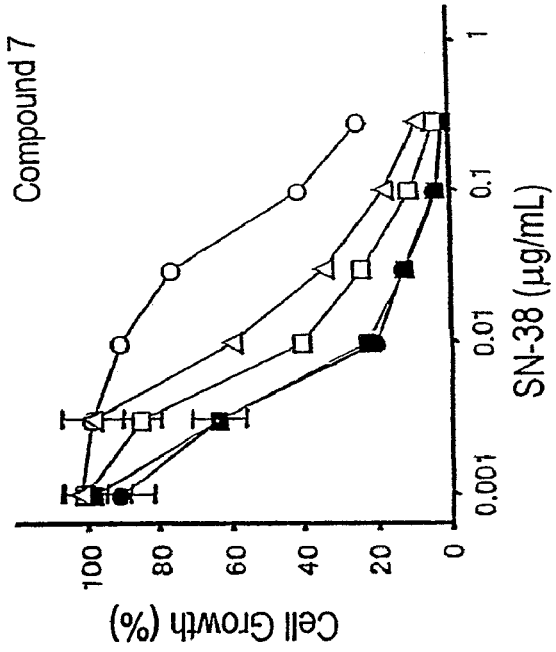
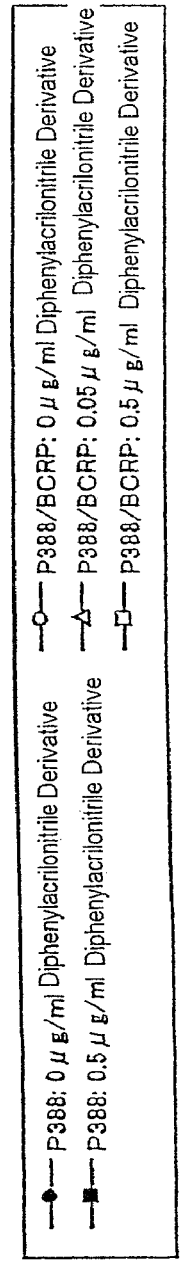
FIG. 6E
FIG. 6F

BREAST CANCER RESISTANCE PROTEIN (BCRP) INHIBITOR

TECHNICAL FIELD

The present invention relates to a breast cancer resistance protein (BCRP) inhibitor.

BACKGROUND ART

Serious problems associated with cancer chemotherapy include intrinsic resistance to an anticancer drug, which invalidates the effect of the anticancer drug from the beginning of cancer therapy, and development of acquired resistance to an anticancer drug (i.e., reduction of the effect of the drug, which is caused by long-term continuous administration thereof). Overcoming such anticancer drug resistance has been envisaged to lead to improvement of the performance of cancer chemotherapy, and thus attempts have been made to elucidate various resistance mechanisms. Particularly, expression of a drug transporter, which actively transports an anticancer drug out of cancer cells, thereby reducing the amount of intracellular accumulation of the drug, is considered to play an important role in such a resistance mechanism.

Particularly, P-glycoprotein, which is a drug transporter discovered in the 1970s, and is encoded by an MDR1 gene, has been considered a potent target molecule of a multidrug-resistance-overcoming agent, since this protein causes cross-resistance to a plurality of anticancer drugs having different chemical structures and action mechanisms. However, it has been gradually elucidated that a drug transporter other than P-glycoprotein is also associated with an anticancer drug resistance mechanism, and demand has arisen for development of a resistance-overcoming agent which targets such a drug transporter.

Under such circumstances, there was discovered, in 1998, breast cancer resistance protein (BCRP), which is a drug transporter belonging to a group which is called "ATP-binding cassette (ABC) transporter superfamily" to which P-glycoprotein also belongs (see Proc. Natl. Acad. Sci. USA 95, 15665-15670 (1998)). BCRP has a structure including only one ATP-binding cassette, which differs from that of P-glycoprotein or another drug transporter, which has two ATP-binding cassettes. BCRP is intimately involved in the mechanism of resistance to a topoisomerase I inhibitor (e.g., irinotecan hydrochloride (CPT-11) or topotecan) or to a topoisomerase II inhibitor (e.g., mitoxantrone). Meanwhile, BCRP has been elucidated to exhibit substrate specificity different from that of P-glycoprotein, since BCRP does not act on, for example, paclitaxel or vincristine, which is excreted by P-glycoprotein, and BCRP is involved in excretion of a camptothecin derivative (e.g., CPT-11 or 7-ethyl-10-hydroxycamptothecin (SN-38: active metabolite of CPT-11)), which is rarely excreted extracellularly by P-glycoprotein (see Cancer Res. 59, 5938-5946 (1999)). In addition, BCRP has been suggested to be involved in the limitation of the bioavailability of an orally administered anticancer drug (see J. Clin. Oncol. 20, 2943-2950 (2002)). In view of the foregoing, demand has arisen for development of a BCRP inhibitor, which is envisaged to exhibit the effect of overcoming anticancer drug resistance that is not overcome by a conventional resistance-overcoming agent, and to improve the bioavailability of an anticancer drug.

Hitherto, a variety of P-glycoprotein inhibitors have been developed for the purpose of overcoming anticancer drug resistance. However, since few BCRP-specific inhibitors have been reported, and such inhibitors have been considered to exhibit unsatisfactory BCRP-inhibiting effect, demand has arisen for a drug which exhibits more potent BCRP-inhibiting effect (see Mol. Cancer. Ther. 1, 427-434 (2002)). Incidentally, some diphenylacrylonitrile derivatives have been reported to exhibit anticancer effect (see J. Med. Chem. 41, 3022-3032 (1998). However, a diphenylacrylonitrile derivative exhibiting anticancer-drug-resistance-overcoming effect or BCRP-inhibiting effect has not yet been known.

An object of the present invention is to provide a BCRP inhibitor.

DISCLOSURE OF THE INVENTION

With an aim to attain the above object, the present inventors have screened a variety of compounds through use of a cancer cell line whose anticancer drug resistance has been imparted by BCRP, and have found that the diphenylacrylonitrile derivatives represented by the following formula (1) exhibit potent BCRP-inhibiting effect. The present invention has been accomplished on the basis of this finding.

Accordingly, the present invention provides a BCRP inhibitor containing, as an active ingredient, a diphenylacrylonitrile derivative represented by the following formula (1) or a salt thereof:

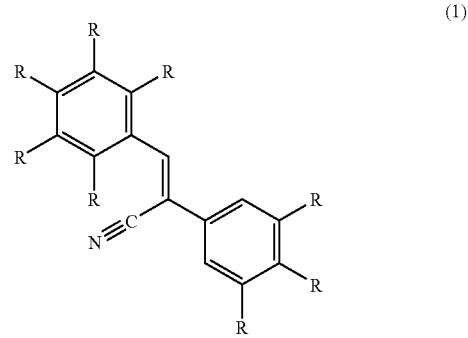

(1)

[wherein, each of 8 R's, which are the same or different from one another, represents a hydrogen atom, a hydroxyl group, a nitro group, an amino group, an acetylamino group (—NHCOCH$_3$ group), a cyano group (—CN group), a formyl group (—CHO group), —COOR$_1$ (R$_1$ is hydrogen or C1-C4 alkyl), —O(CH$_2$)$_n$COOR$_2$ (n=1-7: R$_2$ is hydrogen or C1-C4 alkyl), —OOCCH$_2$CH$_2$COOR$_3$ (R$_3$ is hydrogen, C1-C4 alkyl, or glycopyranosyl), a C1-C8 alkoxy group, a C1-C4 alkyl group, a halogen atom, a C1-C4 alkoxy C1-C4 alkoxy C1-C4 alkoxy group, a C2-C8 acyloxy group, a C2-C8 halogenoacyloxy group, a methylenedioxy group, a trifluoromethyl group, a phosphate group (i.e., —OP(O)(OH)$_2$) or a salt thereof, a sulfate group (i.e., —OSO$_3$H) or a salt thereof, a glycopyranosyl group or a salt thereof, a phosphate ester of a glycopyranosyl group or a salt thereof, a sulfate ester of a glycopyranosyl group, or a piperidinopiperidinocarbonyloxy group]; an anticancer-drug-resistance-overcoming agent; and an anticancer-drug-effect-enhancing agent.

The present invention also provides an anticancer drug containing the aforementioned BCRP inhibitor, and an anticancer drug which can serve as a substrate for BCRP.

BRIEF DESCRIPTION OF THE DRAWINGS

FIG. 3 shows the results of real-time RT-PCR quantitative analysis of expression of mRNAs of BCRP (A) and MRP2 (B) in A549 cell line and A549/SN-38 cell lines.

FIG. 4 shows the amount of SN-38 (A) or SN-38-glucuronide (B) accumulated in A549 cell line and A549/SN-38-4 cell line.

BEST MODES FOR CARRYING OUT THE INVENTION

Figure 1A:
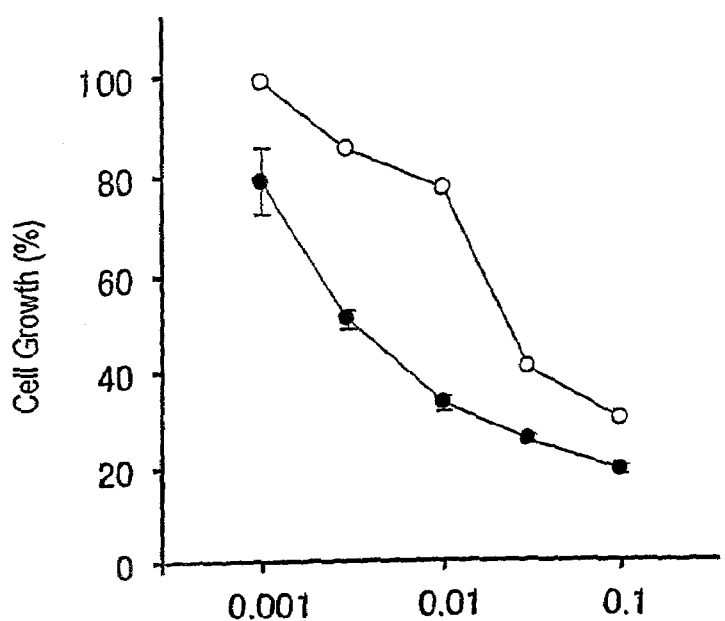
FIG. 1 shows the level of resistance of A549/SN-38-4 cell line to SN-38 (A) or to mitoxantrone (B).

Using resistance-overcoming effect as an index, the present inventors have screened a variety of compounds on a cancer cell line whose anticancer drug resistance had been imparted by BCRP, and have found that the diphenylacrylonitrile derivatives represented by formula (1) exhibit strong BCRP inhibiting action.

In formula (1), specific examples of the C1-C4 alkyl groups denoted by R include methyl, ethyl, n-propyl, isopropyl, and n-butyl group; with methyl and ethyl being particularly preferred. Specific examples of the C1-C8 alkoxy groups include methoxy, ethoxy, n-propoxy, isopropoxy, and n-butoxy group; with methoxy, ethoxy, and n-butoxy being particularly preferred. Specific examples of the halogen atom include fluorine, chlorine, bromine, and iodine; with fluorine, chlorine, and bromine being particularly preferred. The C1-C4 alkoxy C1-C4 alkoxy C1-C4 alkoxy groups are preferably C1-C2 alkoxy C1-C2 alkoxy C1-C2 alkoxy groups; with a methoxyethoxymethoxy group being particularly preferred. Specific examples of the C2-C8 acyloxy groups include acetoxy, propionyloxy, and butylyloxy. Specific examples of the —COOR$_1$ group include carboxy, methoxycarbonyl, and ethoxycarbonyl; with methoxycarbonyl being particularly preferred. Specific examples of the —O(CH$_2$)$_n$COOR$_2$ group (n=1–7) include —OCH$_2$COOC$_2$H$_5$, —O(CH$_2$)$_2$COOC$_2$H$_5$, and —O(CH$_2$)$_6$COOC$_2$H$_5$. Specific examples of the —OOCCH$_2$CH$_2$COOR$_3$ group include —OOCCH$_2$CH$_2$COOCH$_3$, —OOCCH$_2$CH$_2$COOC$_2$H$_5$, and —OOCCH$_2$CH$_2$COO— tetraacetylglucopyranosyl Specific examples of the C2-C8 halogenoacyloxy groups include a Br(CH$_2$)$_7$COO— group. Specific examples of the glycopyranosyl group include β-D-glucopyranosyl, β-maltosyl, β-maltotriosyl, and β-D-2-deoxy-2-aminoglucopyranosyl; with β-D-glucopyranosyl, β-maltosyl, and β-maltotriosyl being particularly preferred.

The aforementioned diphenylacrylonitrile derivatives may form pharmacologically acceptable salts through addition of, for example, sodium, potassium, or a hydrochloride, and such pharmacologically acceptable salts also fall within the scope of the present invention. The diphenylacrylonitrile derivatives may exist as solvates, and such solvates also fall within the scope of the present invention. Moreover, the diphenylacrylonitrile derivatives may have isomers, and such isomers and mixtures containing any of the isomers also fall within the scope of the present invention.

In one preferred mode of the present invention, a diphenylacrylonitrile derivative is represented by the following formula (1a):

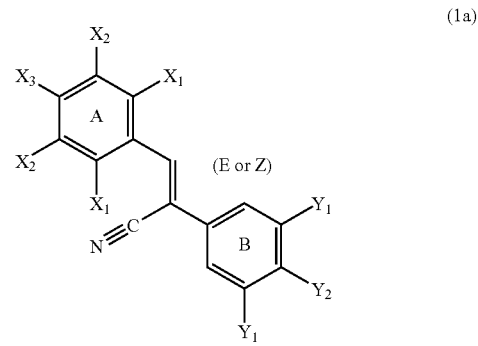

(1a)

[wherein, $X_1$ in ring A represents a hydrogen atom, a hydroxyl group, a halogen atom, a nitro group, an amino group, an acetylamino group (—NHCOCH$_3$), a C2-C8 acyloxy group, a methoxyethoxymethoxy group, or a C1-C8 alkoxy group;

$X_2$ represents a hydrogen atom, a hydroxyl group, a C1-C8 alkoxy group, a halogen atom, a nitro group, an amino group, an acetylamino group (—NHCOCH$_3$), a C2-C8 acyloxy group, a methoxyethoxymethoxy group, a methylenedioxy group, or a C1-C4 alkyl group;

$X_3$ represents a hydrogen atom, a hydroxyl group, a C2-C8 acyloxy group, a C1-C8 alkoxy group, a halogen atom, a nitro group, an amino group, an acetylamino group (—NHCOCH$_3$), a cyano group, a formyl group (—CHO), —COOR$_1$ (R$_1$=hydrogen atom, C1-C4 alkyl group), —O(CH$_2$)nCOOR$_2$ (n=1–7: R$_2$=hydrogen atom, C1-C4 alkyl group), —OOCCH$_2$CH$_2$COOR$_3$ (R$_3$=hydrogen atom, C1-C4 alkyl, (Z)-2-(3,4-dimethoxy-phenyl)-3-(4-hydroxy-phenyl)-acrylonitrile, a glycopyranosyl group), a C2-C8 halogenoacyloxy group, a methylenedioxy group, a phosphate group (—OP(O)(OH)$_2$) and a salt thereof, a sulfate group (—OSO$_3$H) and a salt thereof, a glycopyranosyl group and a salt of the ester, a phosphate ester of a glycopyranosyl group and a salt thereof, a sulfate ester of a glycopyranosyl group and a salt of the ester, a piperidinopiperidinocarbonyloxy group, or a methoxyethoxymethyl group, $Y_1$ in ring B represents a hydrogen atom, a C2-C8 acyloxy group, a trifluoromethyl group, or a C1-C8 alkoxy group; $Y_2$ represents a hydrogen atom, a hydroxyl group, a C2-C8 acyloxy group, a methoxyethoxymethoxy group, —COOR$_1$ (R$_1$=hydrogen atom, C1-C4 alkyl group), —O(CH$_2$)nCOOR$_2$ (n=1–7: R$_2$=hydrogen atom, C1-C4 alkyl group), —OOCCH$_2$CH$_2$COOR$_3$ (R$_3$=hydrogen atom, C1-C4 alkyl, (Z)-2-(3,4-dimethoxy-phenyl)-3-(4-hydroxy-phenyl)-acrylonitrile, a glycopyranosyl group), a C2-C8 halogenoacyloxy group, a methylenedioxy group, a phosphate group (—OP(O)(OH)$_2$) or a salt thereof, a sulfate group (—OSO$_3$H) or a salt thereof, a glycopyranosyl group and a salt of the ester, a phosphate ester of a glycopyranosyl group and a salt of the ester, a sulfate ester of a glycopyranosyl group and a salt of the ester, a piperidinopiperidinocarbonyloxy group, or a C1-C8 alkoxy group].

In a particularly preferred compound of formula (1a), $X_1$ in ring A is a hydrogen atom, a hydroxyl group, an acetoxy group, a halogen atom, a nitro group, an amino group, an acetylamino group (—NHCOCH$_3$), or a methoxy group;

$X_2$ is a hydrogen atom, a hydroxyl group, a methoxy group, an ethoxy group, an acetoxy group, a halogen atom, a nitro group, a amino group, an acetylamino group (—NHCOCH$_3$), a methylenedioxy group, or a methyl group;

$X_3$ is a hydrogen atom, a hydroxyl group, an acetoxy group, a methoxy group, a halogen atom, a nitro group, an amino group, an acetylamino group (—NHCOCH$_3$), a methylenedioxy group, a glycopyranosyl group and a salt thereof, a phosphate ester of a glycopyranosyl group and a salt of the ester, a sulfate ester of a glycopyranosyl group and a salt of the ester, a phosphate group (—OP(O)(OH)$_2$) or a salt thereof, a sulfate group (—OSO$_3$H) or a salt thereof, a piperidinopiperidinocarbonyloxy group, or a methoxyethoxymethoxy group, $Y_1$ in ring B represents a hydrogen atom, a trifluoromethyl group, or a methoxy group;

$Y_2$ is a hydrogen atom, a hydroxyl group, a methoxyethoxymethoxy group, an acetoxy group, or a methoxy group.

Ring A is preferably a mono- to tri-substituted ring. When ring A is a mono-substituted ring, substitution preferably occurs at the 2-, 3- or 4-position; and similarly, in the case of a di-substituted ring, substitution preferably occurs at the 2,3-, 3,4-, or 3,5-positions; and in the case of a tri-substituted ring, substitution preferably occurs at the 3,4,5-positions.

Ring B is preferably a mono- to tri-substituted ring. When ring B is a mono-substituted ring, substitution preferably occurs at the 4-position; and similarly, in the case of a di-substituted ring, substitution preferably occurs at the 3,4-positions; and in the case of a tri-substituted ring, substitution preferably occurs at the 3,4,5-positions.

Among the compounds represented by formula (1a) of the present invention, those which are preferred from another viewpoint have, as ring A, any of the following: 4-hydroxyphenyl, 2-hydroxyphenyl, 4-piperidinopiperidinocarbonyloxyphenyl, 4-acetoxyphenyl, 4-methoxyethoxymethoxyphenyl, 4-hydroxy-3-methoxyphenyl, 3,4-dihydroxyphenyl, 3-hydroxy-2-methoxyphenyl, 3,5-dimethyl-4-hydroxyphenyl, 4-hydroxy-3-ethoxyphenyl, 4-bromophenyl, 2-fluorophenyl, 3-fluorophenyl, 4-fluorophenyl, 2,3-difluorophenyl, 2,4-difluorophenyl, 2,5-difluorophenyl, 2,6-difluorophenyl, 3,4-difluorophenyl, 3,5-difluorophenyl, 2,3,4-trifluorophenyl, 2,3,5-trifluorophenyl, 2,3,6-trifluorophenyl, 2,4,5-trifluorophenyl, 3,4,5-trifluorophenyl, 4-nitrophenyl, 3-nitrophenyl, 2-nitrophenyl, 4-cyanophenyl, 4-aminophenyl, 3-aminophenyl, 4-methoxycarbonylphenyl, 4-chloro-3-nitrophenyl, 2-fluoro-5-nitrophenyl, 3-ethoxy-4-nitrophenyl, 4-OOCCH$_2$CH$_2$COOCH$_3$-phenyl, 4-OOCCH$_2$CH$_2$COOC$_2$H$_5$-phenyl, 4-β-D-glucopyranosylphenyl, 4-hydroxy-3-nitrophenyl, 3,4-methylenedioxy-6-nitrophenyl, 3,4-dimethoxyphenyl, 4-β-maltosyl-phenyl, 4-β-maltotriosyl-phenyl, 2-ethoxy-5-nitrophenyl, 3-hydroxy-4-nitrophenyl, 3-fluoro-2-hydroxyphenyl, 3-fluoro-4-methoxyethoxymethoxyphenyl, 3-fluoro-4-hydroxyphenyl, 4-OP(O) (ONa)$_2$-phenyl, 4-formylphenyl, 4-acetoxy-3-ethoxyphenyl, 4-acetoxy-3-fluorophenyl, 4-OOC(CH$_2$)$_7$Br-phenyl, 3-methoxy-4-OP(O) (ONa)$_2$-phenyl, 4-OP(O) (OH)$_2$-phenyl, 3-methoxy-4-OP(O) (OH)$_2$-phenyl, 4-acetylaminophenyl, 4-(β-D-glucose-6'-OP(O) (ONa)$_2$)-phenyl, 4-OSO$_3$H—N(C$_2$H$_5$)$_3$-phenyl, 4-(β-D-glucose-6'-OP(O) (OH) $_2$)-phenyl, 2-hydroxy-5-nitrophenyl and 4-fluoro-3-nitrophenyl; and, as ring B, any of the following: 4-n-butoxyphenyl, 3,4-dimethoxyphenyl, 3,4,5-trimethoxyphenyl, 4-hydroxyphenyl, 4-methoxyethoxymethoxyphenyl, 4-acetoxyphenyl and 3,5-bis-trifluoromethylphenyl; provided that compounds in which rings A and B both being 4-hydroxyphenyl are excluded. Among such compounds, particularly preferred ones include the following compounds:

(Z)-2-(3,4-dimethoxy-phenyl)-3-(4-hydroxy-phenyl)-acrylonitrile;

4-[(Z)-2-cyano-2-(3,4-dimethoxy-phenyl)-vinyl]-phenyl [1,4']bipiperidinyl-1'-carboxylate;

4-[(Z)-2-cyano-2-(3,4-dimethoxy-phenyl)-vinyl]-phenyl acetate;

(Z)-2-(3,4-dimethoxy-phenyl)-3-[4-(2-methoxyethoxymethoxy)-phenyl]-acrylonitrile;

(Z)-2-(3,4-dimethoxy-phenyl)-3-(3-hydroxy-phenyl)-acrylonitrile;

(Z)-2-(3,4-dimethoxy-phenyl)-3-(2-hydroxy-phenyl)-acrylonitrile;

(Z)-2-(3,4-dimethoxy-phenyl)-3-(4-hydroxy-3-methoxyphenyl)-acrylonitrile;

(Z)-3-(3,4-dihydroxy-phenyl)-2-(3,4-dimethoxy-phenyl)-acrylonitrile;

(Z)-2-(3,4-dimethoxy-phenyl)-3-(3-hydroxy-2-methoxyphenyl)-acrylonitrile;

(Z)-2-(3,4-dimethoxy-phenyl)-3-(4-hydroxy-3,5-dimethylphenyl)-acrylonitrile;

(Z)-2-(3,4-dimethoxy-phenyl)-3-(3-ethoxy-4-hydroxy-phenyl)-acrylonitrile;

(Z)-3-(4-bromo-phenyl)-2-(3,4-dimethoxy-phenyl)-acrylonitrile;

(Z)-2-(3,4-dimethoxy-phenyl)-3-(3-fluoro-phenyl)-acrylonitrile;

(Z)-2-(4-butoxy-phenyl)-3-(4-hydroxy-phenyl)-acrylonitrile;

(Z)-3-(4-hydroxy-phenyl)-2-(3,4,5-trimethoxy-phenyl)-acrylonitrile;

(Z)-2,3-bis-(4-hydroxy-phenyl)-acrylonitrile;

(Z)-2-(3,4-dimethoxy-phenyl)-3-(4-hydroxy-phenyl)-acrylonitrile, sodium salt;

(Z)-2-(3,4-dimethoxy-phenyl)-3-(4-fluoro-phenyl)-acrylonitrile;

(Z)-2-(3,4-dimethoxy-phenyl)-3-(4-nitro-phenyl)-acrylonitrile;

(Z)-2-(3,4-dimethoxy-phenyl)-3-(2-fluoro-phenyl)-acrylonitrile;

4-[(Z)-2-cyano-2-(3,4-dimethoxy-phenyl)-vinyl]-benzonitrile;

(Z)-3-(2,3-difluoro-phenyl)-2-(3,4-dimethoxy-phenyl)-acrylonitrile;

(Z)-3-(2,4-difluoro-phenyl)-2-(3,4-dimethoxy-phenyl)-acrylonitrile;

(Z)-3-(2,5-difluoro-phenyl)-2-(3,4-dimethoxy-phenyl)-acrylonitrile;

(Z)-3-(3,4-difluoro-phenyl)-2-(3,4-dimethoxy-phenyl)-acrylonitrile;

(Z)-3-(3,5-difluoro-phenyl)-2-(3,4-dimethoxy-phenyl)-acrylonitrile;

(Z)-2-(3,4-dimethoxy-phenyl)-3-(2,3,4-trifluoro-phenyl)-acrylonitrile;

(Z)-2-(3,4-dimethoxy-phenyl)-3-(2,3,5-trifluoro-phenyl)-acrylonitrile;

(Z)-2-(3,4-dimethoxy-phenyl)-3-(2,3,6-trifluoro-phenyl)-acrylonitrile;
(Z)-2-(3,4-dimethoxy-phenyl)-3-(2,4,5-trifluoro-phenyl)-acrylonitrile;
(Z)-2-(3,4-dimethoxy-phenyl)-3-(3,4,5-trifluoro-phenyl)-acrylonitrile;
(Z)-3-(2,6-difluoro-phenyl)-2-(3,4-dimethoxy-phenyl)-acrylonitrile;
(Z)-2-(3,4-dimethoxy-phenyl)-3-(3-nitro-phenyl)-acrylonitrile;
(Z)-3-(4-amino-phenyl)-2-(3,4-dimethoxy-phenyl)-acrylonitrile;
ethyl [4-[(Z)-2-cyano-2-(3,4-dimethoxy-phenyl)-vinyl]-phenoxy]-acetate;
methyl 4-[(Z)-2-cyano-2-(3,4-dimethoxy-phenyl)-vinyl]-benzoate;
(Z)-2-(3,4-dimethoxy-phenyl)-3-(2-nitro-phenyl)-acrylonitrile;
(Z)-3-(4-chloro-3-nitro-phenyl)-2-(3,4-dimethoxy-phenyl)-acrylonitrile;
(Z)-2-(3,4-dimethoxy-phenyl)-3-(2-fluoro-5-nitro-phenyl)-acrylonitrile;
(Z)-2-(3,4-dimethoxy-phenyl)-3-(4-ethoxy-3-nitro-phenyl)-acrylonitrile;
4-[(Z)-2-cyano-2-(3,4-dimethoxy-phenyl)-vinyl]-phenyl methyl succinate;
4-[(Z)-2-cyano-2-(3,4-dimethoxy-phenyl)-vinyl]-phenyl ethyl succinate;
bis-{4-[(Z)-2-cyano-2-(3,4-dimethoxy-phenyl)-vinyl]-phenyl} succinate;
(Z)-2-(3,4-dimethoxyphenyl)-3-(4-β-D-glucopyranosylphenyl)-acrylonitrile;
(Z)-2-(3,4-dimethoxy-phenyl)-3-(4-hydroxy-3-nitro-phenyl)-acrylonitrile;
(Z)-2-(3,4-dimethoxy-phenyl)-3-(6-nitro-benzo[1,3]dioxol-5-yl)-acrylonitrile;
(Z)-3-(3,4-dimethoxy-phenyl)-2-[4-(2-methoxy-ethoxymethoxy)-phenyl]-acrylonitrile;
(Z)-3-(3,4-dimethoxy-phenyl)-2-(4-hydroxy-phenyl)-acrylonitrile;
(Z)-2-(3,5-bis-trifluoromethyl-phenyl)-3-(4-hydroxy-phenyl)-acrylonitrile;
(E)-2-(3,4-dimethoxy-phenyl)-3-(4-hydroxy-phenyl)-acrylonitrile;
(Z)-2-(3,4-dimethoxyphenyl)-3-(4-β-maltosyl-phenyl)-acrylonitrile;
(Z)-2-(3,4-dimethoxy-phenyl)-3-(2-ethoxy-5-nitro-phenyl)-acrylonitrile;
(Z)-2-(3,4-dimethoxy-phenyl)-3-(3-hydroxy-4-nitro-phenyl)-acrylonitrile;
(Z)-2-(3,4-dimethoxyphenyl)-3-(4-β-maltotriosyl-phenyl)-acrylonitrile;
(Z)-2-(3,4-dimethoxy-phenyl)-3-(3-fluoro-2-hydroxy-phenyl)-acrylonitrile;
(Z)-2,3-bis-(3,4-dimethoxy-phenyl)-acrylonitrile;
(Z)-3-(3-amino-phenyl)-2-(3,4-dimethoxy-phenyl)-acrylonitrile;
(Z)-2-(3,4-dimethoxy-phenyl)-3-[3-fluoro-4-(2-methoxy-ethoxymethoxy)-phenyl]-acrylonitrile;
(Z)-2-(3,4-dimethoxy-phenyl)-3-(3-fluoro-4-hydroxy-phenyl)-acrylonitrile;
mono-{4-[(Z)-2-cyano-2-(3,4-dimethoxy-phenyl)-vinyl]-phenyl} sodium phosphate;
4-[(Z)-1-cyano-2-(3,4-dimethoxy-phenyl)-vinyl]phenyl acetate;
(Z)-2-(3,4-dimethoxy-phenyl)-3-(4-formyl-phenyl)-acrylonitrile;
4-[(Z)-1-cyano-2-(3,4-dimethoxy-phenyl)-vinyl]-2-ethoxyphenyl acetate;
4-[(Z)-1-cyano-2-(3,4-dimethoxy-phenyl)-vinyl]-2-fluorophenyl acetate;
4-[(Z)-2-cyano-2-(3,4,5-trimethoxy-phenyl)-vinyl]-phenyl acetate;
ethyl 7-[4-[(Z)-2-cyano-2-(3,4-dimethoxy-phenyl)-vinyl]-phenoxy]-heptanoate;
4-[(Z)-1-cyano-2-(3,4-dimethoxy-phenyl)-vinyl]-phenyl 8-bromo-octanoate;
(Z)-3-(3-amino-phenyl)-2-(3,4-dimethoxy-phenyl)-acrylonitrile, hydrochloride;
mono-{4-[(Z)-2-cyano-2-(3,4-dimethoxy-phenyl)-vinyl]-2-methoxy-phenyl} sodium phosphate;
mono-{4-[(Z)-2-cyano-2-(3,4-dimethoxy-phenyl)-vinyl]-phenyl} phosphate;
mono-{4-[(Z)-2-cyano-2-(3,4-dimethoxy-phenyl)-vinyl]-2-methoxy-phenyl} phosphate;
N-[3-[2-cyano-2-(3,4-dimethoxy-phenyl)-vinyl]-phenyl]-acetamide;
(Z)-2-(3,4-dimethoxyphenyl)-3-[4-(6-phospho-β-D-glucopyranosyl)-phenyl]-acrylonitrile;
sulphoric acid mono{4-[(Z)-2-cyano-2-(3,4-dimethoxy-phenyl)-vinyl]-phenyl}ester triethylammonium salt;
(Z)-2-(3,4-dimethoxyphenyl)-3-[4-(6-phospho-β-D-glucopyranosyl)-phenyl]-acrylonitrile sodium salt;
(Z)-2-(3,4-dimethoxy-phenyl)-3-(2-hydroxy-5-nitro-phenyl)-acrylonitrile;
(Z)-2-(3,4-dimethoxy-phenyl)-3-(4-fluoro-3-nitro-phenyl)-acrylonitrile;
(Z)-2-(3,4-dimethoxy-phenyl)-3-(3-hydroxy-4,5-dimethoxy-phenyl)-acrylonitrile; and
(Z)-2-(3,4-dimethoxy-phenyl)-3-(4-hydroxy-3,5-dimethoxy-phenyl)-acrylonitrile.

The diphenylacrylonitrile derivatives (1), or salts thereof, of the present invention may, for example, be prepared through the following reaction scheme.

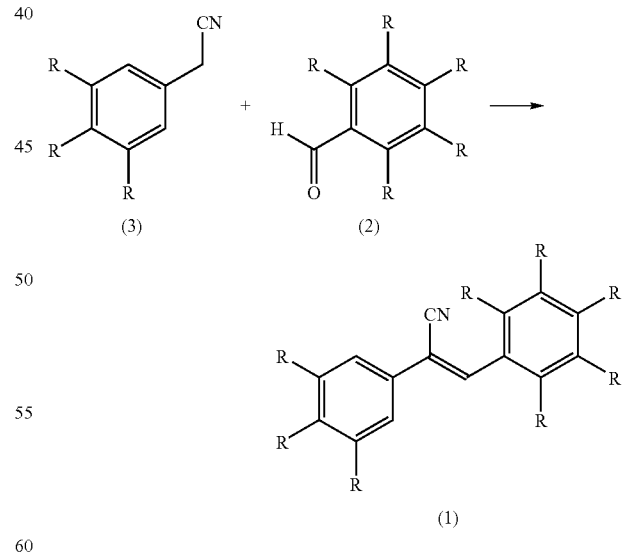

(wherein R has the same meaning as described above).

That is, a benzaldehyde (2) and a benzyl cyanide (3) are subjected to a condensation reaction, to thereby yield a diphenylacrylonitrile derivative (1). However, when the target compound is a diphenylacrylonitrile derivative (1) in which R is a hydroxyl group, an R-protected benzaldehyde (2) and an R-protected benzyl cyanide (3) (wherein the protective group may be, for example, a methoxymethoxy group, a methoxyethoxymethoxy group, a methylthiomethoxy group, a tetrahydropyranyloxy group, a cyclopropylmethoxy group, a benzyloxy group, a trimethylsilyloxy group, or a tert-butyldimethylsilyloxy group) are subjected to a condensation reaction, followed by removal of the protective groups.

The condensation reaction is preferably carried out in the presence of a base such as sodium alkoxide, sodium hydroxide, or potassium hydroxide. When sodium alkoxide is employed, the condensation reaction is performed in an alcoholic solvent, such as methanol or ethanol, at between room temperature and reflux temperature, whereas when sodium hydroxide is employed, the condensation reaction is performed in a solvent mixture of water and an inert solvent, such as methylene chloride or chloroform, with a quaternary ammonium salt or a similar compound being added thereto.

After completion of condensation reaction, the hydroxy-protective group is removed. The removal is preferably achieved by hydrolysis in the presence of, for example, hydrochloric acid, sulfuric acid, acetic acid, p-toluenesulfonic acid, or trifluoroacetic acid. Also, the benzyloxy group is preferably deprotected through catalytic hydrogenation in the presence of a catalyst such as palladium carbon, or platinum oxide.

The diphenylacrylonitrile compound of the present invention may be administered as is. Alternatively, so long as the effects of the present invention are not reduced, the diphenylacrylonitrile compound may be mixed with a carrier which is generally employed for drug preparation, such as a dispersing aid or an excipient, and may be used in the form of an injection or a peroral preparation such as a powder, a solution, a capsule, a suspension, an emulsion, a syrup, an elixir, a granule, a pill, a tablet, a troche, or a lemonade.

Examples of such a carrier include water-soluble monosaccharides, oligosaccharides, and polysaccharides, such as mannitol, lactose, and dextran; gel-forming or water-soluble celluloses, such as hydroxypropyl cellulose, hydroxypropylmethyl cellulose, and methyl cellulose; water-absorbing and poorly water-soluble celluloses, such as crystalline cellulose, α-cellulose, cross-linked carboxymethylcellulose sodium, and derivatives thereof; water-absorbing and poorly water-soluble polysaccharides, such as hydroxypropyl starch, carboxymethyl starch, cross-linked starch, amylose, amylopectin, pectin, and derivatives thereof; water-absorbing and poorly water-soluble gums, such as gum arabi, tragacanth gum, glucomannan, and derivatives thereof; cross-linked vinyl polymers, such as polyvinyl pyrrolidone, cross-linked polyacrylic acid and salts thereof, cross-linked polyvinyl alcohol, polyhydroxyethyl methacrylate, and derivatives thereof; and molecular aggregate (e.g., liposome)-forming lipids, such as phosphorlipid and cholesterol.

When the diphenylacrylonitrile compound of the present invention exhibits low solubility, the compound may be subjected to solubilization. Examples of the solubilization technique include techniques which are generally applicable to drugs, such as a technique in which a surfactant (e.g., a polyoxyethylene alcohol ether, a polyoxyethylene acyl ester, a sorbitan acyl ester, or a polyoxyethylene sorbitan acyl ester) is added to the diphenylacrylonitrile compound, and a technique employing a water-soluble polymer (e.g., polyethylene glycol). If desired, there may be employed, for example, a technique for forming a soluble salt of the diphenylacrylonitrile compound, or a technique for forming a clathrate compound by use of cyclodextrin or a similar material. A solubilization technique may be appropriately selected in accordance with the target diphenylacrylonitrile compound.

The BCRP inhibitor may be employed as an anticancer-drug-resistance-overcoming agent for a cancer which has acquired BCRP-mediated resistance through administration of an anticancer drug. Meanwhile, the BCRP inhibitor may be employed as an anticancer-drug-effect-enhancing agent for a cancer which originally expresses BCRP and exhibits low sensitivity to an anticancer drug. No particular limitations are imposed on the target anticancer drug of an anticancer-drug-resistance-overcoming agent or anticancer-drug-effect-enhancing agent containing the BCRP inhibitor as an active ingredient, so long as the anticancer drug can serve as a substrate for BCRP (hereinafter may be referred to as BCRP substrate). Examples of such an anticancer drug include topoisomerase I inhibitors such as irinotecan hydrochloride/CPT-11 (active metabolite: SN-38) and topotecan; topoisomerase II inhibitors such as mitoxantrone, doxorubicin, daunorubicin, bisanthrene, and etoposide; and antifolates such as methotrexate.

The dose of the BCRP inhibitor of the present invention may be appropriately determined in accordance with, for example, the administration method or the symptom of a patient. The daily dose for an adult is preferably 1 mg to 10 g, more preferably 100 mg to 10 g, particularly preferably 500 mg to 10 g. No particular limitations are imposed on the ratio between an anticancer drug and the BCRP inhibitor, and the preferred ratio varies in accordance with, for example, the type of an anticancer drug or inhibitor to be employed. When, for example, irinotecan hydrochloride is employed as an anticancer drug, the ratio by weight of the anticancer drug to the BCRP inhibitor is preferably 1:1 to 1:500, particularly preferably 1:1 to 1:100, more preferably 1:1 to 1:10.

Table 1 shows some specific examples of diphenylacrylonitrile derivatives which may be employed in the present invention.

TABLE 1

| Compound | Chemical Name |
| --- | --- |
| 1 | (Z)-2-(3,4-dimethoxy-phenyl)-3-(4-hydroxy-phenyl)-acrylonitrile |
| 2 | 4-[(Z)-2-cyano-2-(3,4-dimethoxy-phenyl)-vinyl]-phenyl[1,4']bipiperidinyl-1'-carboxylate |
| 3 | 4-[(Z)-2-cyano-2-(3,4-dimethoxy-phenyl)-vinyl]-phenyl acetate |
| 4 | (Z)-2-(3,4-dimethoxy-phenyl)-3-[4-(2-methoxy-ethoxymethoxy)-phenyl]-acrylonitrile |
| 5 | (Z)-2-(3,4-dimethoxy-phenyl)-3-(3-hydroxy-phenyl)-acrylonitrile |
| 6 | (Z)-2-(3,4-dimethoxy-phenyl)-3-(2-hydroxy-phenyl)-acrylonitrile |
| 7 | (Z)-2-(3,4-dimethoxy-phenyl)-3-(4-hydroxy-3-methoxy-phenyl)-acrylonitrile |
| 8 | (Z)-3-(3,4-dihydroxy-phenyl)-2-(3,4-dimethoxy-phenyl)-acrylonitrile |
| 9 | (Z)-2-(3,4-dimethoxy-phenyl)-3-(3-hydroxy-2-methoxy-phenyl)-acrylonitrile |
| 10 | (Z)-2-(3,4-dimethoxy-phenyl)-3-(4-hydroxy-3,5-dimethyl-phenyl)-acrylonitrile |
| 11 | (Z)-2-(3,4-dimethoxy-phenyl)-3-(3-ethoxy-4-hydroxy-phenyl)-acrylonitrile |
| 12 | (Z)-3-(4-bromo-phenyl)-2-(3,4-dimethoxy-phenyl)-acrylonitrile |
| 13 | (Z)-2-(3,4-dimethoxy-phenyl)-3-(3-fluoro-phenyl)-acrylonitrile |
| 14 | (Z)-2-(4-butoxy-phenyl)-3-(4-hydroxy-phenyl)-acrylonitrile |

TABLE 1-continued

| Compound | Chemical Name |
|---|---|
| 15 | (Z)-3-(4-hydroxy-phenyl)-2-(3,4,5-trimethoxy-phenyl)-acrylonitrile |
| 16 | (Z)-2,3-bis-(4-hydroxy-phenyl)-acrylonitrile |
| 17 | (Z)-2-(3,4-dimethoxy-phenyl)-3-(4-hydroxy-phenyl)-acrylonitrile sodium salt |
| 18 | (Z)-2-(3,4-dimethoxy-phenyl)-3-(4-fluoro-phenyl)-acrylonitrile |
| 19 | (Z)-2-(3,4-dimethoxy-phenyl)-3-(4-nitro-phenyl)-acrylonitrile |
| 20 | (Z)-2-(3,4-dimethoxy-phenyl)-3-(2-fluoro-phenyl)-acrylonitrile |
| 21 | 4-[(Z)-2-cyano-2-(3,4-dimethoxy-phenyl)-vinyl]-benzonitrile |
| 22 | (Z)-3-(2,3-difluoro-phenyl)-2-(3,4-dimethoxy-phenyl)-acrylonitrile |
| 23 | (Z)-3-(2,4-difluoro-phenyl)-2-(3,4-dimethoxy-phenyl)-acrylonitrile |
| 24 | (Z)-3-(2,5-difluoro-phenyl)-2-(3,4-dimethoxy-phenyl)-acrylonitrile |
| 25 | (Z)-3-(3,4-difluoro-phenyl)-2-(3,4-dimethoxy-phenyl)-acrylonitrile |
| 26 | (Z)-3-(3,5-difluoro-phenyl)-2-(3,4-dimethoxy-phenyl)-acrylonitrile |
| 27 | (Z)-2-(3,4-dimethoxy-phenyl)-3-(2,3,4-trifluoro-phenyl)-acrylonitrile |
| 28 | (Z)-2-(3,4-dimethoxy-phenyl)-3-(2,3,5-trifluoro-phenyl)-acrylonitrile |
| 29 | (Z)-2-(3,4-dimethoxy-phenyl)-3-(2,3,6-trifluoro-phenyl)-acrylonitrile |
| 30 | (Z)-2-(3,4-dimethoxy-phenyl)-3-(2,4,5-trifluoro-phenyl)-acrylonitrile |
| 31 | (Z)-2-(3,4-dimethoxy-phenyl)-3-(3,4,5-trifluoro-phenyl)-acrylonitrile |
| 32 | (Z)-3-(2,6-difluoro-phenyl)-2-(3,4-dimethoxy-phenyl)-acrylonitrile |
| 33 | (Z)-2-(3,4-dimethoxy-phenyl)-3-(3-nitro-phenyl)-acrylonitrile |
| 34 | (Z)-3-(4-amino-phenyl)-2-(3,4-dimethoxy-phenyl)-acrylonitrile |
| 35 | ethyl[4-[(Z)-2-cyano-2-(3,4-dimethoxy-phenyl)-vinyl]-phenoxy]-acetate |
| 36 | methyl 4-[(Z)-2-cyano-2-(3,4-dimethoxy-phenyl)-vinyl]-benzoate |
| 37 | (Z)-2-(3,4-dimethoxy-phenyl)-3-(2-nitro-phenyl)-acrylonitrile |
| 38 | (Z)-3-(4-chloro-3-nitro-phenyl)-2-(3,4-dimethoxy-phenyl)-acrylonitrile |
| 39 | (Z)-2-(3,4-dimethoxy-phenyl)-3-(2-fluoro-5-nitro-phenyl)-acrylonitrile |
| 40 | (Z)-2(3,4-dimethoxy-phenyl)-3-(4-ethoxy-3-nitro-phenyl)-acrylonitrile |
| 41 | 4-[(Z)-2-cyano-2-(3,4-dimethoxy-phenyl)-vinyl]-phenyl methyl succinate |
| 42 | 4-[(Z)-2-cyano-2-(3,4-dimethoxy-phenyl)-vinyl]-phenyl ethyl succinate |
| 43 | bis-(4-[(Z)-2-cyano-2-(3,4-dimethoxy-phenyl)-vinyl]-phenyl) succinate |
| 44 | (Z)-2-(3,4-dimethoxy-phenyl)-3-(4-β-D-glucopyranosylphenyl)-acrylonitrile |
| 45 | (Z)-2-(3,4-dimethoxy-phenyl)-3-(4-hydroxy-3-nitro-phenyl)-acrylonitrile |
| 46 | (Z)-2-(3,4-dimethoxy-phenyl)-3-(6-nitro-benzo[1,3]dioxol-5-yl)-acrylonitrile |
| 47 | (Z)-3-(3,4-dimethoxy-phenyl)-2-[4-(2-methoxy-ethoxymethoxy)-phenyl]-acrylonitrile |
| 48 | (Z)-3-(3,4-dimethoxy-phenyl)-2-(4-hydroxy-phenyl)-acrylonitrile |
| 49 | (Z)-2-(3,5-bis-trifluoromethyl-phenyl)-3-(4-hydroxy-phenyl)-acrylonitrile |
| 50 | (E)-2-(3,4-dimethoxy-phenyl)-3-(4-hydroxy-phenyl)-acrylonitrile |
| 51 | (Z)-2-(3,4-dimethoxyphenyl)-3-(4-β-maltosyl-phenyl)-acrylonitrile |
| 52 | (Z)-2-(3,4-dimethoxy-phenyl)-3-(2-ethoxy-5-nitro-phenyl)-acrylonitrile |
| 53 | (Z)-2-(3,4-dimethoxy-phenyl)-3-(3-hydroxy-4-nitro-phenyl)-acrylonitrile |
| 54 | (Z)-2-(3,4-dimethoxyphenyl)-3-(4-β-maltotriosyl-phenyl)-acrylonitrile |
| 55 | (Z)-2-(3,4-dimethoxy-phenyl)-3-(3-fluoro-2-hydroxy-phenyl)-acrylonitrile |
| 56 | (Z)-2,3-bis-(3,4-dimethoxy-phenyl)-acrylonitrile |
| 57 | (Z)-3-(3-amino-phenyl)-2-(3,4-dimethoxy-phenyl)-acrylonitrile |
| 58 | (Z)-2-(3,4-dimethoxy-phenyl)-3-[3-fluoro-4-(2-methoxy-ethoxymethoxy)-phenyl]-acrylonitrile |
| 59 | (Z)-2-(3,4-dimethoxy-phenyl)-3-(3-fluoro-4-hydroxy-phenyl)-acrylonitrile |
| 60 | Sodium mono(4-[(Z)-2-cyano-2-(3,4-dimethoxy-phenyl)-vinyl]-phenyl) phosphate |
| 61 | 4-[(Z)-1-cyano-2-(3,4-dimethoxy-phenyl)-vinyl]-phenyl acetate |
| 62 | (Z)-2-(3,4-dimethoxy-phenyl)-3-(4-formyl-phenyl)-acrylonitrile |
| 63 | 4-[(Z)-1-cyano-2-(3,4-dimethoxy-phenyl)-vinyl]-2-ethoxy-phenyl acetate |
| 64 | 4-[(Z)-1-cyano-2-(3,4-dimethoxy-phenyl)-vinyl]-2-fluoro-phenyl acetate |
| 65 | 4-[(Z)-2-cyano-2-(3,4,5-trimethoxy-phenyl)-vinyl]-phenyl acetate |
| 66 | ethyl 7-[4-[(Z)-2-cyano-2-(3,4-dimethoxy-phenyl)-vinyl]-phenoxy]-heptanoate |
| 67 | 4-[(Z)-1-cyano-2-(3,4-dimethoxy-phenyl)-vinyl]-phenyl 8-bromo-octanoate |
| 68 | (Z)-3-(3-amino-phenyl)-2-(3,4-dimethoxy-phenyl)-acrylonitrile hydrochloride |
| 69 | mono(4-[(Z)-2-cyano-2-(3,4-dimethoxy-phenyl)-vinyl]-2-methoxy-phenyl) sodium phosphate |
| 70 | mono(4-[(Z)-2-cyano-2-(3,4-dimethoxy-phenyl)-vinyl]-phenyl) phosphate |
| 71 | mono(4-[(Z)-2-cyano-2-(3,4-dimethoxy-phenyl)-vinyl]-2-methoxy-phenyl) phosphate |
| 72 | N-[3-[(Z)-2-cyano-2-(3,4-dimethoxy-phenyl)-vinyl]-phenyl]-acetamide |
| 73 | (Z)-2-(3,4-dimethoxy-phenyl)-3-[4-(6-phospho-β-D-glucopyranosyl)-phenyl]-acrylonitrile |
| 74 | sulphoric acid mono(4-[(Z)-2-cyano-2-(3,4-dimethoxy-phenyl)-vinyl]-phenyl) ester triethylammonium salt |
| 75 | (Z)-2-(3,4-dimethoxy-phenyl)-3-[4-(6-phospho-β-D-glucopyranosyl)-phenyl]-acrylonitrile sodium salt |
| 76 | (Z)-2-(3,4-dimethoxy-phenyl)-3-(2-hydroxy-5-nitro-phenyl)-acrylonitrile |
| 77 | (Z)-2-(3,4-dimethoxy-phenyl)-3-(4-fluoro-3-nitro-phenyl)-acrylonitrile |
| 78 | (Z)-2-(3,4-dimethoxy-phenyl)-3-(3-hydroxy-4,5-dimethoxy-phenyl)-acrylonitrile |
| 79 | (Z)-2-(3,4-dimethoxy-phenyl)-3-(4-hydroxy-3,5-dimethoxy-phenyl)-acrylonitrile |

EXAMPLES

The present invention will next be described in more detail by way of Examples, which should not be construed as limiting the invention thereto.

Example 1

Production of Diphenylacrylonitrile Derivative

When a diphenylacrylonitrile derivative was synthesized from a raw material having a hydroxyl group (a benzaldehyde derivative or a benzyl cyanide derivative), firstly, the hydroxyl group was protected through the below-described protection process; subsequently, the resultant product was subjected to a condensation process; and finally, the protective group was removed through a deprotection process. When a raw material having no hydroxyl group was employed, the raw material was subjected to the condensation process without being subjected to the protection process.

(Production process 1) Process for Protecting Hydroxyl Group of a Benzaldehyde Derivative or Benzyl Cyanide Derivative

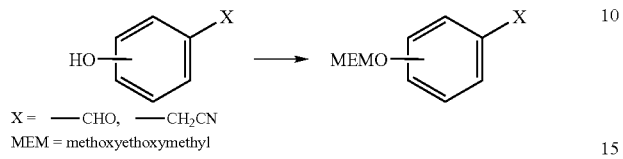

X = —CHO, —CH₂CN
MEM = methoxyethoxymethyl

In a reaction vessel, a benzaldehyde derivative or benzyl cyanide derivative having a hydroxyl group was dissolved in tetrahydrofuran under stirring. The reaction vessel was ice-cooled, and sodium hydride (content: 60%, suspended in oil) was gradually added in an amount depending on the hydroxyl group number (e.g., 1.2 equivalents (OH-basis) for the case where the hydroxyl group number is one, or 2.4 equivalents for the case where the hydroxyl group number is two). Thereafter, a calcium chloride tube was provided on the reaction vessel. After completion of generation of hydrogen, 2-methoxyethoxymethyl chloride was added in an amount depending on the hydroxyl group number (e.g., 1 equivalent (OH-basis) for the case where the hydroxyl group number is one, or 2 equivalents for the case where the hydroxyl group number is two). Subsequently, diisopropylamine was added in an amount stoichiometrically equivalent to that of the added 2-methoxyethoxymethyl chloride. The resultant mixture was refluxed under heating for two hours, with a calcium chloride tube being provided on the reaction vessel. After the resultant product was cooled, insoluble matter was removed through filtration. The resultant tetrahydrofuran solution was concentrated to dryness under reduced pressure. The thus-concentrated product was partitioned between chloroform and brine. An aqueous sodium hydroxide solution was added to the thus-obtained chloroform layer, and the resultant mixture was partitioned. The resultant chloroform layer was washed with water twice. The chloroform layer was dried over anhydrous sodium sulfate, and then concentrated to dryness under reduced pressure. By means of silica gel column chromatography, the thus-concentrated product was subjected to elution with hexane/chloroform to chloroform. The thus-obtained fraction was concentrated, to thereby yield an oily product.

(Production process 2) Process of Condensation Between a Benzaldehyde Derivative and a Benzyl Cyanide Derivative

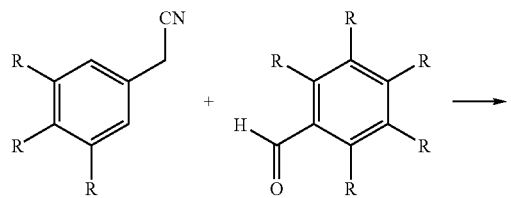

-continued

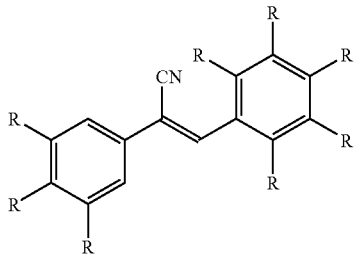

Process A: A benzaldehyde derivative and a benzyl cyanide derivative, in stoichiometrically equivalent amounts, were placed in a reaction vessel, and ethanol was added to the container. Subsequently, a calcium chloride tube was provided on the container, and the derivatives were dissolved in the ethanol under stirring. Separately, metallic sodium was weighed in a container containing n-hexane, the sodium was gradually added to a container containing ethanol, and a calcium chloride tube was provided on the container. After the sodium was completely dissolved in the ethanol, the resultant sodium ethoxide solution was added to the aforementioned reaction vessel. The reaction mixture was refluxed for about one hour. Thereafter, the reaction mixture was cooled to room temperature, and water was added to the mixture, followed by removal of ethanol through evaporation under reduced pressure. The resultant residue was partitioned between chloroform and brine. Brine was added to the thus-separated chloroform layer, and the resultant mixture was partitioned. The thus-separated chloroform layer was dried over anhydrous sodium sulfate, followed by filtration. A small amount of silica gel for column chromatography was added to the resultant filtrate, followed by shaking and filtration. The solvent was removed through evaporation under reduced pressure. The resultant product was dissolved in ethanol, and an appropriate amount of activated carbon was added to the resultant solution. The resultant mixture was subjected to filtration by use of a celite pad, and the filtrate was concentrated. The thus-precipitated crystals of a diphenylacrylonitrile derivative were subjected to filtration under reduced pressure. This procedure was performed three times, and the resultant crystals were separated. The thus-precipitated crystals were recrystallized from isopropanol twice. The resultant crystals were washed with hexane, and then dried.

Process B: A benzaldehyde derivative and a benzyl cyanide derivative, in stoichiometrically equivalent amounts, were placed in a reaction vessel, and these derivatives were dissolved in methylene chloride. An aqueous solution (10 to 20 mL) of sodium hydroxide (1.2 eq.) was added to the resultant solution, along with methyltrioctylammonium chloride (1/5 eq.), followed by stirring at room temperature for four hours. After completion of reaction, the resultant reaction mixture was dried over anhydrous sodium sulfate, and then subjected to filtration, followed by concentration of the filtrate. The resultant residue was recrystallized from isopropanol.

(Production Process 3) Process for Deprotecting an OH-protected Diphenylacrylonitrile Derivative

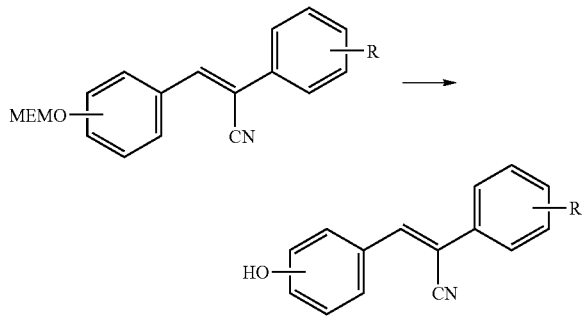

A diphenylacrylonitrile derivative having a protected hydroxyl group was dissolved in ethanol, and a small amount of concentrated hydrochloric acid was added to the resultant solution, followed by stirring for a whole day and night. The thus-precipitated crystals were separated under reduced pressure. The resultant crystals were recrystallized from isopropanol.

Next will be specifically described production of diphenylacrylonitrile derivatives and the results of analysis thereof.

Production of (Z)-2-(3,4-dimethoxyphenyl)-3-(4-hydroxyphenyl)acrylonitrile (Compound 1)

The hydroxyl group of 4-hydroxybenzaldehyde (24.9 g) was protected by use of 2-methoxyethoxymethyl chloride (24.4 g) in accordance with (production process 1), to thereby produce 4-methoxyethoxymethoxybenzaldehyde (33.5 g, yield: 80%). The thus-produced 4-methoxyethoxymethoxybenzaldehyde (21.0 g) and 3,4-dimethoxybenzyl cyanide (17.7 g) were subjected to condensation in accordance with process A of (production process 2), to thereby produce (Z)-2-(3,4-dimethoxyphenyl)-3-[4-(2-methoxy-ethoxymethoxy)-phenyl]acrylonitrile (29.1 g, yield: 86%). Separately, 2-methoxyethoxymethyl chloride (4.1 g), which had been prepared in a manner similar to that described above, and 3,4-dimethoxybenzyl cyanide (3.4 g) were subjected to condensation in accordance with process B of (production process 2), to thereby produce (Z)-2-(3,4-dimethoxy-phenyl)-3-[4-(2-methoxy-ethoxymethoxy)-phenyl]acrylonitrile (5.2 g, yield: 73%). The thus-produced (Z)-2-(3,4-dimethoxy-phenyl)-3-[4-(2-methoxy-ethoxymethoxy)-phenyl]-acrylonitrile (10.2 g) was subjected to deprotection in accordance with (production process 3), to thereby produce the target product (6.22 g, yield: 74%).

Pale yellow crystalline powder, MS (APCI, m/z): 282 (MH+), $^1$H-NMR (DMSO-d6) δ 3.80 (3H, s), 3.85 (3H, s), 6.89(2H, d, J=9 Hz), 7.05 (1H, d, J=9 Hz), 7.20(1H, dd, J=2 Hz, 9 Hz), 7.27(1H, d, J=2 Hz), 7.80(1H, s), 7.82(2H, d, J=9 Hz)

Production of 4-[(Z)-2-cyano-2-(3,4-dimethoxy-phenyl)-vinyl]-phenyl [1,4']bipiperidinyl-1'-carboxylate (Compound 2)

(Z)-2-(3,4-dimethoxyphenyl)-3-(4-hydroxyphenyl)acrylonitrile (compound 1) (0.28 g) and 4-piperidinopiperidinocarbonyl chloride (0.23 g) were dissolved in pyridine (5 ml), and the resultant solution was stirred for a whole day and night. After completion of reaction, the resultant reaction mixture was added to water (200 ml), and the thus-precipitated product was purified by means of silica gel chromatography employing a chloroform/methanol system, to thereby produce the target product (0.38 g, yield: 79%).

Pale yellow crystals, MS (APCI, m/z): 476 (MH+), $^1$H-NMR (DMSO-d6) δ 1.47(3H, m), 1.75(2H, m), 2.49(5H, m), 2.85(1H, br.t), 3.01(1H, br.t), 3.71 (1H, m), 3.79 (3H, s), 3.84 (3H, s), 4.03(1H, br.d), 4.17(1H, br.d), 6.89(2H, d, J=9 Hz), 7.07 (1H, d, J=8 Hz), 7.26(1H, dd, J=2 Hz, 8 Hz), 7.27(2H, d, J=8 Hz), 7.33(1H, d, J=2 Hz), 7.91(2H, d, J=8 Hz), 7.95(1H, s)

Production of 4-[(Z)-2-cyano-2-(3,4-dimethoxyphenyl)-vinyl]-phenyl acetate (Compound 3)

Compound 1 (0.28 g) was acetylated with acetic anhydride and pyridine in accordance with a customary method, to thereby produce the target product (0.30 g, yield: 95%).

White crystals, MS (APCI, m/z): 324 (MH+), $^1$H-NMR (CDCl$_3$) δ2.33(3H, s), 3.93 (3H, s), 3.96 (3H, s), 6.92(2H, d, J=9 Hz), 7.14 (1H, d, J=9 Hz), 7.20(1H, d, J=2 Hz), 7.25(1H, dd, J=2 Hz, 9 Hz), 7.40(1H, s), 7.89(2H, d, J=9 Hz)

Production of (Z)-2-(3,4-dimethoxy-phenyl)-3-[4-(2-methoxy-ethoxymethoxy)-phenyl]-acrylonitrile (Compound 4)

The title compound was produced in the condensation process for production of compound 1.

Pale yellow crystals, MS (APCI, m/z): 370 (MH+), $^1$H-NMR (DMSO-d6) δ 3.40(3H, s), 3.56 (2H, t, J=8 Hz), 3.84 (2H, t, J=8 Hz), 3.88 (3H, s), 3.92 (3H, s), 5.35(2H, s), 6.87(2H, d, J=9 Hz), 7.14 (1H, d, J=8 Hz), 7.28(1H, dd, J=2 Hz, 8 Hz), 7.29(2H, d, J=8 Hz), 7.40(1H, d, J=2 Hz), 7.92(2H, d, J=8 Hz), 7.99(1H, s)

Production of (Z)-2-(3,4-dimetoxy-phenyl)-3-(3-hydroxy-phenyl)-acrylonitrile (Compound 5)

The hydroxyl group of 3-hydroxybenzaldehyde (1.5 g) was protected by use of 2-methoxyethoxymethyl chloride (1.4 g) in accordance with (production process 1), to thereby produce 3-methoxyethoxymethoxybenzaldehyde (2.0 g, yield: 76%). The thus-produced 3-methoxyethoxymethoxybenzaldehyde (1.9 g) and 3,4-dimethoxybenzyl cyanide (1.6 g) were subjected to condensation in accordance with process A of (production process 2), to thereby yield a methoxyethoxymethoxy form (hereinafter will be referred to as an "MEM form") of the target product. Subsequently, the protective group was removed from the MEM form in accordance with (production process 3), to thereby produce the target product (1.2 g, yield: 48%).

Pale yellow crystalline powder, MS (APCI, m/z): 282 (MH+), $^1$H-NMR (DMSO-d6) δ3.82 (3H, s), 3.87 (3H, s), 5.35 (2H, s), 6.89 (1H, dd, J=8 Hz, 3 Hz), 7.07 (1H, d, J=8 Hz), 7.25-7.37(5H, overlapping m), 7.87(1H, s)

Production of (Z)-2-(3,4-dimethoxy-phenyl)-3-(2-hydroxy-phenyl)-acrylonitrile (Compound 6)

The hydroxyl group of 2-hydroxybenzaldehyde (3.0 g) was protected by use of 2-methoxyethoxymethyl chloride (3.1 g) in accordance with (production process 1), to thereby produce 2-methoxyethoxymethoxybenzaldehyde (3.7 g, yield: 70%). The thus-produced 2-methoxyethoxymethoxybenzaldehyde (2.0 g) and 3,4-dimethoxybenzyl cyanide (1.7 g) were subjected to condensation in accordance with process A of (production process 2), to thereby yield an MEM form of the target product. Subsequently, the protective group was removed from the MEM form in accordance with (production process 3), to thereby produce the target product (1.4 g, yield: 52%).

Pale yellow crystalline powder, MS (APCI, m/z): 282 (MH$^+$), $^1$H-NMR (DMSO-d6) δ 3.81(3H, s), 3.85(3H, s), 7.87(1H, dd, J=8 Hz, 1 Hz), 7.92(1H, Br.s), 6.93(1H, dt, J=7 Hz, 1 Hz), 6.97(1H, dd, J=7 Hz, 1 Hz), 7.07(1H, d, J=8 Hz), 7.22(1H, d, J=2 Hz), 7.31(1H, dt, J=7 Hz, 1 Hz), 7.87(1H, dd, J=8 Hz, 2 Hz), 7.93(1H, s)

Production of (Z)-2-(3,4-dimethoxy-phenyl)-3-(4-hydroxy-3-methoxy-phenyl)-acrylonitrile (Compound 7)

The hydroxyl group of 4-hydroxy-3-methoxybenzaldehyde (1.4 g) was protected by use of 2-methoxyethoxymethyl chloride (1.7 g) in accordance with (production process 1), to thereby produce 3-methoxy-4-methoxyethoxymethoxybenzaldehyde (0.8 g, yield: 31%). The thus-produced 3-methoxy-4-methoxyethoxymethoxybenzaldehyde (0.8 g) and 3,4-dimethoxybenzyl cyanide (0.6 g) were subjected to condensation in accordance with process A of (production process 2), to thereby yield an MEM form of the target product. Subsequently, the protective group was removed from the MEM form in accordance with (production process 3), to thereby produce the target product (0.5 g, yield: 51%).

Pale yellow crystals, MS (APCI, m/z): 312 (MH$^+$), $^1$H-NMR (CDCl$_3$) δ 3.92(3H, s), 3.96 (3H, s), 3.99 (3H, s), 5.94(1H, s), 6.90(1H, d, J=8 Hz), 6.96(2H, d, J=8 Hz), 7.12 (1H, s), 7.22(2H, overlapping m), 7.33(1H, s), 7.73(1H, s)

Production of (Z)-3-(3,4-dihydroxy-phenyl)-2-(3,4-dimethoxy-phenyl)-acrylonitrile (Compound 8)

The hydroxyl groups of 3,4-dihydroxybenzaldehyde (2.0 g) were protected by use of 2-methoxyethoxymethyl chloride (3.6 g) in accordance with (production process 1), to thereby produce 3,4-bis(methoxyethoxymethoxy)benzaldehyde (3.6 g, yield: 89%). The thus-produced 3,4-bis(methoxyethoxymethoxy)benzaldehyde (3.5 g) and 3,4-dimethoxybenzyl cyanide (2.0 g) were subjected to condensation in accordance with process A of (production process 2), to thereby yield an MEM form of the target product. Subsequently, the protective group was removed from the MEM form in accordance with (production process 3), to thereby produce the target product (1.6 g, yield: 50%).

Yellow crystals, MS (APCI, m/z): 298 (MH$^+$), $^1$H-NMR (DMSO-d6) δ 3.85 (3H, s), 3.92 (3H, s), 6.85(1H, d, J=8 Hz), 6.94(2H, d, J=8 Hz), 7.22 (3H, m), 7.48(1H, d, J=2 Hz), 7.49(1H, s), 7.70(1H, s), 9.33(1H, s), 7.69(1H, s)

Production of (Z)-2-(3,4-dimethoxy-phenyl)-3-(3-hydroxy-2-methoxy-phenyl)-acrylonitrile (Compound 9)

The hydroxyl group of 2-methoxy-3-hydroxybenzaldehyde (2.0 g) was protected by use of 2-methoxyethoxymethyl chloride (3.6 g) in accordance with (production process 1), to thereby produce 2,4-bis(methoxyethoxymethoxy)benzaldehyde (4.5 g: quantitative yield). The thus-produced 2,4-bis(methoxyethoxymethoxy)benzaldehyde (4.0 g) and 3,4-dimethoxybenzyl cyanide (2.2 g) were subjected to condensation in accordance with process A of (production process 2), to thereby yield an MEM form of the target product. Subsequently, the protective group was removed from the MEM form in accordance with (production process 3), to thereby produce the target product (2.5 g, yield: 67%).

Yellow crystals, MS (APCI, m/z): 312 (MH$^+$), $^1$H-NMR (DMSO-d6) δ 3.32(3H, s), 3.80 (3H, s), 3.84 (3H, s), 7.05(2H, m), 7.24 (1H, dd, J=2 Hz, 8 Hz), 7.28 (1H, d, J=2 Hz), 7.38(1H, dd, J=2 Hz, 8 Hz), 7.49(1H, s), 7.76(1H, s), 9.36(2H, br.s)

Production of (Z)-2-(3,4-dimethoxy-phenyl)-3-(4-hydroxy-3,5-dimethyl-phenyl)-acrylonitrile (Compound 10)

The hydroxyl group of 3,5-dimethyl-4-hydroxybenzaldehyde (2.3 g) was protected by use of 2-methoxyethoxymethyl chloride (3.4 g) in accordance with (production process 1), to thereby produce 3,5-dimethyl-4-methoxyethoxymethoxybenzaldehyde (2.7 g, yield: 62%). The thus-produced 3,5-dimethyl-4-methoxyethoxymethoxybenzaldehyde (2.0 g) and 3,4-dimethoxybenzyl cyanide (1.5 g) were subjected to condensation in accordance with process A of (production process 2), to thereby yield an MEM form of the target product. Subsequently, the protective group was removed from the MEM form in accordance with (production process 3), to thereby produce the target product (1.5 g, yield: 57%).

Pale yellow crystals, MS (APCI, m/z): 310 (MH$^+$), $^1$H-NMR (CDCl$_3$) δ 2.30(6H, s), 3.92 (3H, s), 3.95 (3H, s), 6.89(2H, d, J=8 Hz), 7.12 (1H, s), 7.20(1H, dd, J=2 Hz, 8 Hz), 7.27(1H, d, J=8 Hz), 7.56(2H, s)

Production of (Z)-2-(3,4-dimethoxy-phenyl)-3-(3-ethoxy-4-hydroxy-phenyl)-acrylonitrile (Compound 11)

The hydroxyl group of 3-ethoxy-4-hydroxybenzaldehyde (2.0 g) was protected by use of 2-methoxyethoxymethyl chloride (1.5 g) in accordance with (production process 1), to thereby produce 3-ethoxy-4-methoxyethoxymethoxybenzaldehyde (2.8 g, yield: 91%). The thus-produced 3-ethoxy-4-methoxyethoxymethoxybenzaldehyde (2.8 g) and 3,4-dimethoxybenzyl cyanide (2.0 g) were subjected to condensation in accordance with process A of (production process 2), to thereby yield an MEM form of the target product. Subsequently, the protective group was removed from the MEM form in accordance with (production process 3), to thereby produce the target product (1.35 g, yield: 37%).

Pale yellow crystals, MS (APCI, m/z): 326 (MH$^+$), $^1$H-NMR (CDCl$_3$) δ 1.49(3H, t, J=8 Hz), 3.92 (3H, s), 3.95 (3H, s), 4.22(2H, d, J=8 Hz), 6.90(2H, dd, J=2 Hz, 8 Hz), 6.96(2H, d, J=8 Hz), 7.11 (1H, d, J=2 Hz), 7.22(1H, dd, J=2 Hz, 8 Hz), 7.32(1H, s), 7.72(2H, d, J=2 Hz)

Production of (Z)-3-(4-bromo-phenyl)-2-(3,4-dimethoxy-phenyl)-acrylonitrile (Compound 12)

4-Bromobenzaldehyde (2.0 g) and 3,4-dimethoxybenzyl cyanide (1.9 g) were subjected to condensation in accordance with process A of (production process 2), to thereby produce the target product (2.9 g, yield: 78%).

Yellow crystals, MS (APCI, m/z): 346 (MH$^+$+2), 344 (MH$^+$)

$^1$H-NMR (CDCl$_3$) δ 3.93 (3H, s), 3.96 (3H, s), 6.92(2H, d, J=9 Hz), 7.26 (2H, overlapping m), 7.35(1H, s), 7.59(2H, d, J=9 Hz), 7.73(2H, d, J=9 Hz)

Production of (Z)-2-(3,4-dimethoxy-phenyl)-3-(3-fluoro-phenyl)-acrylonitrile (Compound 13)

3-Fluorobenzaldehyde (2.0 g) and 3,4-dimethoxybenzyl cyanide (2.9 g) were subjected to condensation in accordance with process A of (production process 2), to thereby produce the target product (0.7 g, yield: 15%).

Pale yellow crystals, MS (APCI, m/z): 284 (MH$^+$), $^1$H-NMR (CDCl$_3$) δ 3.93 (3H, s), 3.96 (3H, s), 6.92(1H, d, J=10 Hz), 7.11 (1H, dd, J=2 Hz, 14 Hz), 7.24(1H, d, J=2 Hz), 7.27(1H, dd, J=2 Hz, 10 Hz), 7.38(1H, s), 7.42(1H, dd, J=8 Hz, 14 Hz), 7.60(1H, dd, J=8 Hz, 14 Hz)

Production of (Z)-2-(4-butoxy-phenyl)-3-(4-hydroxy-phenyl)-acrylonitrile (Compound 14)

4-Hydroxybenzyl cyanide (5.0 g) and 1-bromobutane (5.7 g) were dissolved in dimethylformamide (100 mL), and potassium carbonate (6.2 g) was added to the resultant solution, followed by heating at 80° C. for one hour, to thereby allow reaction to proceed. After completion of reaction, the resultant reaction mixture was cooled, and then partitioned between brine and ethyl acetate. The resultant ethyl acetate layer was dried over anhydrous sodium sulfate, and concentrated. The thus-concentrated product was purified by use of a silica gel column employing hexane/ethyl acetate (4:1), to thereby produce 4-butoxybenzyl cyanide (5.1 g, yield: 70%). The thus-produced 4-butoxybenzyl cyanide (2.0 g) and the 4-methoxyethoxymethoxybenzaldehyde (2.2 g) produced in the production process for compound 1 were subjected to condensation in accordance with process A of (production process 2), to thereby yield an MEM form of the target product. Subsequently, the protective group was removed from the MEM form in accordance with (production process 3), to thereby produce the target product (0.7 g, yield: 23%).

Pale yellow crystalline powder, MS (APCI, m/z): 294 (MH$^+$), $^1$H-NMR (DMSO-d6) δ 0.94 (3H, t, J=10 Hz), 1.44(2H, sextet, J=10 Hz), 1.71(2H, quintet, J=10 Hz), 4.00(2H, t, J=10 Hz), 6.88(2H, d, J=9 Hz), 7.03 (2H, d, J=9 Hz), 7.62(2H, d, J=2 Hz), 7.73(1H, s), 7.82(2H, d, J=9 Hz)

Production of (Z)-3-(4-hydroxy-phenyl)-2-(3,4,5-trimethoxy-phenyl)-acrylonitrile (Compound 15)

3,4,5-Trimethoxybenzyl cyanide (1.9 g) and the 4-methoxyethoxymethoxybenzaldehyde (2.0 g) produced in the production process for compound 1 were subjected to condensation in accordance with process A of (production process 2), to thereby yield an MEM form of the target product. Subsequently, the protective group was removed from the MEM form in accordance with (production process 3), to thereby produce the target product (1.2 g, yield: 41%).

Yellow crystals, MS (APCI, m/z): 312 (MH$^+$), $^1$H-NMR (CDCl$_3$) δ 3.89 (3H, s), 3.93 (6H, s), 6.06(1H, br.s), 6.84 (2H, s), 6.94 (2H, d, J=12 Hz), 7.39(1H, s), 7.82(2H, d, J=12 Hz)

Production of (Z)-2,3-bis-(4-hydroxy-phenyl)-acrylonitrile (Compound 16)

4-Hydroxybenzyl cyanide (4.3 g) and 2-methoxyethoxymethyl chloride (4.1 g) were subjected to reaction in accordance with (production process 1), to thereby produce 4-methoxyethoxymethoxybenzyl cyanide (5.4 g, yield: 75%). The thus-produced 4-methoxyethoxymethoxybenzyl cyanide (2.1 g) and 4-methoxyethoxymethoxybenzaldehyde (2.0 g) produced in the production process for compound 1 were subjected to condensation in accordance with process A of (production process 2), to thereby yield an MEM form of the target product. Subsequently, the protective group was removed from the MEM form in accordance with (production process 3), to thereby produce the target product (1.1 g, yield: 49%).

Pale yellow-green crystals, MS (APCI, m/z): 238 (MH$^+$), $^1$H-NMR (DMSO-d6) δ 6.87 (1H, d, J=9 Hz), 6.89(1H, d, J=2 Hz, 9 Hz), 7.53(1H, d, J=9 Hz), 7.67(1H, s), 7.79(2H, d, J=9 Hz)

Production of (Z)-2-(3,4-dimethoxy-phenyl)-3-(4-hydroxy-phenyl)-acrylonitrile sodium salt (Compound 17)

Compound 1 (281 mg) was dissolved in ethanol. An aqueous solution of sodium hydroxide (in an amount stoichiometrically equivalent to that of compound 1) was added to the resultant solution, followed by stirring at room temperature. The resultant mixture was concentrated under reduced pressure, and the thus-precipitated crystals were separated through filtration, followed by recrystallization, to thereby produce the target product (270 mg, yield: 90%).

Pale yellow crystals, MS (APCI, m/z): 280 (M-Na$^+$), $^1$H-NMR (DMSO-d6) δ 3.76(3H, s), 3.82(3H, s), 6.19(1H, d, J=9 Hz), 6.96(1H, d, J=9 Hz), 7.05(1H, dd, J=2 Hz, 9 Hz), 7.11(1H, d, J=2 Hz), 7.41(1H, s), 7.58(1H, d, J=9 Hz)

Production of (Z)-2-(3,4-dimethoxy-phenyl)-3-(4-fluoro-phenyl)-acrylonitrile (Compound 18)

4-Fluorobenzaldehyde (620 mg) and 3,4-dimethoxybenzyl cyanide (880 mg) were subjected to condensation in accordance with process A of (production process 2), to thereby produce the target product (1.02 g, yield: 72%).

Slightly yellow crystals, MS (APCI, m/z): 283 (M$^-$), $^1$H-NMR (CDCl$_3$) δ 3.93(3H, s), 3.96(3H, s), 6.92(1H, d, J=9 Hz), 7.11 to 7.18(2H, m), 7.13(1H, d, J=2 Hz), 7.25(1H, dd, J=2 Hz, 9 Hz), 7.39(1H, s), 7.84 to 7.90(2H, m)

Production of (Z)-2-(3,4-dimethoxy-phenyl)-3-(4-nitro-phenyl)-acrylonitrile (Compound 19)

4-Nitrobenzaldehyde (760 mg) and 3,4-dimethoxybenzyl cyanide (890 mg) were subjected to condensation in accordance with process B of (production process 2), to thereby produce the target product (1.31 g, yield: 85%).

Slightly yellow crystals, MS (APCI, m/z): 310 (M$^-$), $^1$H-NMR (CDCl$_3$) δ 3.95(3H, s), 3.98(3H, s), 6.95(1H, d, J=9 Hz), 7.17(1H, d, J=2 Hz), 7.32(1H, dd, J=2 Hz, 9 Hz), 7.47(1H, s), 8.01(2H, d, J=9 Hz), 8.32(2H, d, J=9 Hz)

Production of (Z)-2-(3,4-dimethoxy-phenyl)-3-(2-fluoro-phenyl)-acrylonitrile (Compound 20)

2-Fluorobenzaldehyde (620 mg) and 3,4-dimethoxybenzyl cyanide (880 mg) were subjected to condensation in accordance with process A of (production process 2), to thereby produce the target product (562 mg, yield: 40%).

Slightly yellow crystals, MS (APCI, m/z): 283 (M$^-$), $^1$H-NMR (CDCl$_3$) δ 3.94(3H, s), 3.97(3H, s), 6.93(1H, d, J=8 Hz), 7.11 to 7.18(1H, m), 7.17(1H, d, J=2 Hz), 7.23 to 7.29(1H, m), 7.29(1H, dd, J=2 Hz, 8 Hz), 7.37 to 7.45(1H, m), 7.66(1H, s), 8.20 to 8.25(1H, m)

Production of 4-[(Z)-2-cyano-2-(3,4-dimethoxy-phenyl)-vinyl]-benzonitrile (Compound 21)

4-Cyanobenzaldehyde (1.97 g) and 3,4-dimethoxybenzyl cyanide (1.80 g) were subjected to condensation in accordance with process A of (production process 2), to thereby produce the target product (3.33 g, yield: 77%).

Slightly yellow crystals, MS (APCI, m/z): 290 (M$^-$), $^1$H-NMR (CDCl$_3$) δ 3.95(3H, s), 3.97(3H, s), 6.94(1H, d, J=8 Hz), 7.16(1H, d, J=2 Hz), 7.30(1H, dd, J=2 Hz, 9 Hz), 7.43(1H, s), 7.75(2H, d, J=9 Hz), 7.95(2H, d, J=9 Hz)

Production of (Z)-3-(2,3-difluoro-phenyl)-2-(3,4-dimethoxy-phenyl)-acrylonitrile (Compound 22)

2,3-Difluorobenzaldehyde (426 mg) and 3,4-dimethoxybenzyl cyanide (532 mg) were subjected to condensation in accordance with process A of (production process 2), to thereby produce the target product (813 mg, yield: 90%).

Slightly yellow crystals, MS (APCI, m/z): 301 (M$^-$), $^1$H-NMR (CDCl$_3$) δ 3.94(3H, s), 3.97(3H, s), 6.94(1H, d, J=9 Hz), 7.17(1H, d, J=2 Hz), 7.17 to 7.28(2H, m), 7.31(1H, dd, J=2 Hz, 9 Hz), 7.62(1H, s), 7.95 to 8.01(1H, m)

Production of (Z)-3-(2,4-difluoro-phenyl)-2-(3,4-dimethoxy-phenyl)-acrylonitrile (Compound 23)

2,4-Difluorobenzaldehyde (142 mg) and 3,4-dimethoxybenzyl cyanide (177 mg) were subjected to condensation in accordance with process B of (production process 2), to thereby produce the target product (94 mg, yield: 31%).

Slightly yellow crystals, MS (APCI, m/z): 301 (M$^-$), $^1$H-NMR (CDCl$_3$) δ 3.94(3H, s), 3.97(3H, s), 6.88 to 6.94 (1H, m), 6.93(1H, d, J=8 Hz), 6.98 to 7.04(1H, m), 7.15(1H, d, J=2 Hz), 7.28(1H, dd, J=2 Hz, 8 Hz), 7.57(1H, s), 8.21 to 8.28(1H, m)

Production of (Z)-3-(2,5-difluoro-phenyl)-2-(3,4-dimethoxy-phenyl)-acrylonitrile (Compound 24)

2,5-Difluorobenzaldehyde (1.42 g) and 3,4-dimethoxybenzyl cyanide (1.77 g) were subjected to condensation in accordance with process A of (production process 2), to thereby produce the target product (2.20 g, yield: 73%).

Slightly yellow crystals, MS (APCI, m/z): 301 (M$^-$), $^1$H-NMR (CDCl$_3$) δ 3.94(3H, s), 3.97(3H, s), 6.93(1H, d, J=9 Hz), 7.07 to 7.14(2H, m), 7.16(1H, d, J=2 Hz), 7.30(1H, d, J=2 Hz, 9 Hz), 7.58(1H, s), 7.92 to 7.98(1H, m)

Production of (Z)-3-(3,4-difluoro-phenyl)-2-(3,4-dimethoxy-phenyl)-acrylonitrile (Compound 25)

3,4-Difluorobenzaldehyde (426 mg) and 3,4-dimethoxybenzyl cyanide (532 mg) were subjected to condensation in accordance with process A of (production process 2), to thereby produce the target product (780 mg, yield: 86%).

Slightly yellow crystals, MS (APCI, m/z): 301 (M$^-$), $^1$H-NMR (CDCl$_3$) δ 3.94(3H, s), 3.96(3H, s), 6.93(1H, d, J=8 Hz), 7.13(1H, d, J=2 Hz), 7.25(1H, dd, J=2 Hz, 8 Hz), 7.21 to 7.29(1H, m), 7.32(1H, s), 7.57 to 7.62(1H, m), 7.71 to 7.78(1H, m)

Production of (Z)-3-(3,5-difluoro-phenyl)-2-(3,4-dimethoxy-phenyl)-acrylonitrile (Compound 26)

3,5-Difluorobenzaldehyde (1.42 g) and 3,4-dimethoxybenzyl cyanide (1.77 g) were subjected to condensation in accordance with process A of (production process 2), to thereby produce the target product (2.10 g, yield: 69%).

Slightly yellow crystals, MS (APCI, m/z): 301 (M$^-$), $^1$H-NMR (CDCl$_3$) δ 3.94(3H, s), 3.97(3H, s), 6.84 to 6.91 (1H, m), 6.93(1H, d, J=9 Hz), 7.13(1H, d, J=2 Hz), 7.27(1H, dd, J=2 Hz, 8 Hz), 7.32(1H, s), 7.36 to 7.43(1H, m)

Production of (Z)-2-(3,4-dimethoxy-phenyl)-3-(2,3,4-trifluoro-phenyl)-acrylonitrile (Compound 27)

2,3,4-Trifluorobenzaldehyde (160 mg) and 3,4-dimethoxybenzyl cyanide (177 mg) were subjected to condensation in accordance with process B of (production process 2), to thereby produce the target product (90 mg, yield: 30%).

Slightly yellow crystals, MS (APCI, m/z): 319 (M$^-$), $^1$H-NMR (CDCl$_3$) δ 3.94(3H, s), 3.97(3H, s), 6.94(1H, d, J=9 Hz), 7.05 to 7.14(1H, m), 7.15(1H, d, J=2 Hz), 7.29(1H, dd, J=2 Hz, 8 Hz), 7.52(1H, s), 7.93 to 8.02(1H, m)

Production of (Z)-2-(3,4-dimethoxy-phenyl)-3-(2,3,5-trifluoro-phenyl)-acrylonitrile (Compound 28)

2,3,5-Trifluorobenzaldehyde (320 mg) and 3,4-dimethoxybenzyl cyanide (354 mg) were subjected to condensation in accordance with process A of (production process 2), to thereby produce the target product (536 mg, yield: 84%).

Slightly yellow crystals, MS (APCI, m/z): 319 (M$^-$), $^1$H-NMR (CDCl$_3$) δ 3.95(3H, s), 3.97(3H, s), 6.94(1H, d, J=8 Hz), 6.95 to 7.05(1H, m), 7.16(1H, d, J=2 Hz), 7.31(1H, dd, J=2 Hz, 8 Hz), 7.56(1H, s), 7.71 to 7.77(1H, m)

Production of (Z)-2-(3,4-dimethoxy-phenyl)-3-(2,3,6-trifluoro-phenyl)-acrylonitrile (Compound 29)

2,3,6-Trifluorobenzaldehyde (320 mg) and 3,4-dimethoxybenzyl cyanide (354 mg) were subjected to condensation in accordance with process A of (production process 2), to thereby produce the target product (549 mg, yield: 86%).

Slightly yellow crystals, MS (APCI, m/z): 319 (M$^-$), $^1$H-NMR (CDCl$_3$) δ 3.94(3H, s), 3.96(3H, s), 6.94(1H, d, J=9 Hz), 6.93 to 6.99(1H, m), 7.17(1H, d, J=2 Hz), 7.17(1H, d, J=2 Hz), 7.18 to 7.26(1H, m), 7.27(1H, s), 7.32(1H, dd, J=2 Hz, 8 Hz)

Production of (Z)-2-(3,4-dimethoxy-phenyl)-3-(2,4,5-trifluoro-phenyl)-acrylonitrile (Compound 30)

2,4,5-Trifluorobenzaldehyde (160 mg) and 3,4-dimethoxybenzyl cyanide (177 mg) were subjected to condensation in accordance with process B of (production process 2), to thereby produce the target product (80 mg, yield: 26%).

Slightly yellow crystals, MS (APCI, m/z): 319 (M$^-$), $^1$H-NMR (CDCl$_3$) δ 3.94(3H, s), 3.97(3H, s), 6.93(1H, d, J=9 Hz), 6.99 to 7.06(1H, m), 7.14(1H, d, J=2 Hz), 7.28(1H, dd, J=2 Hz, 9 Hz), 7.51(1H, s), 8.07 to 8.16(1H, m)

Production of (Z)-2-(3,4-dimethoxy-phenyl)-3-(3,4,5-trifluoro-phenyl)-acrylonitrile (Compound 31)

3,4,5-Trifluorobenzaldehyde (160 mg) and 3,4-dimethoxybenzyl cyanide (177 mg) were subjected to condensation in accordance with process B of (production process 2), to thereby produce the target product (60 mg, yield: 19%).

Slightly yellow crystals, MS (APCI, m/z): 319 (M$^-$), $^1$H-NMR (CDCl$_3$) δ 3.94(3H, s), 3.96(3H, s), 6.93(1H, d, J=9 Hz), 7.11(1H, d, J=2 Hz), 7.25(1H, s), 7.26(1H, dd, J=2 Hz, 9 Hz), 7.48 to 7.56(1H, m)

Production of (Z)-3-(2,6-difluoro-phenyl)-2-(3,4-dimethoxy-phenyl)-acrylonitrile (Compound 32)

2,6-Difluorobenzaldehyde (284 mg) and 3,4-dimethoxybenzyl cyanide (354 mg) were subjected to condensation in accordance with process A of (production process 2), to thereby produce the target product (358 mg, yield: 40%).

Slightly yellow crystals, MS (APCI, m/z): 301 (M$^-$), $^1$H-NMR (CDCl$_3$) δ 3.94(3H, s), 3.96(3H, s), 6.93(1H, d, J=9 Hz), 6.98 to 7.05 (2H, dd, m), 7.17(1H, d, J=2 Hz), 7.31(1H, dd, J=2 Hz, 9 Hz), 7.32(1H, s), 7.33 to 7.42(1H, m)

Production of (Z)-2-(3,4-dimethoxy-phenyl)-3-(3-nitro-phenyl)-acrylonitrile (Compound 33)

3-Nitrobenzaldehyde (3.02 g) and 3,4-dimethoxybenzyl cyanide (3.54 g) were subjected to condensation in accordance with process A of (production process 2), to thereby produce the target product (6.01 g, yield: 97%).

Yellow crystals, MS (APCI, m/z): 310 (M$^-$), $^1$H-NMR (CDCl$_3$) δ 3.95(3H, s), 3.98 (3H, s), 6.95(1H, d, J=9 Hz), 7.17(1H, d, J=2 Hz), 7.31(1H, dd, J=2 Hz, 9 Hz), 7.49(1H, s), 7.68(1H, t, J=8 Hz), 8.27(1H, ddd, J=1 Hz, 2 Hz, 8 Hz), 8.33(1H, ddd, J=1 Hz, 2 Hz, 8 Hz), 8.56(1H, t, J=2 Hz)

Production of (Z)-3-(4-amino-phenyl)-2-(3,4-dimethoxy-phenyl)-acrylonitrile (Compound 34)

Compound 19 (880 mg) was dissolved in acetic acid. Zinc powder was added to the resultant solution, and the resultant mixture was stirred for four hours. The mixture was concentrated to dryness under reduced pressure, followed by purification by use of a silica gel column, to thereby produce the target product (760 mg, yield: 95%).

Slightly yellow crystals, MS (APCI, m/z): 281 (MH$^+$), $^1$H-NMR (CDCl$_3$) δ 3.91(3H, s), 3.95(3H, s), 6.71(2H, d, J=9 Hz), 6.90(1H, d, J=9 Hz), 7.11(1H, d, J=2 Hz), 7.20(1H, dd, J=2 Hz, 8 Hz), 7.29(1H, s), 7.75(2H, d, J=9 Hz)

Production of ethyl [4-[(Z)-2-cyano-2-(3,4-dimethoxy-phenyl)-vinyl]-phenoxy]-acetate (Compound 35)

Compound 1 (281 mg) and ethyl chloroacetate (245 mg) were dissolved in acetone, and potassium carbonate was added to the resultant solution, followed by reflux for three hours. The resultant mixture was subjected to filtration, and insoluble matter was removed from the mixture. The resultant filtrate was concentrated to dryness under reduced pressure, followed by recrystallization, to thereby produce the target product (124 mg, yield: 34%).

White crystals, MS (APCI, m/z): 368 (MH$^+$), $^1$H-NMR (CDCl$_3$) δ 1.32(3H, t, J=7 Hz), 3.93(3H, s), 3.96(3H, s), 4.30(2H, q, J=7 Hz), 4.68(2H, s), 6.92(1H, d, J=9 Hz), 6.98(2H, d, J=9 Hz), 7.13(1H, d, J=2 Hz), 7.24(1H, dd, J=2 Hz, 9 Hz), 7.36(1H, s), 7.86(2H, d, J=9 Hz)

Production of methyl 4-[(Z)-2-cyano-2-(3,4-dimethoxy-phenyl)-vinyl]-benzoate (Compound 36)

Methyl 4-formylbenzoate (1.64 g) and 3,4-dimethoxybenzyl cyanide (1.77 g) were subjected to condensation in accordance with process B of (production process 2), to thereby produce the target product (0.97 g, yield: 30%).

Pale yellow crystals, MS (APCI, m/z): 323 (M$^-$), $^1$H-NMR (CDCl$_3$) δ 3.94(3H, s), 3.95(3H, s), 3.97(3H, s), 6.94(1H, d, J=9 Hz), 7.16(1H, d, J=2 Hz), 7.30(1H, dd, J=2 Hz, 9 Hz), 7.46(1H, s), 7.92(2H, d, J=9 Hz), 8.12(2H, d, J=9 Hz)

Production of (Z)-2-(3,4-dimethoxy-phenyl)-3-(2-nitro-phenyl)-acrylonitrile (Compound 37)

2-Nitrobenzaldehyde (1.51 g) and 3,4-dimethoxybenzyl cyanide (1.77 g) were subjected to condensation in accordance with process A of (production process 2), to thereby produce the target product (2.59 g, yield: 84%).

Yellow-orange crystals, MS (APCI, m/z): 310 (M$^-$), $^1$H-NMR (CDCl$_3$) δ 3.95(3H, s), 3.97(3H, s), 6.95(1H, d, J=9 Hz), 7.19(1H, d, J=2 Hz), 7.33(1H, dd, J=2 Hz, 9 Hz), 7.62(1H, br t), 7.78(1H, br t), 7.93(1H, s), 7.94(1H, d, J=8 Hz,), 8.24(1H, d, J=8 Hz)

Production of (Z)-3-(4-chloro-3-nitro-phenyl)-2-(3,4-dimethoxy-phenyl)-acrylonitrile (Compound 38)

4-Chloro-3-nitrobenzaldehyde (557 mg) and 3,4-dimethoxybenzyl cyanide (532 mg) were subjected to condensation in accordance with process B of (production process 2), to thereby produce the target product (372 mg, yield: 36%).

Pale yellow crystals, MS (ESI, m/z): 343 (M-H$^-$), $^1$H-NMR (CDCl$_3$) δ 3.95(3H, s), 3.97(3H, s), 6.95(1H, d, J=9 Hz), 7.14(1H, d, J=2 Hz), 7.29(1H, dd, J=2 Hz, 9 Hz), 7.38(1H, s), 7.66(1H, d, J=9 Hz), 8.15(1H, dd, J=2 Hz, 9 Hz), 8.23(1H, d, J=2 Hz)

Production of (Z)-2-(3,4-dimethoxy-phenyl)-3-(2-fluoro-5-nitro-phenyl)-acrylonitrile (Compound 39)

2-Fluoro-5-nitrobenzaldehyde (85 mg) and 3,4-dimethoxybenzyl cyanide (89 mg) were subjected to condensation in accordance with process B of (production process 2), to thereby produce the target product (24 mg, yield: 15%).

Pale yellow crystals, MS (APCI, m/z): 328 (M$^-$), $^1$H-NMR (CDCl$_3$) δ 3.95(3H, s), 3.98(3H, s), 6.95(1H, d, J=9 Hz), 7.18(1H, dd, J=2 Hz), 7.31 (1H, d, J=9 Hz), 7.34(1H, d, J=2 Hz, 9 Hz), 7.57(1H, s), 8.32(1H, ddd, J=3 Hz, 4 Hz, 9 Hz), 9.08(1H, dd, J=3 Hz, 6 Hz)

Production of (Z)-2-(3,4-dimethoxy-phenyl)-3-(4-ethoxy-3-nitro-phenyl)-acrylonitrile (Compound 40)

4-Ethoxy-3-nitrobenzaldehyde (586 mg) and 3,4-dimethoxybenzyl cyanide (532 mg) were subjected to condensation in accordance with process B of (production process 2), to thereby produce the target product (425 mg, yield: 40%).

Yellow-orange crystals, MS (ESI, m/z): 354 (M$^-$), $^1$H-NMR (CDCl$_3$) δ 1.52(3H, t, J=7 Hz), 3.95 (3H, s), 3.97(3H, s), 4.27(2H, q, J=7 Hz), 6.94(1H, d, J=9 Hz), 7.12(1H, d, J=2 Hz), 7.16(1H, d, J=9 Hz), 7.25(1H, dd, J=2 Hz, 9 Hz), 7.34(1H, s), 8.16(1H, d, J=2 Hz), 8.26(1H, dd, J=2 Hz, 9 Hz)

Production of 4-[(Z)-2-cyano-2-(3,4-dimethoxy-phenyl)-vinyl]-phenyl methyl succinate (Compound 41)

Compound 1 (50 mg) and succinic acid monomethyl ester chloride (44 μL) were dissolved in pyridine (1 mL), followed by stirring for a whole day and night. After completion of reaction, the resultant reaction mixture was concentrated to dryness under reduced pressure, followed by purification by means of silica gel chromatography employing a chloroform/methanol system, to thereby produce the target product (63 mg, yield: 90%).

Pale yellow crystals, MS(APCI, m/z):396(MH$^+$), $^1$H-NMR(CDCl$_3$) δ2.77(2H, dd, J=6 Hz, 7 Hz), 2.92(2H, dd, J=6 Hz, 7 Hz), 3.74(3H, s), 3.93(3H, s), 3.96(3H, s), 6.92(1H, d, J=8 Hz), 7.14(1H, d, J=2 Hz), 7.21(2H, d, J=9 Hz), 7.26(1H, dd, J=2 Hz, 8 Hz), 7.40(1H, s), 7,89(2H, d, J=9 Hz)

Production of 4-[(Z)-2-cyano-2-(3,4-dimethoxy-phenyl)-vinyl]-phenyl ethyl succinate (Compound 42)

Compound 1 (50 mg) and succinic acid monoethyl ester chloride (51 μL) were dissolved in pyridine (1 mL), followed by stirring for a whole day and night. After completion of reaction, the resultant reaction mixture was concentrated to dryness under reduced pressure, followed by purification by means of silica gel chromatography employing a chloroform/methanol system, to thereby produce the target product (73 mg, yield: 90%).

Pale yellow crystals, MS(APCI, m/z):410(MH$^+$), $^1$H-NMR(CDCl$_3$) δ1.29(3H, t, J=7 Hz), 2.75(2H, dd, J=6 Hz, 8 Hz), 2.91(2H, dd, J=6 Hz, 8 Hz), 3.93(3H, s), 3.97(3H, s), 4.20(2H, dd, J=7 Hz, 14 Hz), 6.92(1H, d, J=9 Hz), 7.14(1H, d, J=2 Hz), 7.21(2H, d, J=9 Hz), 7.26(1H, dd, J=2 Hz, 9 Hz), 7.40(1H, s), 7,90(2H, d, J=9 Hz)

Production of bis-{4-[(Z)-2-cyano-2-(3,4-dimethoxy-phenyl)-vinyl]-phenyl} succinate (Compound 43)

Compound 1 (50 mg) and succinyl dichloride (20 μL) were dissolved in pyridine (1 mL), followed by stirring for a whole day and night. After completion of reaction, the resultant reaction mixture was concentrated to dryness under reduced pressure, followed by purification by means of silica gel chromatography employing a chloroform/methanol system, to thereby produce the target product (56 mg, yield: 98%).

Pale yellow crystals, MS(EI, m/z):644 (M$^+$), $^1$H-NMR (CDCl$_3$) δ3.05(4H, s), 3.93(6H, s), 3.96(6H, s), 6.92(2H, d, J=9 Hz), 7.14(2H, d, J=2 Hz), 7.23(4H, d, J=9 Hz), 7.26(2H, dd, J=2 Hz, 9 Hz), 7.41(2H, s), 7,91(4H, d, J=9 Hz)

Production of (Z)-2-(3,4-dimethoxyphenyl)-3-(4-β-D-glucopyranosyl-phenyl)-acrylonitrile (Compound 44)

Compound 1 (1.71 g) was dissolved in acetone, and α-D-acetobromoglucose (10.0 g) and potassium carbonate (3.57 g) were added to the resultant solution, followed by boiling/reflux for a whole day and night under vigorous stirring. The resultant mixture was subjected to filtration, to thereby remove insoluble matter. The thus-filtered product was washed with chloroform and mixed with the above-obtained filtrate, and the resultant mixture was concentrated to dryness under reduced pressure. The resultant residue was purified by means of silica gel chromatography employing a chloroform/methanol system. The thus-purified product was suspended in anhydrous methanol, and 28% NaOMe was added dropwise to the resultant suspension, followed by stirring at room temperature for 0.5 hours. Water was added to the resultant reaction mixture, and the mixture was neutralized with an ion-exchange resin (sulfonic acid-$^+$H type). The resin was removed through filtration, and the mixture was concentrated to dryness under reduced pressure, followed by purification by means of silica gel chromatography employing a chloroform/methanol system, to thereby produce the target product (696 mg, yield: 26%).

Pale yellow crystals, MS (EI, m/z): 443(M$^+$), $^1$H-NMR (DMSO-d6) δ3.21(1H, t, J=9 Hz), 3.31(1H, t, J=9 Hz), 3.35(1H, t, J=9 Hz), 3.44(1H, m), 3.50(1H, dd, J=6 Hz, 12 Hz), 3.74(1H, dd, J=1 Hz, 12 Hz), 3.81(3H, s), 3.86(3H, s), 5.00(1H, d, J=7 Hz), 7.09(1H, d, J=9 Hz), 7.18(2H, d, J=9 Hz), 7.25(1H, dd, J=2 Hz, 9 Hz), 7.29(1H, d, J=2 Hz), 7.86(1H, s), 7.90(2H, d, J=9 Hz)

Production of (Z)-2-(3,4-dimethoxy-phenyl)-3-(4-hydroxy-3-nitro-phenyl)-acrylonitrile (Compound 45)

The hydroxyl group of 4-hydroxy-3-nitrobenzaldehyde (500 mg) was protected by use of 2-methoxyethoxymethyl chloride (374 mg) in accordance with (production process 1), to thereby produce an MEM form (605 mg, yield: 70%). The resultant MEM form (255 mg) and 3,4-dimethoxybenzyl cyanide (177 mg) were subjected to condensation in accordance with process B of (production process 2), to thereby produce (Z)-2-(3,4-dimethoxy-phenyl)-3-[4-(2-methoxy-ethoxymethoxy)-3-nitro-phenyl]-acrylonitrile (153 mg, yield: 40%). The thus-produced (Z)-2-(3,4-dimethoxy-phenyl)-3-[4-(2-methoxy-ethoxymethoxy)-3-nitro-phenyl]-acrylonitrile (140 mg) was subjected to deprotection in accordance with (production process 3), to thereby produce the target product (72 mg, yield: 60%).

Yellow-orange crystals, MS (APCI, m/z): 327 (MH$^+$), $^1$H-NMR (CDCl$_3$) δ 3.94(3H, s), 3.97(3H, s), 6.94(1H, d, J=9 Hz), 7.13(1H, d, J=2 Hz), 7.27(1H, dd, J=2 Hz, 9 Hz), 7.28(1H, d, J=9 Hz), 7.36(1H, s), 8.29(1H, dd, J=2 Hz, 9 Hz), 8.51(1H, d, J=2 Hz), 10.77(1H, s)

Production of (Z)-2-(3,4-dimethoxy-phenyl)-3-(6-nitro-benzo[1,3]dioxol-5-yl)-acrylonitrile (Compound 46)

6-Nitropiperanal (195 mg) and 3,4-dimethoxybenzyl cyanide (177 mg) were subjected to condensation in accordance with process B of (production process 2), to thereby produce the target product (124 mg, yield: 35%).

Pale yellow crystals, MS (ESI, m/z): 354 (M$^-$), $^1$H-NMR (CDCl$_3$) δ 3.94(3H, s), 3.96(3H, s), 6.21(2H, s), 6.94(1H, d, J=9 Hz), 7.17(1H, d, J=2 Hz), 7.28(1H, s), 7.30(1H, dd, J=2 Hz, 9 Hz), 7.72(1H, s), 7.88(1H, s)

Production of (Z)-3-(3,4-dimethoxy-phenyl)-2-[4-(2-methoxy-ethoxymethoxy)-phenyl]-acrylonitrile (Compound 47)

The hydroxyl group of 4-hydroxybenzyl cyanide (26.63 g) was protected by use of 2-methoxyethoxymethyl chloride (24.42 g) in accordance with (production process 1), to thereby produce an MEM form (24.39 g, yield: 55%). The resultant MEM form (22.13 g) and 3,4-dimethoxybenzaldehyde (16.62 g) were subjected to condensation in accordance with process A of (production process 2), to thereby produce the target product (29.79 g, yield: 81%).

Pale yellow crystals, MS (APCI, m/z): 370 (MH$^+$), $^1$H-NMR (CDCl$_3$) δ 3.39(3H, s), 3.55 to 3.59(2H, m), 3.82 to 3.86(2H, m), 3.95(3H, s), 3.97(3H, s), 5.31(2H, s), 6.92(1H, d, J=8 Hz), 7.11(1H, d, J=9 Hz), 7.34(1H, dd, J=2 Hz, 8 Hz), 7.38(1H, s), 7.58(1H, d, J=9 Hz), 7.69(1H, d, J=2 Hz)

Production of (Z)-3-(3,4-dimethoxy-phenyl)-2-(4-hydroxy-phenyl)-acrylonitrile (Compound 48)

The protective group of Compound 47 (18.45 g) was removed in accordance with (production process 3), to thereby produce the target product (8.38 g, yield: 60%).

Pale yellow crystals, MS (APCI, m/z): 282 (MH$^+$), $^1$H-NMR (CDCl$_3$) δ 3.94(3H, s), 3.97(3H, s), 6.90(1H, d, J=9 Hz), 6.92(1H, d, J=8 Hz), 7.33(1H, dd, J=2 Hz, 8 Hz), 7.34(1H, s), 7.54(1H, d, J=9 Hz), 7.67(1H, d, J=2 Hz)

Production of (Z)-2-(3,5-bis-trifluoromethyl-phenyl)-3-(4-hydroxy-phenyl)-acrylonitrile (Compound 49)

4-Methoxyethoxymethoxybenzaldehyde (420 mg) and 3,5-bis(trifluoromethyl)phenylacetonitrile (506 mg) were subjected to condensation in accordance with process A of (production process 2), and the resultant product was subjected to deprotection in accordance with (production process 3), to thereby produce the target product (122 mg, yield: 17%).

Pale yellow crystals, MS (ESI, m/z): 356 (M-H$^-$), $^1$H-NMR (CDCl$_3$) δ6.96(2H, br.d), 7.57(1H, s), 7.87(1H, s), 7.91(2H, br.d), 8.06(2H, s)

Production of (E)-2-(3,4-dimethoxy-phenyl)-3-(4-hydroxy-phenyl)-acrylonitrile (Compound 50)

Compound 1 (100 mg) was dissolved in acetonitrile, and the resultant solution was subjected to photoreaction by use of a high-pressure mercury lamp. The resultant reaction mixture was concentrated to dryness under reduced pressure, followed by purification by use of a silica gel column, to thereby produce the target product (41 mg, yield: 41%).

Pale yellow crystals, MS (APCI, m/z): 282 (MH$^+$), $^1$H-NMR (CDCl$_3$) δ 3.73(3H, s), 3.90(3H, s), 6.71(2H, d, J=9 Hz), 6.86(1H, d, J=8 Hz), 6.87(1H, d, J=2 Hz), 7.00(1H, dd, J=2 Hz, 8 Hz), 7.10(2H, d, J=9 Hz), 7.20(1H, s)

Production of (Z)-2-(3,4-dimethoxyphenyl)-3-(4-β-maltosyl-phenyl)-acrylonitrile (Compound 51)

Compound 1 (224 mg) was dissolved in acetone, and α-D-acetobromomaltose (2.23 g) and potassium carbonate (468 mg) were added to the resultant solution, followed by boiling/reflux for a whole day and night under vigorous stirring. The resultant mixture was subjected to filtration, to thereby remove insoluble matter. The thus-filtered product was washed with chloroform and mixed with the above-obtained filtrate, and the resultant mixture was concentrated to dryness under reduced pressure. The resultant residue was purified by means of silica gel chromatography employing a chloroform/methanol system. The thus-purified product was suspended in anhydrous methanol, and 28% NaOMe was added dropwise to the resultant suspension, followed by stirring at room temperature for 0.5 hours. Water was added to the resultant reaction mixture, and the mixture was neutralized with an ion-exchange resin (sulfonic acid-$^+$H type). The resin was removed through filtration, and the mixture was concentrated to dryness under reduced pressure, followed by purification by means of silica gel chromatography employing a chloroform/methanol system, to thereby produce the target product (195 mg, yield: 27%).

Pale yellow crystals, MS (ESI, m/z): 604(M-H$^-$), $^1$H-NMR(DMSO-d6) δ3.11(1H, t, J=9 Hz), 3.28(1H, dd, J=4 Hz, 10 Hz), 3.81(3H, s), 3.86(3H, s), 5.05(1H, d, J=8 Hz), 5.09(1H, d, J=3 Hz), 7.07(1H, d, J=9 Hz), 7.18(2H, d, J=9 Hz), 7.25(1H, dd, J=2 Hz, 9 Hz), 7.29(1H, d, J=2 Hz), 7.84(1H, s), 7.89(2H, d, J=9 Hz)

Production of (Z)-2-(3,4-dimethoxy-phenyl)-3-(2-ethoxy-5-nitro-phenyl)-acrylonitrile (Compound 52)

2-Ethoxy-5-nitrobenzaldehyde (390 mg) and 3,4-dimethoxybenzyl cyanide (354 mg) were subjected to condensation in accordance with process B of (production process 2), to thereby produce the target product (319 mg, yield: 45%).

Yellow-orange crystals, MS (ESI, m/z): 354 (M$^-$), $^1$H-NMR (CDCl$_3$) δ 1.52(3H, t, J=7 Hz), 3.95(3H, s), 3.97(3H, s), 4.24(2H, q, J=7 Hz), 6.95(1H, d, J=9 Hz), 7.00(1H, d, J=9 Hz), 7.17(1H, d, J=2 Hz), 7.30(1H, dd, J=2 Hz, 9 Hz), 7.70(1H, s), 8.29(1H, dd, J=3 Hz, 9 Hz), 8.92(1H, dd, J=3 Hz)

Production of (Z)-2-(3,4-dimethoxy-phenyl)-3-(3-hydroxy-4-nitro-phenyl)-acrylonitrile (Compound 53)

The hydroxyl group of 3-hydroxy-4-nitrobenzaldehyde (0.67 g) was protected by use of 2-methoxyethoxymethyl chloride (0.50 g) in accordance with (production process 1), to thereby produce an MEM form (0.97 g, yield: 95%). The resultant MEM form (944 mg) and 3,4-dimethoxybenzyl cyanide (673 mg) were subjected to condensation in accordance with process B of (production process 2), to thereby produce (Z)-2-(3,4-dimethoxy-phenyl)-3-[3-(2-methoxyethoxymethoxy)-4-nitro-phenyl]-acrylonitrile (515 mg, yield: 34%). The thus-produced (Z)-2-(3,4-dimethoxy-phenyl)-3-[3-(2-methoxy-ethoxymethoxy)-4-nitro-phenyl]-acrylonitrile (350 mg) was subjected to deprotection in accordance with (production process 3), to thereby produce the target product (267 mg, yield: 97%).

Yellow-orange crystals, MS (ESI, m/z): 325 (M-H$^-$), $^1$H-NMR (CDCl$_3$) δ 3.95(3H, s), 3.97(3H, s), 6.95(1H, d, J=9 Hz), 7.16(1H, d, J=2 Hz), 7.321(1H, dd, J=2 Hz, 9 Hz), 7.37(1H, s), 7.52(1H, dd, J=2 Hz, 9 Hz), 7.56(1H, d, J=2 Hz), 8.12(1H, d, J=9 Hz)

Production of (Z)-2-(3,4-dimethoxyphenyl)-3-(4-β-maltotriosyl-phenyl)-acrylonitrile (Compound 54)

Compound 1 (791 mg) was dissolved in acetone, and α-D-acetobromomaltotriose (11.1 g) and potassium carbonate (1.11 g) were added to the resultant solution, followed by boiling/reflux for a whole day and night under vigorous stirring. The resultant mixture was subjected to filtration, to thereby remove insoluble matter. The thus-filtered product was washed with chloroform and mixed with the above-obtained filtrate, and the resultant mixture was concentrated to dryness under reduced pressure. The resultant residue was purified by means of silica gel chromatography employing a chloroform/methanol system. The thus-purified product was suspended in anhydrous methanol, and 28% NaOMe was added dropwise to the resultant suspension, followed by stirring at room temperature for 0.5 hours. Water was added to the resultant reaction mixture, and the mixture was neutralized with an ion-exchange resin (sulfonic acid-$^+$H type). The resin was removed through filtration, and the mixture was concentrated to dryness under reduced pressure, followed by purification by means of silica gel chromatography employing a chloroform/methanol system, to thereby produce the target product (368 mg, yield: 17%).

Pale yellow crystals, MS (ESI, m/z): 766(M-H$^-$), $^1$H-NMR(DMSO-d6) δ3.07(1H, t, J=9 Hz), 3.25(1H, dd, J=4 Hz, 9 Hz), 3.81(1H, s), 3.86(1H, s), 5.02(1H, d, J=4 Hz), 5.06(1H, d, J=8 Hz), 5.09(1H, d, J=4 Hz), 7.08(1H, d, J=9 Hz), 7.18(2H, d, J=9 Hz), 7.24(1H, dd, J=2 Hz, 9 Hz), 7.31(1H, d, J=2 Hz), 7.89(1H, s), 7.91(2H, d, J=9 Hz)

Production of (Z)-2-(3,4-dimethoxy-phenyl)-3-(3-fluoro-2-hydroxy-phenyl)-acrylonitrile (Compound 55)

The hydroxyl group of 3-fluoro-2-hydroxybenzaldehyde (560 mg) was protected by use of 2-methoxyethoxymethyl chloride (500 mg) in accordance with (production process 1), to thereby produce an MEM form (660 mg, yield: 72%). The resultant MEM form (650 mg) and 3,4-dimethoxybenzyl cyanide (500 mg) were subjected to condensation in accordance with process A of (production process 2), to thereby produce (Z)-2-(3,4-dimethoxy-phenyl)-3-(3-fluoro-2-methoxyethoxymethoxy-phenyl)-acrylonitrile (680 mg, yield: 58%). The thus-produced (Z)-2-(3,4-dimethoxy-phenyl)-3-(3-fluoro-2-methoxyethoxymethoxy-phenyl)-acrylonitrile (670 mg) was subjected to deprotection in accordance with (production process 3), to therey produce the target product (140 mg, yield: 29%).

Pale yellow crystals, MS (APCI, m/z): 300 (MH$^+$), $^1$H-NMR (CDCl$_3$) δ 3.93(3H, s), 3.96(3H, s), 6.92(1H, d, J=9 Hz), 6.93 to 6.99(1H, m), 7.12 to 7.17(1H, m), 7.18(1H, d, J=2 Hz), 7.30(1H, dd, J=2 Hz, 9 Hz), 7.80(1H, s), 7.93(1H, d, J=8 Hz)

Production of (Z)-2,3-bis-(3,4-dimethoxy-phenyl)-acrylonitrile (Compound 56)

3,4-Dimethoxybenzaldehyde (1.00 g) and 3,4-dimethoxybenzyl cyanide (1.07 g) were subjected to condensation in accordance with process A of (production process 2), to thereby produce the target product (1.75 g, yield: 89%).

Pale yellow crystals, MS (APCI, m/z): 326 (MH$^+$), $^1$H-NMR (CDCl$_3$) δ 3.93(3H, s), 3.95(3H, s), 3.97(3H, s), 3.98(3H, s), 6.91(1H, d, J=9 Hz), 6.93(1H, d, J=9 Hz), 7.13(1H, d, J=2 Hz), 7.24(1H, dd, J=2 Hz, 9 Hz), 7.35(1H, s), 7.36(1H, dd, J=2 Hz, 9 Hz), 7.67(1H, d, J=2 Hz)

Production of (Z)-3-(3-amino-phenyl)-2-(3,4-dimethoxy-phenyl)-acrylonitrile (Compound 57)

Compound 33 (1.80 g) was dissolved in acetic acid. Zinc powder was added to the resultant solution, and the resultant mixture was stirred for four hours. The mixture was concentrated to dryness under reduced pressure, followed by purification by use of a silica gel column, to thereby produce the target product (1.30 g, yield: 80%).

Pale yellow crystals, MS (APCI, m/z): 281 (MH$^+$), $^1$H-NMR (CDCl$_3$) δ 3.81(2H, brs), 3.93(3H, s), 3.96(3H, s), 6.75(1H, ddd, J=1 Hz, 2 Hz, 9 Hz), 6.92(1H, d, J=9 Hz), 7.13(1H, d, J=2 Hz), 7.15 to 7.19(1H, m), 7.23(1H, d, J=9 Hz), 7.25(1H, dd, J=2 Hz, 9 Hz), 7.26 to 7.28(1H, m), 7.34(1H, s)

Production of (Z)-2-(3,4-dimethoxy-phenyl)-3-[3-fluoro-4-(2-methoxy-ethoxymethoxy)-phenyl]-acrylonitrile (Compound 58)

The hydroxyl group of 3-fluoro-4-hydroxybenzaldehyde (3.92 g) was protected by use of 2-methoxyethoxymethyl chloride (3.49 g) in accordance with (production process 1), to thereby produce an MEM form (4.98 g, yield: 78%). The resultant MEM form (4.98 g) and 3,4-dimethoxybenzyl cyanide (3.87 g) were subjected to condensation in accordance with process A of (production process 2), to thereby produce the target product (6.55 g, yield: 78%).

Pale yellow crystals, MS (APCI, m/z): 284 (M-CH$_2$OCH$_2$CH$_2$OCH$_3^-$), $^1$H-NMR (CDCl$_3$) δ 3.38(3H, s), 3.56 to 3.60(2H m), 3.87 to 3.91(2H, m), 3.93(3H, s), 3.96(3H, s), 6.92(1H, d, J=8 Hz), 7.12(1H, d, J=2 Hz), 7.24(1H, dd, J=2 Hz, 8 Hz), 7.30(1H, t, J=9 Hz), 7.31(1H, s), 7.56(1H, dd, J=2 Hz, 9 Hz), 7.60(1H, dd, J=2 Hz, 12 Hz)

Production of (Z)-2-(3,4-dimethoxy-phenyl)-3-(3-fluoro-4-hydroxy-phenyl)-acrylonitrile (Compound 59)

Compound 58 (6.00 g) was subjected to deprotection in accordance with (production process 3), to thereby produce the target product (4.44 g, yield: 96%).

Pale yellow crystals, MS (APCI, m/z): 298 (M-H$^-$), $^1$H-NMR (CDCl$_3$+CD$_3$OD) δ 3.93(3H, s), 3.96(3H, s), 6.93(1H, d, J=8 Hz), 7.01(1H, t, J=9 Hz), 7.12(1H, d, J=2 Hz), 7.22(1H, dd, J=2 Hz, 8 Hz), 7.32(1H, s), 7.51(1H, dd, J=2 Hz, 9 Hz), 7.69(1H, dd, J=2 Hz, 12 Hz)

Production of mono-{4-[(Z)-2-cyano-2-(3,4-dimethoxy-phenyl)-vinyl]-phenyl} sodium phosphate (Compound 60)

Compound 70 (103 mg) was dissolved in ethanol, and sodium methoxide was added to the resultant solution, followed by stirring for 12 hours. The resultant mixture was concentrated to dryness under reduced pressure, and then the resultant product was dissolved in water. The resultant solution was washed with ethyl acetate, and the thus-obtained aqueous layer was freeze-dried, to thereby produce the target product (112 mg, yield: 97%).

Pale yellow crystals, MS (ESI, m/z): 360 (M−2Na+H$^-$), $^1$H-NMR(D$_2$O) δ3.71(3H, s), 3.75(3H, s), 6.88(1H, d, J=8 Hz), 6.99(1H, d, J=2 Hz), 7.07(1H, dd, J=2, 8 Hz), 7.22(2H, d, J=8 Hz), 7.43(1H, s), 7.70(2H, d, J=8 Hz)

Production of 4-[(Z)-1-cyano-2-(3,4-dimethoxy-phenyl)-vinyl]phenyl acetate (Compound 61)

Compound 48 (1.41 g) was acetylated with acetic anhydride and pyridine in accordance with a customary method, to thereby produce the target product (1.52 g, yield: 94%).

White crystals, MS (APCI, m/z): 324 (MH$^+$), $^1$H-NMR (CDCl$_3$) δ 2.33(3H, s), 3.95(3H, s), 3.98(3H, s), 6.93(1H, d, J=8 Hz), 7.18(2H, d, J=9 Hz), 7.35(1H, dd, J=2 Hz, 8 Hz), 7.42(1H, s), 7.67(2H, d, J=9 Hz), 7.71(1H, d, J=2 Hz)

Production of (Z)-2-(3,4-dimethoxy-phenyl)-3-(4-formyl-phenyl)-acrylonitrile (Compound 62)

4-Diethoxymethyl-benzaldehyde (4.16 g) and 3,4-dimethoxybenzyl cyanide (3.54 g) were subjected to condensation in accordance with process A of (production process 2), to thereby produce (Z)-3-(4-diethoxymethyl-phenyl)-2-(3,4-dimethoxy-phenyl)-acrylonitrile (6.54 g, yield: 89%). The thus-produced (Z)-3-(4-diethoxymethyl-phenyl)-2-(3,4-dimethoxy-phenyl)-acrylonitrile (1.84 g) was dissolved in methanol, and water and 2N sulfuric acid were added to the resultant solution, followed by stirring, to thereby produce the target product (1.20 g, yield: 82%).

Pale yellow crystals, MS (APCI, m/z): 294 (MH$^+$), $^1$H-NMR (CDCl$_3$) δ 3.95(3H, s), 3.98(3H, s), 6.95(1H, d, J=9 Hz), 7.17(1H, d, J=2 Hz), 7.32(1H, dd, J=2 Hz, 9 Hz), 7.48(1H, s), 7.97 (2H, d, J=9 Hz), 8.02(2H, d, J=9 Hz), 10.06(1H, s)

Production of 4-[(Z)-1-cyano-2-(3,4-dimethoxy-phenyl)-vinyl]-2-ethoxy-phenyl acetate (Compound 63)

Compound 11 (1.30 g) was acetylated with acetic anhydride and pyridine in accordance with a customary method, to thereby produce the target product (1.19 g, yield: 81%).

White crystals, MS (APCI, m/z): 368 (MH$^+$), $^1$H-NMR (CDCl$_3$) δ 1.44(3H, t, J=7 Hz), 2.34(3H, s), 3.94(3H, s), 3.97(3H, s), 4.16(2H, q, J=7 Hz), 6.93(1H, d, J=9 Hz), 7.11(1H, d, J=8 Hz), 7.13(1H, d, J=2 Hz), 7.26(1H, dd, J=2 Hz, 8 Hz), 7.31(1H, d, J=2 Hz, 8 Hz), 7.37(1H, s), 7.69(1H, d, J=2 Hz)

Production of 4-[(Z)-1-cyano-2-(3,4-dimethoxy-phenyl)-vinyl]-2-fluoro-phenyl acetate (Compound 64)

Compound 59 (1.20 g) was acetylated with acetic anhydride and pyridine in accordance with a customary method, to thereby produce the target product (1.26 g, yield: 92%).

Slightly yellow crystals, MS (APCI, m/z): 298 (M-COCH$_3^-$), $^1$H-NMR (CDCl$_3$) δ 2.37(3H, s), 3.94(3H, s), 3.97(3H, s), 6.93(1H, d, J=9 Hz), 7.13(1H, d, J=2 Hz), 7.22(1H, d, J=8 Hz), 7.27(1H, d, J=2 Hz, 9 Hz), 7.35(1H, s), 7.62 to 7.67(1H, m), 7.72(1H, dd, J=2 Hz, 11 Hz)

Production of 4-[(Z)-2-cyano-2-(3,4,5-trimethoxy-phenyl)-vinyl]-phenyl acetate (Compound 65)

Compound 15 (1.20 g) was acetylated with acetic anhydride and pyridine in accordance with a customary method, to thereby produce the target product (1.27 g, yield: 93%).

White crystals, MS (APCI, m/z): 352 (M-H$^-$), $^1$H-NMR (CDCl$_3$) δ 2.34(3H, s), 3.89(3H, s), 3.94(6H, s), 6.87(2H, s), 7.22(2H, d, J=9 Hz), 7.43(1H, s), 7.91(2H, d, J=9 Hz)

Production of ethyl 7-[4-[(Z)-2-cyano-2-(3,4-dimethoxy-phenyl)-vinyl]-phenoxy]-heptanoate (Compound 66)

Compound 1 (200 mg) was dissolved in dimethyl sulfoxide, and anhydrous potassium carbonate was added to the resultant solution, followed by stirring at room temperature for one hour. Thereafter, ethyl 7-bromoheptanoate (169 mg) was added to the resultant mixture, and the mixture was stirred. The potassium carbonate was separated through filtration, and the resultant filtrate was poured into ice water. Hydrochloric acid was added to the resultant mixture so as to adjust the pH to 3, and then the mixture was subjected to extraction with chloroform twice. The resultant chloroform layer was washed with brine, and then dried over anhydrous sodium sulfate. The sodium sulfate was separated through filtration, and the resultant filtrate was concentrated to dryness under reduced pressure, followed by recrystallization, to thereby produce the target product (223 mg, yield: 72%).

Slightly yellow crystals, MS (ESI, m/z): 437(M$^-$), $^1$H-NMR (CDCl$_3$) δ 1.26(3H, t, J=7Hz), 1.37 to 1.45(2H, m), 1.46 to 1.55(2H, m), 1.63 to 1.71(2H, m), 1.78 to 1.86(2H, m), 2.32(2H, t, J=7 Hz), 3.93(3H, s), 3.96(3H, s), 4.02(2H, t, J=7 Hz), 4.13(2H, q, J=7 Hz), 6.91(1H, d, J=9 Hz), 6.95(2H, d, J=9 Hz), 7.13(1H, d, J=2 Hz), 7.23(1H, dd, J=2 Hz, 9 Hz), 7.36(1H, s), 7.85(2H, d, J=9 Hz)

Production of 4-[(Z)-1-cyano-2-(3,4-dimethoxy-phenyl)-vinyl]-phenyl 8-bromo-octanoate (Compound 67)

Compound 1 (1.41 g), 8-bromooctanoic acid (1.78 g), and p-toluenesulfonic acid (1.90 g) were dissolved in toluene, and the resultant solution was refluxed for 10 hours. The resultant solution was concentrated, and then purified by means of silica gel column chromatography, to thereby produce the target product (0.72 g, yield: 34%).

Pale yellow crystals, MS (APCI, m/z): 486 (MH$^+$), $^1$H-NMR (CDCl$_3$) δ 1.35 to 1.55(6H, m), 1.74 to 1.82(2H, m), 1.84 to 1.92(2H, m), 2.59(2H, t), 3.42(2H, t), 3.93(3H, s), 3.96(3H, s), 6.93(1H, d, J=9 Hz), 7.14(1H, d, J=2 Hz), 7.19(2H, d, J=9 Hz), 7.26(1H, dd, J=2 Hz, 9 Hz), 7.41(1H, s), 7.90 (2H, d, J=9 Hz)

Production of (Z)-3-(3-amino-phenyl)-2-(3,4-dimethoxy-phenyl)-acrylonitrile hydrochloride (Compound 68)

Compound 57 (500 mg) was suspended in hydrochloric acid (1.1 eq.), and 1,4-dioxane and acetonitrile were added to and dissolved in the resultant suspension. The resultant reaction mixture was concentrated to dryness under reduced pressure, followed by recrystallization, to thereby produce the target product (550 mg, yield: 97%).

Pale yellow crystals, MS (APCI, m/z): 486 (MH$^+$), $^1$H-NMR (DMSO-d6) δ 3.82(3H, s), 3.86(3H, s), 7.09(1H, d, J=9 Hz), 7.21(1H, brd), 7.28(1H, dd, J=2 Hz, 9 Hz), 7.36(1H, d, J=2 Hz), 7.49(1H, brt), 7.60(1H, brd), 7.64(1H, brd), 7.96(1H, s)

Production of mono-{4-[(Z)-2-cyano-2-(3,4-dimethoxy-phenyl)-vinyl]-2-methoxy-phenyl} sodium phosphate (Compound 69)

Compound 71 (119 mg) was dissolved in ethanol, and sodium methoxide was added to the resultant solution, followed by stirring for 12 hours. The resultant mixture was concentrated to dryness under reduced pressure, and then dissolved in water. The resultant solution was washed with ethyl acetate, and the resultant aqueous layer was freeze-dried, to thereby produce the target product (130 mg, yield: 98%).

Pale yellow crystals, MS (ESI, m/z): 390(M–2Na$^+$ H$^-$), $^1$H-NMR(D$_2$O)δ3.64(3H, s), 3.67(3H, s), 3.69(3H, s), 6.83 (1H, d, J=9 Hz), 6.97(1H, d, J=2 Hz), 7.02(1H, dd, J=2, 9 Hz), 7.14(1H, dd, J=2, 9 Hz), 7.36(1H, d, J=9 Hz), 7.39(1H, s), 7.43(1H, d, J=2 Hz)

Production of mono-{4-[(Z)-2-cyano-2-(3,4-dimethoxy-phenyl)-vinyl]-phenyl} phosphate (Compound 70)

Compound 1 (100 mg) and 4-(dimethylamino)pyridine (5 mg) were dissolved in acetonitrile (700 μL), and then cooled to −10° C. Subsequently, carbon tetrachloride (171 μL) and diisopropylethylamine (129 μL) were added to the resultant solution, and the resultant mixture was stirred for 0.5 hours. Thereafter, dibenzyl phosphite (117 μL) was added to the mixture, followed by stirring for 12 hours. After completion of reaction, 0.5 M potassium dihydrogenphosphate was added to the resultant reaction mixture, and then washed with ethyl acetate. The resultant organic layer was concentrated to dryness under reduced pressure, followed by purification by means of silica gel chromatography employing a chloroform/methanol system. The thus-purified product was dissolved in dichloromethane, and bromotrimethylsilane was added to the resultant solution, followed by stirring at 0° C. for two hours. After completion of reaction, water was added to the resultant reaction mixture, and the mixture was stirred for one hour. The resultant mixture was washed with ethyl acetate, and the resultant aqueous layer was freeze-dried, to thereby produce the target product (103 mg, yield: 80%).

Pale yellow crystals, MS (ESI, m/z): 360(M-H$^-$), $^-$H-NMR(DMSO-d6)δ3.81(3H, s), 3.86(3H, s), 7.06(1H, d, J=9 Hz), 7.25(1H, dd, J=2 Hz, 9 Hz), 7.30(2H, d, J=8 Hz), 7.31(1H, d, J=2 Hz), 7.88(1H, s), 7.89(2H, d, J=8 Hz)

Production of mono-{4-[(Z)-2-cyano-2-(3,4-dimethoxy-phenyl)-vinyl]-2-methoxy-phenyl} phosphate (Compound 71)

Compound 7 (111 mg) and 4-(dimethylamino)pyridine (5 mg) were dissolved in acetonitrile (700 μL), and then cooled to −10° C. Subsequently, carbon tetrachloride (171 μL) and diisopropylethylamine (129 μL) were added to the resultant solution, and the resultant mixture was stirred for 0.5 hours. Thereafter, dibenzyl phosphite (117 μL) was added to the mixture, followed by stirring for 12 hours. After completion of reaction, 0.5 M potassium dihydrogenphosphate was added to the resultant reaction mixture, and then washed with ethyl acetate. The resultant organic layer was concentrated to dryness under reduced pressure, followed by purification by means of silica gel chromatography employing a chloroform/methanol system. The thus-purified product was dissolved in dichloromethane, and bromotrimethylsilane was added to the resultant solution, followed by stirring at 0° C. for two hours. After completion of reaction, water was added to the resultant reaction mixture, and the mixture was stirred for one hour. The resultant mixture was washed with ethyl acetate, and the resultant aqueous layer was freeze-dried, to thereby produce the target product (119 mg, yield: 85%).

Pale yellow crystals, MS (ESI, m/z): 390 (M-H$^-$), $^1$H-NMR(DMSO-d6)δ3.81(3H, s), 3.85(3H, s), 3.86(3H, s), 7.08(1H, d, J=9 Hz), 7.26(1H, dd, J=2 Hz, 9 Hz), 7.33(1H, d, J=2 Hz), 7.42(1H, d, J=9 Hz), 7.48(1H, dd, J=2, 9 Hz), 7.66(1H, d, J=2 Hz), 7.93(1H, s)

Production of N-[3-[2-cyano-2-(3,4-dimethoxy-phenyl)-vinyl]-phenyl]-acetamide (Compound 72)

Compound 57 (50 mg) was acetylated with acetic anhydride and pyridine in accordance with a customary method, to thereby produce the target product (48 mg, yield: 84%).

Slightly yellow crystals, MS (ESI, m/z): 323 (MH$^+$), $^1$H-NMR (CDCl$_3$)δ 2.21(3H, s), 3.93(3H, s), 3.96(3H, s), 6.92(1H, d, J=9 Hz), 7.14(1H, d, J=2 Hz), 7.25(1H, dd, J=2 Hz, 9 Hz), 7.40(1H, t, J=8 Hz), 7.41(1H, s), 7.52(1H, brd), 7.61(2H, brd), 8.01(1H, brs)

Production of (Z)-2-(3,4-dimethoxyphenyl)-3-[4-(6-phospho-β-D-glucopyranosyl)-phenyl]-acrylonitrile (Compound 73)

Compound 44 (100 mg) and (2,2,2-trichloroethyl) phosphorochloridate (256 mg) were dissolved in pyridine (2 mL), and the resultant solution was stirred for two hours. After completion of reaction, the resultant reaction mixture was concentrated to dryness under reduced pressure, followed by purification by means of silica gel chromatography employing a chloroform/methanol system. The thus-purified product was dissolved in a pyridine-acetic acid (4:1) solvent mixture, and zinc powder (140 mg) was added to the resultant solution, followed by stirring for two hours. After completion of reaction, the resultant reaction mixture was concentrated to dryness under reduced pressure, followed by purification by means of silica gel chromatography employing a chloroform/methanol system, to thereby produce the target product (83 mg, yield: 70%).

Pale yellow crystals, MS (ESI, m/z): 522(MH$^+$), $^1$H-NMR (DMSO-d6) δ3.80(3H, s), 3.83(3H, s), 4.98(1H, d, J=7 Hz), 7.05(1H, d, J=9 Hz), 7.14(2H, d, J=9 Hz), 7.22(1H, dd, J=2 Hz, 9 Hz), 7.29(1H, d, J=2 Hz), 7.85(1H, s), 7.88(2H, d, J=9 Hz)

Production of sulphoric acid mono-{4-[(Z)-2-cyano-2-(3,4-dimethoxy-phenyl)-vinyl]-phenyl} ester triethylammonium salt (Compound 74)

Compound 1 (100 mg) was suspended in chloroform (10 mL), and triethylamine (516 μL) and sulfur trioxide-pyridine complex (588 mg) were added to the resultant suspension, followed by stirring for two hours. After completion of reaction, the resultant reaction mixture was concentrated to dryness under reduced pressure, followed by purification by means of silica gel chromatography employing a chloroform/methanol system, to thereby produce the target product (160 mg, yield: 97%).

Pale yellow crystals, MS (ESI, m/z): 360(M-(C$_2$H$_5$)$_3$NH$^-$), $^1$H-NMR(CDCl$_3$)δ1.29(9H, t, J=7 Hz), 3.18(6H, dd, J=7, 15 Hz), 3.86(3H, s), 3.90(3H, s), 7.01(1H, d, J=9 Hz), 7.27(2H, m), 7.39(2H, d, J=9 Hz), 7.69(1H, s), 7.90(2H, d, J=9 Hz)

Production of (Z)-2-(3,4-dimethoxyphenyl)-3-[4-(6-phospho-β-D-glucopyranosyl)-phenyl]-acrylonitrile sodium salt (Compound 75)

Compound 73 (83 mg) was dissolved in ethanol, and sodium methoxide was added to the resultant solution, followed by stirring for 12 hours. The resultant mixture was concentrated to dryness under reduced pressure, and the resultant product was dissolved in water. The resultant solution was washed with ethyl acetate, and the thus-obtained aqueous layer was freeze-dried, to thereby produce the target product (81 mg, yield: 90%).

Pale yellow crystals, MS (ESI, m/z): 522 (M−2Na$^+$ H$^−$), $^1$H-NMR(D$_2$O)δ3.53(3H, s), 3.58(3H, s), 3.86(1H, dd, J=6 Hz, 12 Hz), 4.01(1H, m), 4.97(1H, d, J=7 Hz), 6.60(1H, d, J=9 Hz), 6.70(1H, d, J=2 Hz), 6.81(1H, dd, J=2 Hz, 9 Hz), 6.94(2H, d, J=9 Hz), 7.06(1H, s), 7,43(2H, d, J=9 Hz)

Production of (Z)-2-(3,4-dimethoxy-phenyl)-3-(2-hydroxy-5-nitro-phenyl)-acrylonitrile (Compound 76)

The hydroxyl group of 2-hydroxy-5-nitrobenzaldehyde (1.00 g) was protected by use of 2-methoxyethoxymethoxyl chloride (0.75 g) in accordance with (production process 1), to thereby produce an MEM form (1.10 g, yield: 65%). The resultant MEM form (510 mg) and 3,4-dimethoxybenzyl cyanide (354 mg) were subjected to condensation in accordance with process B of (production process 2), to thereby produce (Z)-2-(3,4-dimethoxy-phenyl)-3-[2-(2-methoxy-ethoxymethoxy)-5-nitro-phenyl]-acrylonitrile (330 mg, yield: 40%). The thus-produced (Z)-2-(3,4-dimethoxy-phenyl)-3-[2-(2-methoxy-ethoxymethoxy)-5-nitro-phenyl]-acrylonitrile (200 mg) was subjected to deprotection in accordance with (production process 3), to thereby produce the target product (87 mg, yield: 55%).

Yellow-orange crystals, MS (ESI, m/z): 327(M-H$^−$), $^1$H-NMR (CDCl$_3$)δ 3.95(3H, s), 3.96(3H, s), 6.97(1H, d, J=9 Hz), 7.31(1H, d, J=2 Hz), 7.32(1H, dd, J=2 Hz, 9 Hz), 7.49(1H, d, J=9 Hz), 7.85(1H, s), 8.38(1H, dd, J=2 Hz, 9 Hz), 8.49(1H, d, J=2 Hz)

Production of (Z)-2-(3,4-dimethoxy-phenyl)-3-(4-fluoro-3-nitro-phenyl)-acrylonitrile (Compound 77)

4-Fluoro-3-nitrobenzaldehyde (507 mg) and 3,4-dimethoxybenzyl cyanide (532 mg) were subjected to condensation in accordance with process B of (production process 2), to thereby produce the target product (485 mg, yield: 30%).

Yellow-orange crystals, MS (ESI, m/z): 325 (M-H$^−$), $^1$H-NMR (CDCl$_3$)δ 3.95(3H, s), 3.97(3H, s), 6.95(1H, d, J=9 Hz), 7.14(1H, d, J=2 Hz), 7.29(1H, dd, J=2 Hz, 9 Hz), 7.40(1H, s), 7.41(1H, dd, J=9 Hz, 10 Hz), 8.25 to 8.32(1H, m), 8.42(1H, dd, J=2 Hz, 7 Hz)

Production of (Z)-2-(3,4-dimethoxy-phenyl)-3-(3-hydroxy-4,5-dimethoxy-phenyl)-acrylonitrile (Compound 78)

The hydroxyl group of 3-hydroxy-4,5-dimethoxybenzaldehyde (1.00 g) was protected by use of 2-methoxyethoxymethyl chloride (0.70 g) in accordance with (production process 1), to thereby produce an MEM form (1.40 g, yield: 95%). The resultant MEM form (1.45 g) and 3,4-dimethoxybenzyl cyanide (1.00 g) were subjected to condensation in accordance with process A of (production process 2), to thereby produce (Z)-3-[3,4-dimethoxy-5-(2-methoxyethoxymethoxy)-phenyl]-2-(3,4-dimethoxy-phenyl)-acrylonitrile (1.60 g, yield: 71%). The thus-produced (Z)-3-[3,4-dimethoxy-5-(2-methoxyethoxymethoxy)-phenyl]-2-(3,4-dimethoxy-phenyl)-acrylonitrile (1.60 g) was subjected to deprotection in accordance with (production process 3), to thereby produce the target product (0.74 g, yield: 56%).

Slightly yellow crystals, MS (APCI, m/z):342(MH$^+$), $^1$H-NMR(CDCl$_3$)δ3.93(3H, s), 3.95(3H, s), 3.96(3H, s), 3.98(3H, s), 6.92(1H, d, J=9 Hz), 6.97(1H, d, J=2 Hz), 7.13(1H, d, J=2 Hz), 7.24(1H, dd, J=2 Hz, 9 Hz), 7.27(1H, d, J=2 Hz), 7.29(1H, s)

Production of (Z)-2-(3,4-dimethoxy-phenyl)-3-(4-hydroxy-3,5-dimethoxy-phenyl)-acrylonitrile (Compound 79)

The hydroxyl group of 4-hydroxy-3,5-dimethoxybenzaldehyde (2.44 g) was protected by use of 2-methoxyethoxymethyl chloride (1.67 g) in accordance with (production process 1), to thereby produce an MEM form (3.40 g, yield: 94%). The resultant MEM form (3.40 g) and 3,4-dimethoxybenzyl cyanide (2.23 g) were subjected to condensation in accordance with process A of (production process 2), to thereby produce (Z)-3-[3,5-dimethoxy-4-(2-methoxyethoxymethoxy)-phenyl]-2-(3,4-dimethoxy-phenyl)-acrylonitrile (3.53 g, yield: 65%). The thus-produced (Z)-3-[3,5-dimethoxy-4-(2-methoxyethoxymethoxy)-phenyl]-2-(3,4-dimethoxy-phenyl)-acrylonitrile (0.35 g) was subjected to deprotection in accordance with (production process 3), to thereby produce the target product (0.25 g, yield: 90%).

Slightly yellow crystals, MS (APCI, m/z):342 (MH$^+$), $^1$H-NMR(CDCl$_3$)δ3.93(3H, s), 3.97(3H, s), 3.97(6H, s), 6.92(1H, d, J=9 Hz), 7.13(1H, d, J=2 Hz), 7.22(2H, s), 7.24(1H, dd, J=2 Hz, 9 Hz), 7.32(1H, s)

Example 2

Establishment of SN-38-resistant A549 Cell Line

Human non-small cell lung cancer A549 cell line was subcultured at 5% CO$_2$ and 37° C. by use of a Ham's F-12 medium containing 10% FBS, 100 U/mL of penicillin, and 100 μg/mL of streptomycin (10% FBS/Ham's F-12). SN-38-resistant A549 cell lines were selected by subculturing the A549 cell line in a medium for two months while the concentration of SN-38 contained in the medium was increased in a stepwise manner (4 to 10 ng/mL). Subsequently, the resultant SN-38-resistant A549 cell lines were subjected to cloning by means of limiting dilution, to thereby establish six cloned SN-38-resistant A549 cell lines (A549/SN-38-1 to 6).

Example 3

Anticancer Drug Sensitivity Test of A549/SN-38 Cell Line

Figure 1B:
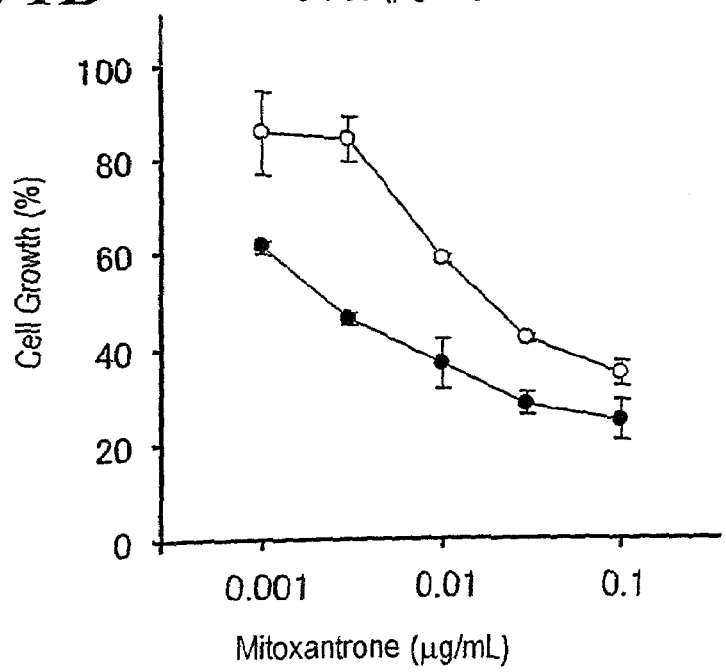

The A549 cell line or each of the A549/SN-38-1 to 6 was suspended in 10% FBS/Ham's F-12, and the resultant suspension was inoculated into a 96-well microplate, followed by culturing at 5% CO$_2$ and 37° C. overnight. Thereafter, a solution of an anticancer drug in 10% FBS/Ham's F-12 (50 μL) was added to each of the wells, followed by culturing at 5% CO$_2$ and 37° C. for 48 hours. After completion of culturing, the number of viable cells was counted by use of a viable cell counting reagent [TetraColor ONE (trade name), product of Seikagaku Corporation] according to the attached instruction manual. Table 2 and FIG. 1 show the sensitivities of the A549 cell line and the six A549/SN-38 cell lines to various anticancer drugs. "IC$_{50}$" corresponds to the concentration of an anticancer drug required for 50% inhibition of cell growth. "Relative resistance value" is obtained by dividing the IC$_{50}$ for an A549/SN-38 cell line by the IC$_{50}$ for the A549 cell line. The greater the relative resistance value, the higher the level of acquired resistance. The A549/SN-38 cell lines exhibited particularly strong resistance to SN-38 and mitoxantrone, which are BCRP substrates.

lines. These results suggest that BCRP is involved in the anticancer drug resistance mechanism of the A549/SN-38 cell lines. Through the above RT-PCR analysis, expression of BCRP was found in the human breast cancer MCF-7 cell

TABLE 2

| Anticancer drug | A549 | A549/SN-38 | | | | | |
|---|---|---|---|---|---|---|---|
| | | 1 | 2 | 3 | 4 | 5 | 6 |
| | | $IC_{50}$ µg/mL (Relative resistance value) | | | | | |
| SN-38 | 0.013 | 0.12 (9.2) | 0.10 (7.5) | 0.13 (9.7) | 0.10 (7.7) | 0.10 (7.7) | 0.10 (7.4) |
| Paclitaxel | 0.0049 | 0.0098 (2.0) | 0.012 (2.4) | 0.013 (2.7) | 0.014 (2.8) | 0.0061 (1.2) | 0.0071 (1.4) |
| Etoposide | 0.90 | 0.27 (0.3) | 0.80 (1.0) | 1.6 (1.9) | 3.5 (4.0) | 2.3 (2.7) | 1.0 (1.1) |
| Cisplatin | 18.6 | 15.1 (0.8) | 16.5 (0.9) | 15.1 (0.8) | 17.0 (0.9) | 15.9 (0.9) | 16.8 (0.9) |
| 5-Fluorouracil | 2.1 | 4.3 (2.0) | 1.3 (0.6) | 0.69 (0.3) | 0.91 (0.4) | 1.7 (0.8) | 1.0 (0.5) |
| Gemcitabine | 0.0090 | 0.0039 (0.4) | 0.0053 (0.6) | 0.0040 (0.4) | 0.0032 (0.4) | 0.0040 (0.4) | 0.0040 (0.4) |
| Doxorubicin | 0.10 | 0.19 (1.9) | 0.14 (1.4) | 0.12 (1.3) | 0.22 (2.3) | 0.057 (0.6) | 0.049 (0.5) |
| Mitomycin C | 0.11 | 0.13 (1.2) | 0.11 (1.1) | 0.0029 (0.3) | 0.15 (1.4) | 0.11 (1.0) | 0.047 (0.4) |

Example 4

RT-PCR Analysis of A549/SN-38 Cell Line

Figure 2:
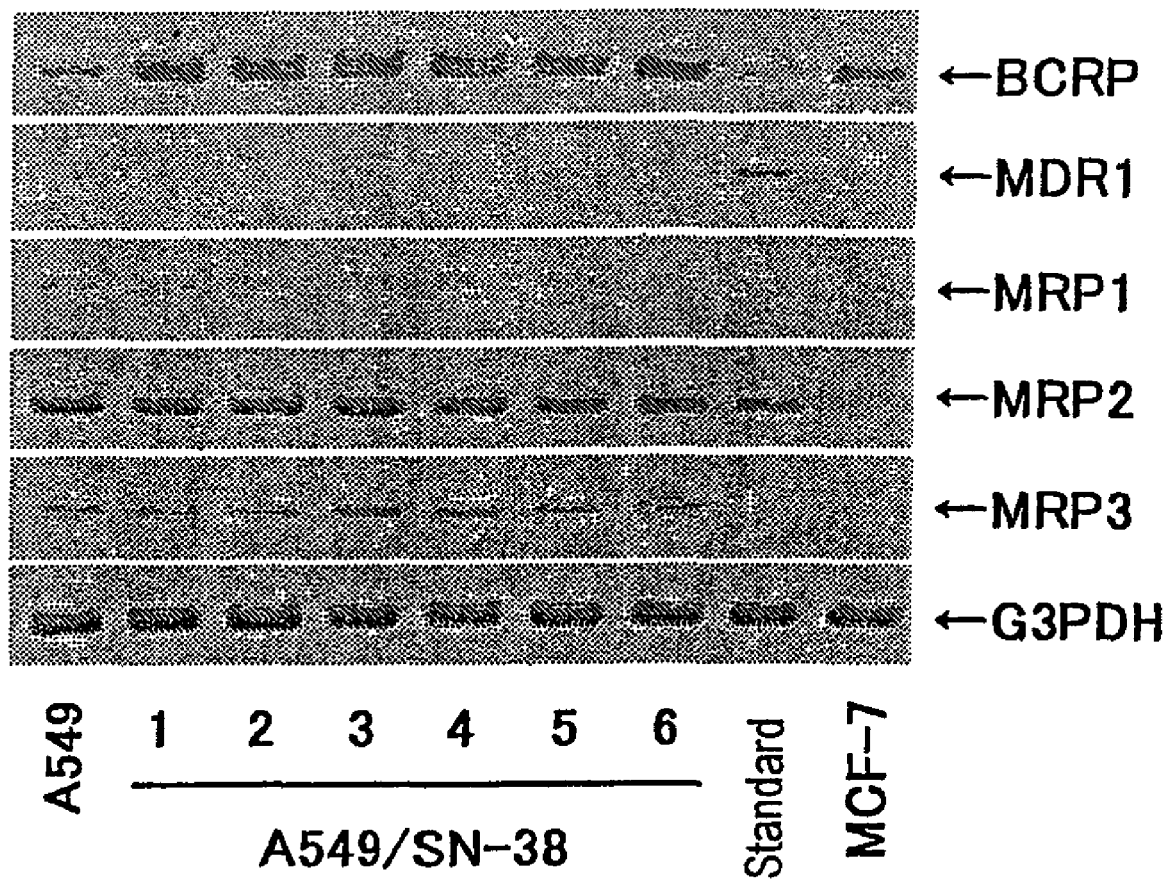
FIG. 2 shows the results of RT-PCR analysis of expression of mRNAs of various drug transporters in A549 cell line and A549/SN-38 cell lines.

RT-PCR was performed for analyzing the expression of mRNA of a drug transporter in the A549 cell line, the six A549/SN-38 cell lines, and human breast cancer MCF-7 cell line, which is known to express BCRP. The total RNA was extracted from cells by use of an RNA extraction reagent [ISOGEN (trade name), product of Nippon Gene Co., Ltd.], and RT-PCR was performed by use of an RT-PCR reagent [Ready To Go RT-PCR Beads (trade name), product of Amersham pharmacia biotech] and a thermal cycler [iCycler (trade mane), product of BIO-RAD] according to the attached instruction manual (total RNA: 0.5 µg). The resultant PCR product was subjected to electrophoresis by use of 2% agarose gel, and then staining with ethidium bromide, followed by detection by use of a transilluminator. In addition, real-time RT-PCR was performed by use of a real-time RT-PCR reagent [SYBR Green RT-PCR Reagents (trade name), product of Applied Biosystems] and a sequence detection system [ABI PRISM 7000 (trade name), product of Applied Biosystems] according to the attached instruction manual, for quantitative analysis (total RNA: 0.1 µg). PCR primers corresponding to BCRP, MDR1, MRP1, MRP2, MRP3, and G3PDH (endogenous control gene) were designed on the basis of the following known mRNA base sequences (accession Nos. AF098951, AF016535, L05628, U63970, AF009670, and M33197), respectively. FIG. 2 shows the results of the RT-PCR, and FIG. 3 shows the results of the real-time RT-PCR. Expression of BCRP was remarkably increased in all the six A549/SN-38 cell lines, as compared with the case of the A549 cell line. In contrast, no significant difference was observed in the level of expression of MRP2 (whose substrate is SN-38, which is also a BCRP substrate) between the A549 cell line and the A549/SN-38 cell lines. Meanwhile, no significant difference was observed in the level of expression of the other drug transporters between the A549 cell line and the A549/SN-38 cell lines. In addition to the studies on expression of the aforementioned drug transporters, expression of topoisomerase-I, topoisomerase-II, Bcl-2, Bax, or IκBα was studied by means of western blotting, and topoisomerase-I activity was studied on the basis of DNA relaxation reaction. However, there were not obtained data suggesting that these proteins are involved in the anticancer drug resistance mechanism of the A549/SN-38 cell lines.

Example 5

Amount of Anticancer Drug Accumulated in A549/SN-38 Cell Line

The A549 cell line or the A549/SN-38-4 cell line (4×10$^6$ cells/mL) was suspended in 10% FBS/RPMI1640 (1 mL), and an SN-38 DMSO solution (1 µL, final concentration: 300 ng/mL) was added to the resultant suspension, followed by incubation at 37° C. for 60 minutes. Thereafter, centrifugation was performed (2° C., 1,400×g, 1 min), and the resultant supernatant was removed. Ice-cooled PBS was added to the thus-precipitated cells, and the cells were resuspended therein, followed by centrifugation (2° C., 1,400×g, 1 min) for washing of the cells. This washing procedure was performed again, followed by addition of PBS (375 µL) and sonication of the cells. To the resultant cell sonicate, methanol (375 µL) and 10% zinc sulfate solution (15 µL) were added, and the resultant mixture was stirred, followed by centrifugation (2° C., 12,500×g, 5 min) and collection of the supernatant. The thus-collected supernatant was dispensed in a white 96-well microplate for fluorescence intensity measurement (200 µ/well), and then the amounts of SN-38 and an SN-38-glucuronide contained in the supernatant were measured by use of a microplate fluorometer [SPECTRA max GEMINI XS (trade name), product of Molecular Devices] (SN-38: excitation wavelength 380 nm, emission wavelength 560 nm; SN-38-glucuronide: excitation wavelength 370 nm, emission wavelength 430 nm), to thereby calculate the amount of intracellular accumulation of SN-38 and the glucuronide. As is clear from the results shown in FIG. 4, the amount of SN-38 accumulated in the A549/SN-38-4 cell line is about 1/5 that of SN-38 accumulated in the A549 cell line. The results support that BCRP is involved in the anticancer drug resistance mechanism of the A549/SN-38 cell lines. In contrast, virtually no SN-38-glucuronide was detected in both the A549 cell line and the A549/SN-38-4 cell line, indicating that glucuronidation is not involved in the anticancer drug resistance mechanism.

Example 6

Figure 5A:
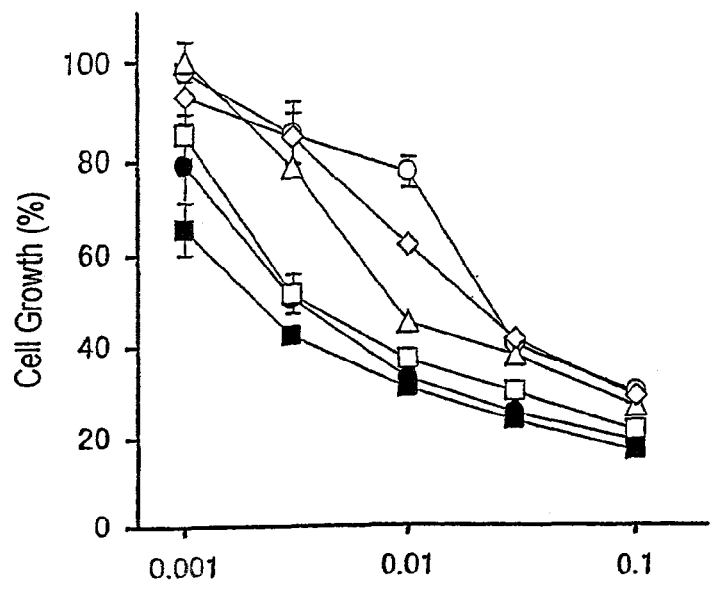
FIG. 5 shows the effect of a diphenylacrylonitrile derivative (compound 1) in overcoming SN-38 resistance (A) and mitoxantrone resistance (B) of A549/SN-38-4 cell line.
Figure 5B:
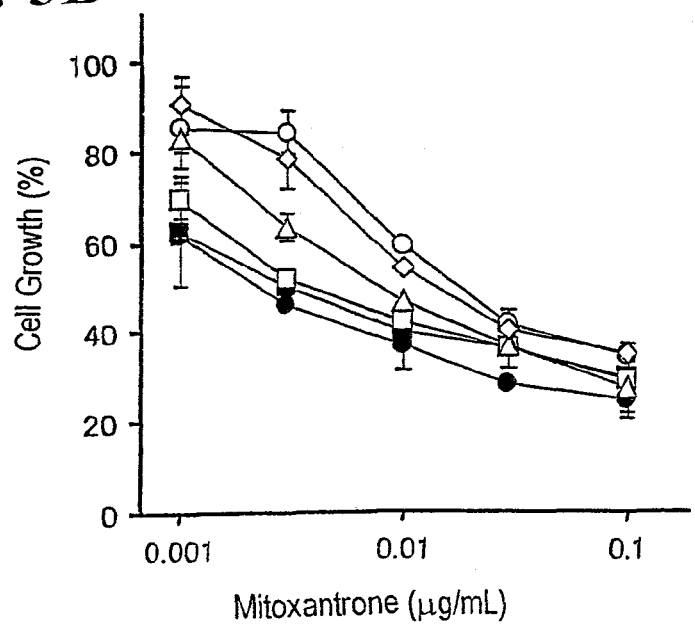

Effect of Diphenylacrylonitrile Derivative in Overcoming Anticancer Drug Resistance of A549/SN-38-4 Cell Line The effect of a diphenylacrylonitrile derivative on BCRP-mediated anticancer drug resistance was studied by use of the human lung cancer A549/SN-38-4 cell line, which had acquired anticancer drug resistance through BCRP expression. The human lung cancer A549 cell line or the A549/SN-38-4 cell line was suspended in 10% FBS/Ham's F-12, and the resultant suspension was inoculated into a 96-well microplate, followed by culturing at 5% $CO_2$ and 37° C. overnight ($2 \times 10^3$ cells/50 µL/well). Thereafter, a 10% FBS/Ham's F-12 solution (25 µL) containing a diphenylacrylonitrile derivative and SN-38 or mitoxantrone was added to each of the wells, followed by culturing at 5% $CO_2$ and 37° C. for 48 hours. After completion of culturing, the number of viable cells was counted by use of TetraColor ONE according to the attached instruction manual. FIG. 5 shows the effect of the diphenylacrylonitrile derivative (compound 1) in overcoming SN-38 resistance or mitoxantrone resistance, and Table 3 shows the SN-38 resistance overcoming effect of each of the tested diphenylacrylonitrile derivatives, which is represented by $EC_{50}$. "$EC_{50}$" corresponds to the concentration of a diphenylacrylonitrile derivative required for 50% reduction of the relative resistance value. The relative resistance value is obtained by dividing the $IC_{50}$ (i.e., the concentration of an anticancer drug required for 50% inhibition of cell growth) for the A549/SN-38-4 cell line by the $IC_{50}$ for the A549 cell line. The greater the relative resistance value, the higher the level of acquired resistance. The results reveal that each of the diphenylacrylonitrile derivatives exhibits potent effect of overcoming the SN-38 resistance or mitoxantrone resistance of the A549/SN-38-4 cell line. When the concentration of the diphenylacrylonitrile derivative falls within the range such that the derivative overcomes the anticancer drug resistance in a concentration-dependent manner, the diphenylacrylonitrile derivative per se does not affect growth of the A549 cell line and the A549/SN-38-4 cell line. The results suggest that the diphenylacrylonitrile derivative of the present invention inhibits BCRP, and overcomes the anticancer drug resistance of cancer cells.

TABLE 3

| Compound | Resistance overcoming effect $EC_{50}$ (µg/mL) |
| --- | --- |
| 1 | 0.051 |
| 2 | 0.41 |
| 3 | 0.020 |
| 4 | 0.079 |
| 5 | 0.021 |
| 6 | 0.098 |
| 7 | 0.025 |
| 8 | 0.035 |
| 9 | 0.028 |
| 10 | 0.023 |
| 11 | 0.047 |
| 12 | 0.28 |
| 13 | 0.013 |
| 14 | 0.047 |
| 15 | 0.023 |
| 16 | 0.098 |
| 17 | 0.018 |
| 18 | 0.0063 |
| 19 | 0.019 |
| 20 | 0.053 |
| 21 | 0.022 |
| 22 | 0.022 |
| 23 | 0.048 |
| 24 | 0.0073 |
| 25 | <0.005 |
| 26 | <0.005 |
| 27 | 0.047 |
| 28 | 0.011 |
| 29 | 0.10 |
| 30 | 0.041 |
| 31 | 0.015 |
| 32 | 0.15 |
| 33 | 0.019 |
| 34 | 0.079 |
| 35 | 0.37 |
| 36 | 0.20 |
| 37 | 0.085 |
| 38 | 0.037 |
| 39 | 0.027 |
| 40 | 0.15 |
| 41 | 0.041 |
| 42 | 0.038 |
| 43 | 0.12 |
| 44 | 0.024 |
| 45 | 0.13 |
| 46 | 0.58 |
| 47 | 0.053 |
| 48 | 0.013 |
| 49 | 0.20 |
| 50 | 0.094 |
| 51 | 0.045 |
| 52 | 0.024 |
| 53 | 0.048 |
| 54 | 0.26 |
| 55 | 0.015 |
| 56 | 0.016 |
| 57 | 0.037 |
| 58 | 0.033 |
| 59 | 0.043 |
| 60 | 0.064 |
| 61 | 0.024 |
| 62 | 0.11 |
| 63 | 0.024 |
| 64 | 0.010 |
| 65 | 0.20 |
| 66 | 0.71 |
| 67 | 0.065 |
| 68 | 0.048 |
| 69 | 0.13 |
| 70 | 0.24 |
| 71 | 0.29 |
| 72 | 0.028 |
| 73 | 1.0 |
| 74 | >1.0 |
| 75 | >1.0 |
| 76 | 0.82 |
| 77 | 0.30 |
| 78 | 0.053 |
| 79 | 0.017 |

Example 7

Effect of Diphenylacrylonitrile Derivative in Enhancing Sensitivity of MCF-7 Cell Line to Anticancer Drug The effect of a diphenylacrylonitrile derivative on the sensitivity of cancer cells to an anticancer drug was studied by use of human breast cancer MCF-7 cell line, which is known to express BCRP (Blood 99, 3763-3770 (2002)). The MCF-7 cell line was suspended in 10% FBS/RPMI1640, and the resultant suspension was inoculated into a 96-well microplate, followed by culturing at 5% $CO_2$ and 37° C. overnight ($3 \times 10^3$ cells/50 µL/well). Thereafter, a solution of a diphenylacrylonitrile derivative and SN-38 in 10% FBS/RPMI1640 (25 µL) was added to each of the wells, followed by culturing at 5% $CO_2$ and 37° C. for 48 hours. After completion of culturing, the number of viable cells was counted by use of TetraColor ONE according to the attached instruction manual. Table 4 shows change in the sensitivity of the MCF-7 cell line to SN-38, which change is caused by a diphenylacrylonitrile derivative, by use of $IC_{50}$ (i.e., the concentration of SN-38 required for 50% inhibition of cell growth). The results reveal that each of the tested diphenylacrylonitrile derivatives enhances the sensitivity of the MCF-7 cell line to SN-38. When the concentration of the diphenylacrylonitrile derivative falls within the range such that the derivative enhances the SN-38 sensitivity in a concentration-dependent manner, the diphenylacrylonitrile derivative per se does not affect growth of the MCF-7 cell line. The results suggest that the diphenylacrylonitrile derivative of the present invention inhibits BCRP, and enhances the sensitivity of cancer cells to an anticancer drug.

TABLE 4

| Compound | Compound concentration (µg/mL) | | |
|---|---|---|---|
| | 0 | 0.1 | 1.0 |
| | SN-38: $IC_{50}$ (µg/mL) | | |
| 1 | 0.021 | 0.010 | 0.0048 |
| 3 | 0.012 | 0.011 | 0.0026 |
| 4 | 0.011 | 0.0083 | 0.0023 |
| 5 | 0.014 | 0.015 | 0.0042 |
| 6 | 0.020 | 0.015 | 0.010 |
| 7 | 0.017 | 0.013 | 0.0041 |
| 8 | 0.022 | 0.026 | 0.010 |
| 9 | 0.027 | 0.012 | 0.0060 |
| 11 | 0.012 | 0.0032 | 0.0032 |
| 13 | 0.016 | 0.0066 | 0.0058 |

Example 8

Figure 6A:
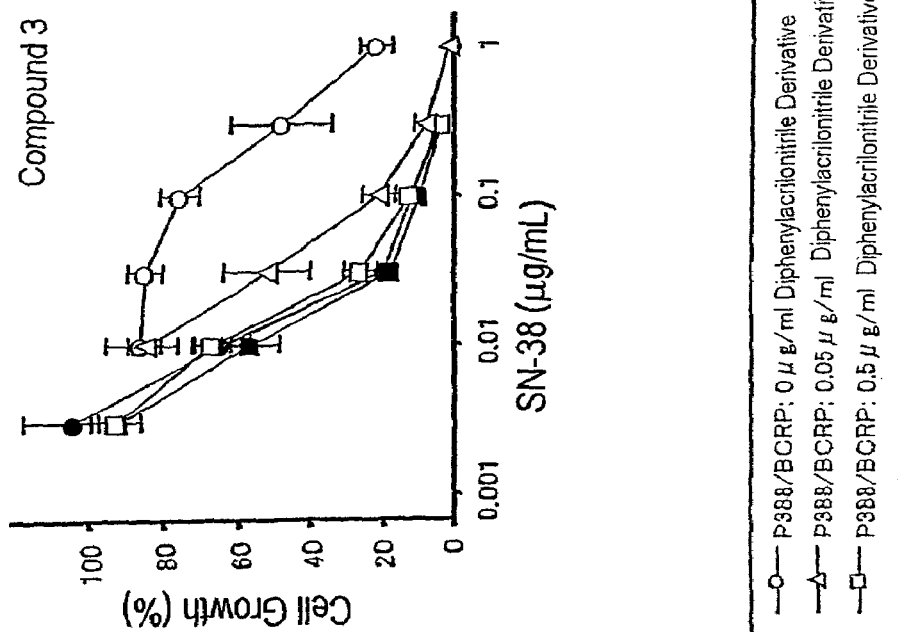
FIG. 6 shows the effect of diphenylacrylonitrile derivatives [compound 1 (A), compound 3 (B), compound 4 (C), compound 5 (D), compound 7 (E), and compound 13 (F)] in overcoming SN-38 resistance of P388/BCRP cell line.
Figure 6B:
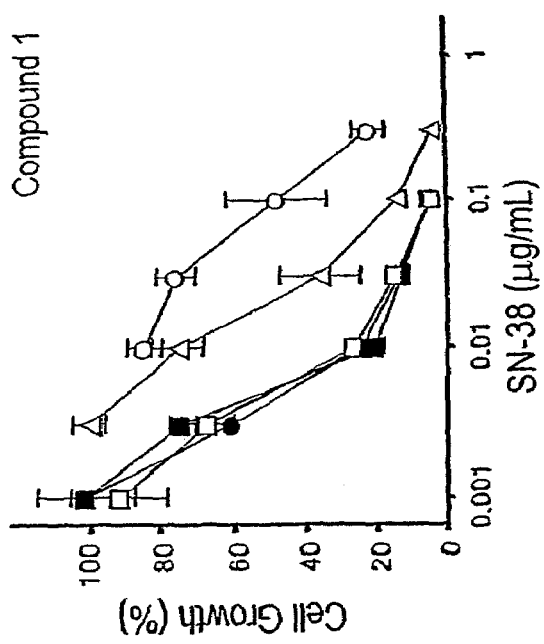

Effect of Diphenylacrylonitrile Derivative in Overcoming Anticancer Drug Resistance of Human BCRP Transduced Mouse Leukemia P388 Cell Line Mouse leukemia P388 cell line or human BCRP transduced P388 cell line (P388/BCRP cell line, obtained from Yoshikazu Sugimoto, The Cancer Chemotherapy Center of Japanese Foundation for Cancer Research) was suspended in 10% FBS/RPMI1640, and the resultant suspension was inoculated into a 96-well microplate ($1 \times 10^4$ cells/50 µL/well). Thereafter, a solution of a diphenylacrylonitrile derivative and SN-38 in 10% FBS/RPNI1640 (25 µL) was added to each of the wells, followed by culturing at 5% $CO_2$ and 37° C. for 48 hours. After completion of culturing, the number of viable cells was counted by use of TetraColor ONE according to the attached instruction manual. The results are shown in FIG. 6. Each of the tested diphenylacrylonitrile derivatives exhibited potent effect of overcoming the SN-38 resistance of the P388/BCRP cell line. In contrast, the diphenylacrylonitrile derivative did not affect the sensitivity of the P388 cell line to SN-38. The results demonstrate that the diphenylacrylonitrile derivative of the present invention has BCRP-inhibiting effect.

Example 9

Effect of Diphenylacrylonitrile Derivative on Multidrug Resistance of MES-SA/Dx5 Cell Line Human uterine cancer MES-SA cell line or MES-SA/Dx5 cell line which had acquired multidrug resistance through overexpression of P-glycoprotein [Cancer Res. 45, 4091-4096 (1985)] was suspended in 10% FBS/DMEM, and the resultant suspension was inoculated into a 96-well microplate, followed by culturing at 5% $CO_2$ and 37° C. overnight ($3 \times 10^3$ cells/50 µL/well). Thereafter, a solution of a diphenylacrylonitrile derivative and paclitaxel in 10% FBS/DMEM (25 µL) was added to each of the wells, followed by culturing at 5% $CO_2$ and 37° C. for 48 hours. After completion of culturing, the number of viable cells was counted by use of TetraColor ONE according to the attached instruction manual. Table 5 shows the effect of each of the tested diphenylacrylonitrile derivatives on multidrug resistance by use of $EC_{50}$. "$EC_{50}$" corresponds to the concentration of a diphenylacrylonitrile derivative required for 50% reduction of the relative resistance value. The results revealed that when the concentration of the diphenylacrylonitrile derivative falls within the range employed for the test, the derivative does not affect the paclitaxel resistance of the MES-SA/Dx5 cell line. In addition, the diphenylacrylonitrile derivative per se did not affect growth of the MES-SA cell line and the MES-SA/Dx5 cell line. The results indicate that the diphenylacrylonitrile derivative of the present invention does not act on P-glycoprotein, and has BCRP specificity.

TABLE 5

| Compound | Resistance overcoming effect $EC_{50}$ (µg/mL) |
|---|---|
| 1 | >1.0 |
| 2 | >1.0 |
| 3 | >1.0 |
| 4 | >1.0 |
| 5 | >1.0 |
| 6 | >1.0 |
| 7 | >1.0 |
| 8 | >1.0 |
| 9 | >1.0 |
| 10 | >1.0 |
| 11 | >1.0 |
| 12 | >1.0 |
| 13 | >1.0 |
| 14 | >1.0 |
| 15 | >1.0 |
| 16 | >1.0 |

Example 10

Figure 7:
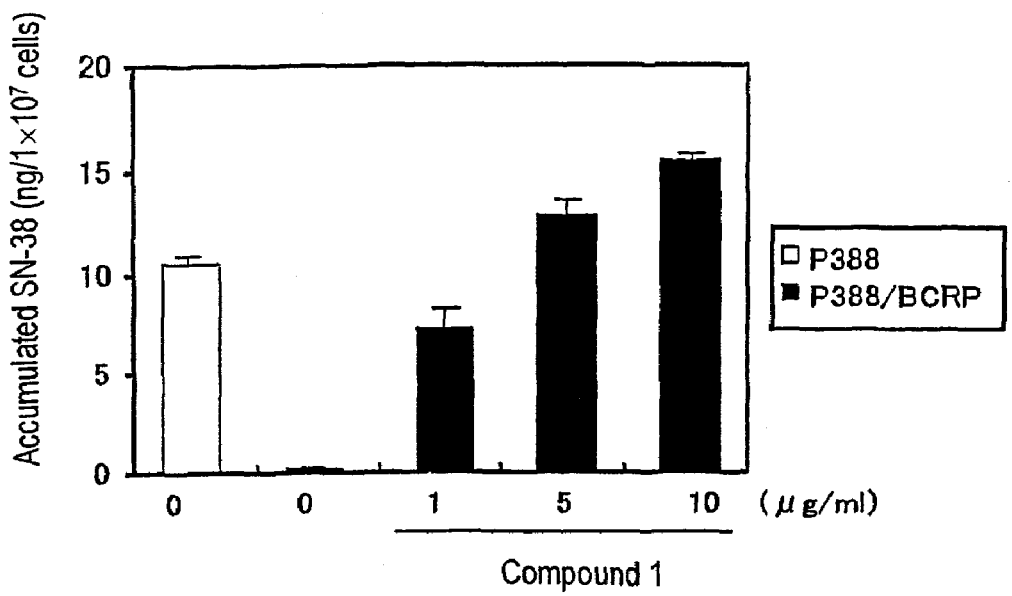
FIG. 7 shows the effect of a diphenylacrylonitrile derivative (compound 1) in increasing accumulation of SN-38 in P388/BCRP cell line.
Figure 8:
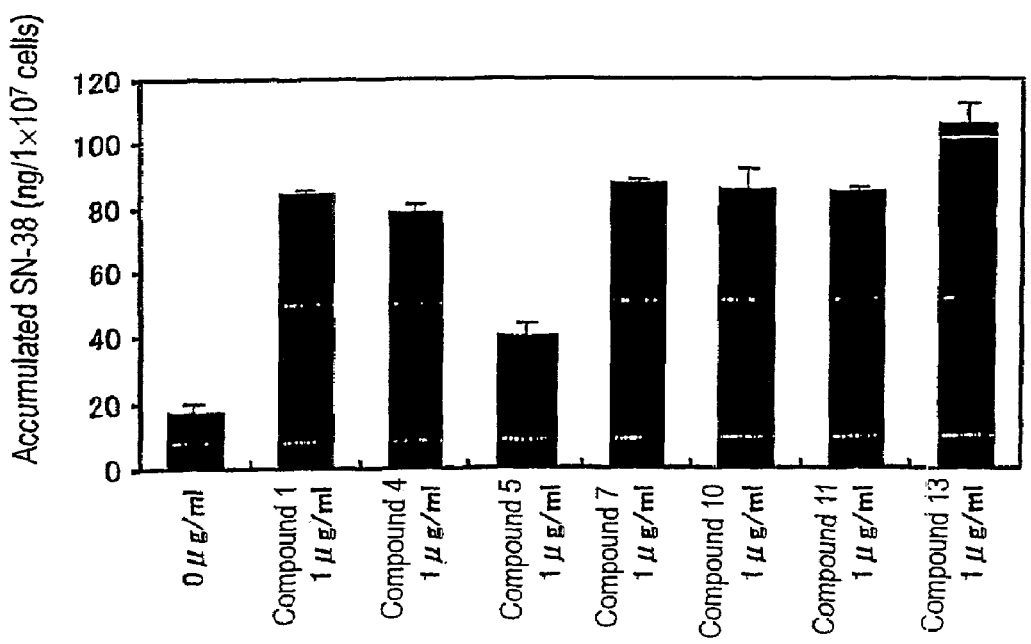
FIG. 8 shows the effect of different diphenylacrylonitrile derivatives in increasing accumulation of SN-38 in MCF-7 cell line.

Effect of Diphenylacrylonitrile Derivative on Amount of Anticancer Drug Accumulated in BCRP-expressing cell Line The P388 cell line or the P388/BCRP cell line ($1\times10^7$ cells/mL), or the MCF-7 cell line ($3\times10^6$ cells/mL) was suspended in 10% FBS/RPMI1640 (1 mL), and a diphenylacrylonitrile derivative and SN-38 (final concentration: 500 ng/mL) were added to the resultant suspension, followed by incubation at 37° C. for 60 minutes. Thereafter, centrifugation was performed (2° C., 1,400×g, 1 min), and the resultant supernatant was removed. Ice-cooled 10% FBS/RPMI1640 was added to the thus-precipitated cells, and the cells were resuspended therein, followed by centrifugation (2° C., 1,400×g, 1 min) for washing of the cells. This washing procedure was performed again, followed by addition of PBS (375 μL) and sonication of the cells. To the resultant cell sonicate, methanol (375 μL) and 10% zinc sulfate solution (15 μL) were added, and the resultant mixture was stirred, followed by centrifugation (2° C., 12,500×g, 5 min) and collection of the supernatant. The thus-collected supernatant was dispensed in a white 96-well microplate for fluorescence intensity measurement (200 μL/well), and then the amount of SN-38 contained in the supernatant was measured by use of a microplate fluorometer (SN-38: excitation wavelength 380 nm, emission wavelength 560 nm), to thereby calculate the amount of intracellular accumulation of SN-38. As is clear from the results shown in FIG. 7, the diphenylacrylonitrile derivative of the present invention increases the amount of accumulation of SN-38 in the P388/BCRP cell line. In addition, as is clear from the results shown in FIG. 8, the diphenylacrylonitrile derivative of the present invention increases the amount of accumulation of SN-38 in the MCF-7 cell line. The results suggest that the diphenylacrylonitrile derivative of the present invention inhibits BCRP, and increases the amount of intracellular accumulation of an anticancer drug.

Example 11

Effect of Diphenylacrylonitrile Derivative in Overcoming Anticancer Drug Resistance in vivo Groups of six-week-old female $CDF_1$ mice, each group consisting of 5 mice, were employed. The P388 cell line or the P388/BCRP cell line ($1\times10^6$ cells/mouse) was implanted into the peritoneal cavity of each of the mice. From one day to 10 days after the tumor implantation, a diphenylacrylonitrile derivative and irinotecan hydrochloride (CPT-11) were administered intraperitoneally once a day (total number of administration: 10). Before administration, the diphenylacrylonitrile derivative was dissolved or suspended in saline or in a mixture of ethanol, polyoxyethylene (20) sorbitan monooleate [Tween 80 (trade name), product of Tokyo Kasei Kogyo Co., Ltd.], and 5% glucose (ethanol/Tween 80/5% glucose=5:5:90 or 5:7.5:87.5), and CPT-11 was dissolved in saline. Merely the solvent was administered to mice in the control group. In order to evaluate the antitumor effect of the diphenylacrylonitrile derivative, survival rate T/C (%) was calculated from the survival days of the tumor-implanted mice by use of the following formula.

Survival rate T/C (%)=(the mean survival days of mice in the treated group)÷(the mean survival days of mice in the control group)×100

The results are shown in Tables 6, 7, and 8. The results reveal that the diphenylacrylonitrile derivative of the present invention inhibits BCRP in vivo, and exhibits the effect of overcoming anticancer drug resistance.

TABLE 6

| Compound | Dose (mg/kg/day) Compound | Dose (mg/kg/day) CPT-11 | Survival days Mean ± S.D. | T/C (%) |
|---|---|---|---|---|
| 1 | 100 | 20 | 19.4 ± 1.1 | 162 |
| 3 | 100 | 20 | 19.8 ± 0.8 | 165 |
| 5 | 100 | 20 | 19.2 ± 1.1 | 160 |
| 7 | 100 | 20 | 20.0 ± 0.7 | 167 |
| 8 | 100 | 20 | 19.2 ± 0.8 | 160 |
| 11 | 100 | 20 | 19.4 ± 0.5 | 162 |
| 13 | 100 | 20 | 20.6 ± 0.9 | 172 |
| 16 | 100 | 20 | 19.2 ± 0.4 | 160 |
| Solvent | 0 | 20 | 14.6 ± 0.5 | 122 |
| Solvent | 0 | 0 | 12.0 ± 0.7 | 100 |

TABLE 7

| Compound | Dose (mg/kg/day) Compound | Dose (mg/kg/day) CPT-11 | Survival days Mean ± S.D. | T/C (%) |
|---|---|---|---|---|
| 57 | 100 | 20 | 18.8 ± 0.8 | 145 |
| 68 | 100 | 20 | 18.8 ± 2.9 | 145 |
| Solvent | 0 | 20 | 12.8 ± 0.4 | 98 |
| Solvent | 0 | 0 | 13.0 ± 1.2 | 100 |

TABLE 8

| Compound | Dose (mg/kg/day) Compound | Dose (mg/kg/day) CPT-11 | Survival days Mean ± S.D. | T/C (%) |
|---|---|---|---|---|
| 60 | 100 | 20 | 20.2 ± 0.8 | 151 |
| 69 | 100 | 20 | 19.0 ± 2.3 | 142 |
| Solvent | 0 | 20 | 12.8 ± 0.4 | 96 |
| Solvent | 0 | 0 | 13.4 ± 0.5 | 100 |

Example 12

The following ingredients were mixed together, and the resultant mixture was formed into tablets.

TABLE 9

| | |
|---|---|
| Compound 1 | 100 mg |
| Lactose | 100 mg |
| Potato starch | 39 mg |
| Microcrystalline cellulose | 30 mg |
| Synthetic aluminum silicate | 30 mg |
| Calcium stearate | 1 mg |
| Total (for one tablet) | 300 mg |

The diphenylacrylonitrile derivative of the present invention, which exhibits BCRP-inhibiting effect, can overcome BCRP-mediated anticancer drug resistance. In addition, the diphenylacrylonitrile derivative can enhance the effect of an anticancer drug on BCRP-expressing cancer. Furthermore, the diphenylacrylonitrile derivative is envisaged to improve the bioavailability of an anticancer drug, and to improve the performance of cancer chemotherapy.

The invention claimed is:

1. A method of inhibiting a breast cancer resistance protein (BCRP) comprising administering to a patient an effective amount of a diphenylacrylonitrile derivative represented by the following formula (1) or a salt thereof:

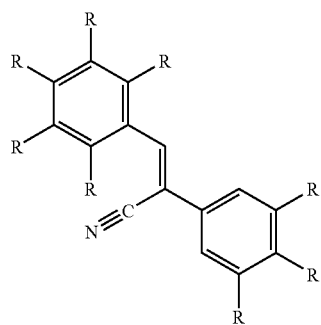

wherein, each of 8 R's, which are the same or different from one another, represents a hydrogen atom, a hydroxyl group, a nitro group, an amino group, an acetylamino group (—NHCOCH$_3$ group), a cyano group (—CN group), a formyl group (—CHO group), —COOR$_1$ (R$_1$ is hydrogen or C$_1$-C$_4$ alkyl), —O(CH$_2$)$_n$COOR$_2$ (n=1-7: R$_2$ is hydrogen or C$_1$-C$_4$ alkyl), —OOCCH$_2$CH$_2$COOR$_3$ (R$_3$ is hydrogen, C$_1$-C$_4$ alkyl, (Z)-2-(3,4-dimethoxy-phenyl)-3-(4-hydroxy-phenyl)-acrylonitrile, or glycopyranosyl), a C$_1$-C$_8$ alkoxy group, a C$_1$-C$_4$ alkyl group, a halogen atom, a C$_1$-C$_4$ alkoxy C$_1$-C$_4$ alkoxy C$_1$-C$_4$ alkoxy group, a C$_2$-C$_8$ acyloxy group, a C$_2$-C$_8$ halogenoacyloxy group, a methylenedioxy group, a trifluoromethyl group, a phosphate group (—OP(O)(OH)$_2$) or a salt thereof, a sulfate group (—OSO$_3$H) or a salt thereof, a glycopyranosyl group or a salt thereof, a phosphate ester of a glycopyranosyl group or a salt of the ester, a sulfate ester of a glycopyranosyl group or a salt of the ester, or a piperidinopiperidinocarbonyloxy group.

2. A diphenylacrylonitrile derivative selected from among the following compounds:

(Z)-2-(3,4-dimethoxy-phenyl)-3-(4-hydroxy-phenyl)-acrylonitrile;

4-[(Z)-2-cyano-2-(3,4-dimethoxy-phenyl)-vinyl]-phenyl [1,4']bipiperidinyl-1'-carboxylate;

4-[(Z)-2-cyano-2-(3,4-dimethoxy-phenyl)-vinyl]-phenyl acetate;

(Z)-2-(3,4-dimethoxy-phenyl)-3-[4-(2-methoxy-ethoxymethoxy)-phenyl]-acrylonitrile;

(Z)-2-(3,4-dimethoxy-phenyl)-3-(2-hydroxy-phenyl)-acrylonitrile;

(Z)-2-(3,4-dimethoxy-phenyl)-3-(4-hydroxy-3-methoxy-phenyl)-acrylonitrile;

(Z)-3-(3,4-dihydroxy-phenyl)-2-(3,4-dimethoxy-phenyl)-acrylonitrile;

(Z)-2-(3,4-dimethoxy-phenyl)-3-(3-hydroxy-2-methoxy-phenyl)-acrylonitrile;

(Z)-2-(3,4-dimethoxy-phenyl)-3-(4-hydroxy-3,5-dimethyl-phenyl)-acrylonitrile;

(Z)-2-(3,4-dimethoxy-phenyl)-3-(3-ethoxy-4-hydroxy-phenyl)-acrylonitrile;

(Z)-2-(4-butoxy-phenyl)-3-(4-hydroxy-phenyl)-acrylonitrile;

(Z)-3-(4-hydroxy-phenyl)-2-(3,4,5-trimethoxy-phenyl)-acrylonitrile;

(Z)-2-(3,4-dimethoxy-phenyl)-3-(4-hydroxy-phenyl)-acrylonitrile, sodium salt;

4-[(Z)-2-cyano-2-(3,4-dimethoxy-phenyl)-vinyl]-benzonitrile;

(Z)-3-(2,3-difluoro-phenyl)-2-(3,4-dimethoxy-phenyl)-acrylonitrile;

(Z)-3-(2,4-difluoro-phenyl)-2-(3,4-dimethoxy-phenyl)-acrylonitrile;

(Z)-3-(2,5-difluoro-phenyl)-2-(3,4-dimethoxy-phenyl)-acrylonitrile;

(Z)-3-(3,4-difluoro-phenyl)-2-(3,4-dimethoxy-phenyl)-acrylonitrile;

(Z)-3-(3,5-difluoro-phenyl)-2-(3,4-dimethoxy-phenyl)-acrylonitrile;

(Z)-2-(3,4-dimethoxy-phenyl)-3-(2,3,4-trifluoro-phenyl)-acrylonitrile;

(Z)-2-(3,4-dimethoxy-phenyl)-3-(2,3,5-trifluoro-phenyl)-acrylonitrile;

(Z)-2-(3,4-dimethoxy-phenyl)-3-(2,3,6-trifluoro-phenyl)-acrylonitrile;

(Z)-2-(3,4-dimethoxy-phenyl)-3-(2,4,5-trifluoro-phenyl)-acrylonitrile;

(Z)-2-(3,4-dimethoxy-phenyl)-3-(3,4,5-trifluoro-phenyl)-acrylonitrile;

(Z)-3-(2,6-difluoro-phenyl)-2-(3,4-dimethoxy-phenyl)-acrylonitrile;

(Z)-2-(3,4-dimethoxy-phenyl)-3-(3-nitro-phenyl)-acrylonitrile;

(Z)-3-(4-amino-phenyl)-2-(3,4-dimethoxy-phenyl)-acrylonitrile;

ethyl[4-[(Z)-2-cyano-2-(3,4-dimethoxy-phenyl)-vinyl]-phenoxy]-acetate;

methyl 4-[(Z)-2-cyano-2-(3,4-dimethoxy-phenyl)-vinyl]-benzoate;

(Z)-2-(3,4-dimethoxy-phenyl)-3-(2-nitro-phenyl)-acrylonitrile;

(Z)-3-(4-chloro-3-nitro-phenyl)-2-(3,4-dimethoxy-phenyl)-acrylonitrile;

(Z)-2-(3,4-dimethoxy-phenyl)-3-(2-fluoro-5-nitro-phenyl)-acrylonitrile;

(Z)-2-(3,4-dimethoxy-phenyl)-3-(4-ethoxy-3-nitro-phenyl)-acrylonitrile;

4-[(Z)-2-cyano-2-(3,4-dimethoxy-phenyl)-vinyl]-phenyl methyl succinate;

4-[(Z)-2-cyano-2-(3,4-dimethoxy-phenyl)-vinyl]-phenyl ethyl succinate;

bis-{4-[(Z)-2-cyano-2-(3,4-dimethoxy-phenyl)-vinyl]-phenyl}succinate;

(Z)-2-(3,4-dimethoxyphenyl)-3-(4-β-D-glucopyranosylphenyl)-acrylonitrile;

(Z)-2-(3,4-dimethoxy-phenyl)-3-(4-hydroxy-3-nitro-phenyl)-acrylonitrile;

(Z)-2-(3,4-dimethoxy-phenyl)-3-(6-nitro-benzo[1,3]dioxol-5-yl)-acrylonitrile;

(Z)-3-(3,4-dimethoxy-phenyl)-2-[4-(2-methoxy-ethoxymethoxy)-phenyl]-acrylonitrile;

(Z)-2-(3,5-bis-trifluoromethyl-phenyl)-3-(4-hydroxy-phenyl)-acrylonitrile;

(E)-2-(3,4-dimethoxy-phenyl)-3-(4-hydroxy-phenyl)-acrylonitrile;

(Z)-2-(3,4-dimethoxyphenyl)-3-(4-β-maltosyl-phenyl)-acrylonitrile;

(Z)-2-(3,4-dimethoxy-phenyl)-3-(2-ethoxy-5-nitro-phenyl)-acrylonitrile;

(Z)-2-(3,4-dimethoxy-phenyl)-3-(3-hydroxy-4-nitro-phenyl)-acrylonitrile;

(Z)-2-(3,4-dimethoxyphenyl)-3-(4-β-maltotriosyl-phenyl)-acrylonitrile;

(Z)-2-(3,4-dimethoxy-phenyl)-3-(3-fluoro-2-hydroxy-phenyl)-acrylonitrile;

(Z)-2-(3,4-dimethoxy-phenyl)-3-[3-fluoro-4-(2-methoxy-ethoxymethoxy)-phenyl]-acrylonitrile;

(Z)-2-(3,4-dimethoxy-phenyl)-3-(3-fluoro-4-hydroxy-phenyl)-acrylonitrile;

mono-{4-[(Z)-2-cyano-2-(3,4-dimethoxy-phenyl)-vinyl]-phenyl}sodium phosphate;

4-[(Z)-1-cyano-2-(3,4-dimethoxy-phenyl)-vinyl]phenyl acetate;

(Z)-2-(3,4-dimethoxy-phenyl)-3-(4-formyl-phenyl)-acrylonitrile;

4-[(Z)-1-cyano-2-(3,4-dimethoxy-phenyl)-vinyl]-2-ethoxy-phenyl acetate;

4-[(Z)-1-cyano-2-(3,4-dimethoxy-phenyl)-vinyl]-2-fluoro-phenyl acetate;

4-[(Z)-2-cyano-2-(3,4,5-trimethoxy-phenyl)-vinyl]-phenyl acetate;

ethyl7-[4-[(Z)-2-cyano-2-(3,4-dimethoxy-phenyl)-vinyl]-phenoxy]-heptanoate;

4-[(Z)-1-cyano-2-(3,4-dimethoxy-phenyl)-vinyl]-phenyl 8-bromo-octanoate;

(Z)-3-(3-amino-phenyl)-2-(3,4-dimethoxy-phenyl)-acrylonitrile, hydrochloride;

sodium mono-{4-[(Z)-2-cyano-2-(3,4-dimethoxy-phenyl)-vinyl]-2methoxy-phenyl}phosphate;

mono-{4-[(Z)-2-cyano-2-(3,4-dimethoxy-phenyl)-vinyl]-phenyl}phosphate;

mono-{4-[(Z)-2-cyano-2-(3,4-dimethoxy-phenyl)-vinyl]-2-methoxy-phenyl}phosphate;

N-[3-[(Z)-2-cyano-2-(3,4-dimethoxy-phenyl)-vinyl]-phenyl]-acetamide;

(Z)-2-(3,4-dimethoxyphenyl)-3-[4-(6-phospho-β-D-glucopyranosyl)-phenyl]-acrylonitrile;

sulphoric acid mono{4-[(Z)-2-cyano-2-(3,4-dimethoxy-phenyl)-vinyl]-phenyl}ester triethylammonium salt;

(Z)-2-(3,4-dimethoxyphenyl)-3-[4-(6-phospho-β-D-glucopyranosyl)-phenyl]-acrylonitrile sodium salt;

(Z)-2-(3,4-dimethoxy-phenyl)-3-(2-hydroxy-5-nitro-phenyl)-acrylonitrile;

(Z)-2-(3,4-dimethoxy-phenyl)-3-(4-fluoro-3-nitro-phenyl)-acrylonitrile;

(Z)-2-(3,4-dimethoxy-phenyl)-3-(3-hydroxy-4,5-dimethoxy-phenyl)-acrylonitrile; and (Z)-2-(3,4-dimethoxy-phenyl)-3-(4-hydroxy-3,5-dimethoxy-phenyl)-acrylonitrile.

3. A method of overcoming an anticancer drug resistance comprising administering to a patient an effective amount of a diphenylacrylonitrile derivative represented by the following formula (1) or a salt thereof:

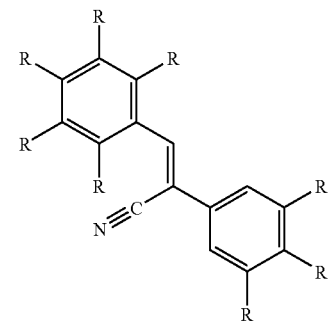

(1)

wherein, each of 8 R's, which are the same or different from one another, represents a hydrogen atom, a hydroxyl group, a nitro group, an amino group, an acetylamino group (—NHCOCH$_3$ group), a cyano group (—CN group), a formyl group (—CHO group), —COOR$_1$ (R$_1$ is hydrogen or C$_1$-C$_4$ alkyl), —O(CH$_2$)$_n$COOR$_2$ (n=1-7: R$_2$ is hydrogen or C$_1$-C$_4$ alkyl), —OOCCH$_2$CH$_2$COOR$_3$ (R$_3$ is hydrogen, C$_1$-C$_4$ alkyl, (Z)-2-(3,4-dimethoxy-phenyl)-3-(4-hydroxy-phenyl)-acrylonitrile, or glycopyranosyl), a C1-C8 alkoxy group, a C$_1$-C$_4$ alkyl group, a halogen atom, a C$_1$-C$_4$ alkoxy C$_1$-C$_4$ alkoxy C$_1$-C$_4$ alkoxy group, a C$_2$-C$_8$ acyloxy group, a C$_2$-C$_8$ halogenoacyloxy group, a methylenedioxy group, a trifluoromethyl group, a phosphate group (—OP(O)(OH)$_2$) or a salt thereof, a sulfate group (—OSO$_3$H) or a salt thereof, a glycopyranosyl group or a salt thereof, a phosphate ester of a glycopyranosyl group or a salt of the ester, a sulfate ester of a glycopyranosyl group or a salt of the ester, or a piperidinopiperidinocarbonyloxy group, wherein the anticancer drug can serve as a substrate for a breast cancer resistance protein (BCRP).

4. A method of enhancing an effect of an anticancer drug comprising administering to a patient an effective amount of a diphenylacrylonitrile derivative represented by the following formula (1) or a salt thereof:

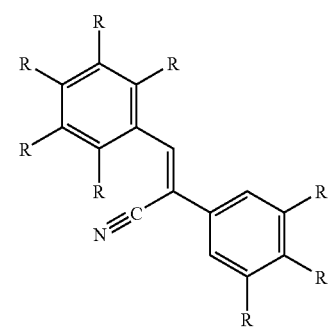

(1)

wherein, each of 8 R's, which are the same or different from one another, represents a hydrogen atom, a hydroxyl group, a nitro group, an amino group, an acetylamino group (—NHCOCH$_3$ group), a cyano group (—CN group), a formyl group (—CHO group), —COOR$_1$ (R$_1$ is hydrogen or $C_1$-$C_4$ alkyl), —O(CH$_2$)$_n$COOR$_2$ (n=1-7: R$_2$ is hydrogen or $C_1$-$C_4$ alkyl), —OOCCH$_2$CH$_2$COOR$_3$ (R$_3$ is hydrogen, $C_1$-$C_4$ alkyl, (Z)-2-(3,4-dimethoxy-phenyl)-3-(4-hydroxy-phenyl)-acrylonitrile, or glycopyranosyl), a $C_1$-$C_8$ alkoxy group, a $C_1$-$C_4$ alkyl group, a halogen atom, a $C_1$-$C_4$ alkoxy $C_1$-$C_4$ alkoxy $C_1$-$C_4$ alkoxy group, a $C_2$-$C_8$ acyloxy group, a $C_2$-$C_8$ halogenoacyloxy group, a methylenedioxy group, a trifluoromethyl group, a phosphate group (—OP(O)(OH)$_2$) or a salt thereof a sulfate group (—OSO$_3$H) or a salt thereof, a glycopyranosyl group or a salt thereof, a phosphate ester of a glycopyranosyl group or a salt of the ester, a sulfate ester of a glycopyranosyl group or a salt of the ester, or a piperidinopiperidinocarbonyloxy group, wherein the anticancer drug can serve as a substrate for a breast cancer resitance protein (BCRP).

5. A method of treating cancer comprising administering to a patient an anticancer drug which can serve as a substrate for a breast cancer resistance protein (BCRP) and an effective amount of a diphenylacrylonitrile derivative represented by the following formula (1) or a salt thereof:

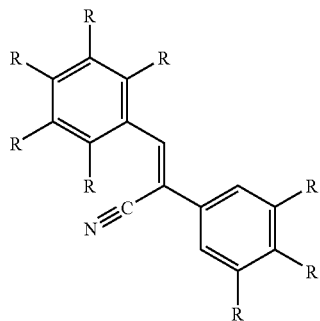

(1)

wherein, each of 8 R's, which are the same or different from one another, represents a hydrogen atom, a hydroxyl group, a nitro group, an amino group, an acetylamino group (—NHCOCH$_3$ group), a cyano group (—CN group), a formyl group (—CHO group), —COOR$_1$ (R$_1$ is hydrogen or $C_1$-$C_4$ alkyl), —O(CH$_2$)$_n$COOR$_2$ (n=1-7: R$_2$ is hydrogen or $C_1$-$C_4$ alkyl), —OOCCH$_2$CH$_2$COOR$_3$ (R$_3$ is hydrogen, $C_1$-$C_4$ alkyl, (Z)-2-(3,4-dimethoxy-phenyl)-3-(4-hydroxy-phenyl)-acrylonitrile, or glycopyranosyl), a $C_1$-$C_8$ alkoxy group, a $C_1$-$C_4$ alkyl group, a halogen atom, a $C_1$-$C_4$ alkoxy $C_1$-$C_4$ alkoxy $C_1$-$C_4$ alkoxy group, a $C_2$-$C_8$ acyloxy group, a $C_2$-$C_8$ halogenoacyloxy group, a methylenedioxy group, a trifluoromethyl group, a phosphate group (—OP(O)(OH)$_2$) or a salt thereof, a sulfate group (—OSO$_3$H) or a salt thereof, a glycopyranosyl group or a salt thereof, a phosphate ester of a glycopyranosyl group or a salt of the ester, a sulfate ester of a glycopyranosyl group or a salt of the ester, or a piperidinopiperidinocarbonyloxy group.

6. A method of inhibiting a breast cancer resistance protein (BCRP) comprising administering to a patient an effective amount of a diphenylacrylonitrile derivative according to claim 2.

7. A method of overcoming an anticancer drug resistance comprising administering to a patient an effective amount of a diphenylacrylonitrile derivative according to claim 2, wherein the anticancer drug can serve as a substrate for a breast cancer resistance protein (BCRP).

8. A method of enhancing an effect of an anticancer drug comprising administering to a patient an effective amount of a diphenylacrylonitrile derivative according to claim 2, wherein the anticancer drug can serve as a substrate for a breast cancer resistance protein (BCRP).

9. A method of treating cancer comprising administering to a patient an anticancer drug which can serve as a substrate for a breast cancer resistance protein (BCRP) and an effective amount of a diphenylacrylonitrile derivative according to claim 2.

* * * * *

UNITED STATES PATENT AND TRADEMARK OFFICE
CERTIFICATE OF CORRECTION

PATENT NO. : 7,371,773 B2
APPLICATION NO. : 10/544064
DATED : May 13, 2008
INVENTOR(S) : Ryuta Yamazaki et al.

It is certified that error appears in the above-identified patent and that said Letters Patent is hereby corrected as shown below:

Col. 46
Line 33 claim 2, "ethyl[4-[(Z)-2-cyano-2-(3,4-dimethoxy-phenyl)-vinyl]-" should read -- ethyl [4-[(Z)-2-cyano-2-(3,4-dimethoxy-phenyl)-vinyl]- --;

Line 52, "phenyl}succinate;" should read -- phenyl} succinate; --.

Col. 47
Line 16 claim 2, "phenyl}sodium phosphate;" should read -- phenyl} sodium phosphate; --;

Line 30, "ethyl7-[4-[(Z)-2-cyano-2-(3,4-dimethoxy-phenyl)-vinyl]-" should read -- ethyl 7-[4-[(Z)-2-cyano-2-(3,4-dimethoxy-phenyl)-vinyl]- --;

Line 39, "nyl)-vinyl]-2 –methoxy-phenyl}phosphate;" should read -- nyl)-vinyl]-2 –methoxy-phenyl} phosphate; --;

Line 41, "phenyl}phosphate;" should read -- phenyl} phosphate; --;

Line 43, "2-methoxy-phenyl}phosphate;" should read -- 2-methoxy-phenyl} phosphate; --.

Col. 48
Line 26 claim 3, "C1-C8 alkoxy" should read -- $C_1$-$C_8$ alkoxy --.

UNITED STATES PATENT AND TRADEMARK OFFICE
CERTIFICATE OF CORRECTION

| | |
|---|---|
| PATENT NO. | : 7,371,773 B2 |
| APPLICATION NO. | : 10/544064 |
| DATED | : May 13, 2008 |
| INVENTOR(S) | : Ryuta Yamazaki et al. |

It is certified that error appears in the above-identified patent and that said Letters Patent is hereby corrected as shown below:

<u>Col. 49</u>
    Line 9 claim 4, "or a salt thereof a sulfate group" should read -- or a salt thereof, a sulfate group --.

Signed and Sealed this

Second Day of September, 2008

JON W. DUDAS
*Director of the United States Patent and Trademark Office*